(12) United States Patent
Shaw et al.

(10) Patent No.: US 10,214,527 B2
(45) Date of Patent: Feb. 26, 2019

(54) TRIAZOLOPYRIDINE INHIBITORS OF MYELOPEROXIDASE

(71) Applicant: BRISTOL-MYERS SQUIBB COMPANY, Princeton, NJ (US)

(72) Inventors: Scott A. Shaw, Lawrence Township, NJ (US); Joanne M. Smallheer, Yardley, PA (US)

(73) Assignee: Bristol-Myers Squibb Company, Princeton, NJ (US)

(*) Notice: Subject to any disclaimer, the term of this patent is extended or adjusted under 35 U.S.C. 154(b) by 0 days.

(21) Appl. No.: 15/756,378

(22) PCT Filed: Aug. 30, 2016

(86) PCT No.: PCT/US2016/049355
§ 371 (c)(1),
(2) Date: Feb. 28, 2018

(87) PCT Pub. No.: WO2017/040451
PCT Pub. Date: Mar. 9, 2017

(65) Prior Publication Data
US 2018/0282320 A1 Oct. 4, 2018

Related U.S. Application Data

(60) Provisional application No. 62/213,788, filed on Sep. 3, 2015.

(51) Int. Cl.
C07D 401/14 (2006.01)
A61K 31/437 (2006.01)
C07D 471/04 (2006.01)

(52) U.S. Cl.
CPC .................. *C07D 471/04* (2013.01)

(58) Field of Classification Search
CPC .............. C07D 401/14; A61K 31/437
USPC ........................... 514/303; 546/119
See application file for complete search history.

(56) References Cited

FOREIGN PATENT DOCUMENTS

WO  9901607  *  1/1999

* cited by examiner

*Primary Examiner* — Niloofar Rahmani
(74) *Attorney, Agent, or Firm* — Elliott Korsen

(57) ABSTRACT

The present invention provides compounds of Formula (I): wherein A is as defined in the specification, and compositions comprising any of such novel compounds. These compounds are myeloperoxidase (MPO) inhibitors and/or eosinophil peroxidase (EPX) inhibitors, which may be used as medicaments.

(I)

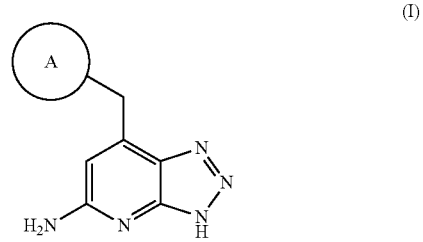

9 Claims, No Drawings

TRIAZOLOPYRIDINE INHIBITORS OF MYELOPEROXIDASE

CROSS-REFERENCE TO RELATED APPLICATIONS

This application claims priority from U.S. Provisional Application No. 62/213,788 filed Sep. 3, 2015, the disclosures of which are incorporated herein by reference in their entirety.

FIELD OF THE INVENTION

The present invention relates to novel triazolopyridine compounds, which are myeloperoxidase (MPO) inhibitors and/or eosinophil peroxidase (EPX) inhibitors, compositions containing them, and methods of using them, for example, for the treatment and/or prophylaxis of atherosclerosis, heart failure, chronic obstructive pulmonary disease (COPD), and related diseases.

BACKGROUND OF THE INVENTION

Cardiovascular disease is a major health risk throughout the industrialized world. Atherosclerosis, the most prevalent of cardiovascular diseases, is the principal cause of heart attack and stroke, and thereby the principal cause of death in the United States. Atherosclerosis is a complex disease involving many cell types and molecular factors (for a detailed review, see Weber et al., Nature Med., 17(11):1410-1422 (2011)).

MPO inhibitors have been suggested to reduce the atherosclerotic burden and/or the vulnerability of existing atherosclerotic lesions and thereby decrease the risk of acute myocardial infarction, unstable angina or stroke, and reduce ischemia-reperfusion injury during acute coronary syndrome and ischemic cerebrovascular events. Several lines of data support a role for MPO in atherosclerosis. MPO is expressed in the shoulder regions and necrotic core of human atherosclerotic lesions and active enzyme has been isolated from autopsy specimens of human lesions (Daugherty, A. et al., J. Clin. Invest., 94(1):437-444 (1994)). Moreover, HOCl-modified lipoproteins have been detected in advanced human atherosclerotic lesions (Hazell, L. J. et al., J. Clin. Invest., 97:1535-1544 (1996)). In eroded and ruptured human lesions, as compared to fatty streaks, an increased number of MPO expressing macrophages have been demonstrated, suggesting a particular role for MPO in acute coronary syndromes (Sugiyama, S. et al., Am. J. Pathol., 158(3):879-891 (2001); Tavora, F. R., BMC Cardiovasc. Disord., 9:27 (Jun. 23, 2009).

Data accumulated during the last fifteen years indicate that the pro-atherogenic actions of MPO include oxidation of lipoproteins, induction of endothelial dysfunction via consuming nitric oxide and destabilization of atherosclerotic lesions by activation of proteases (Nicholls, S. J. et al., Arterioscler. Thromb. Vasc. Biol., 25(6): 1102-1111 (2005); Nicholls, S. J. et al., JLR, S346-S351 (2009)). Several studies have focused on nitro- and chlorotyrosine modifications of LDL and HDL lipoproteins. Since chlorotyrosine modifications in vivo are generated by hypochlorous acid produced by MPO these modifications are regarded as specific markers of MPO activity (Hazen, S. et al., J. Clin. Invest., 99(9):2075-2081 (1997)).

ApoA-I isolated from atherosclerotic lesions is modified by reactive chlorine and nitrogen species as well as by reactive carbonyls (Pennathur, S. et al., J. Biol. Chem., 279:42977-42983 (2004); Shao, B. et al., J. Biol. Chem., 279:7856-7866 (2004); Zheng, L. et al., J. Clin. Invest., 114(4):529-541 (2004); Shao, B. et al. JBC in press (2012)). Chlorotyrosine modification of apoA1, the main apolipoprotein of HDL cholesterol, was associated with impaired cholesterol acceptor function (Bergt, C. S. et al., Proc. Natl. Acad. Sci. USA, 101(35):13032-13037 (2004); Zheng, L. et al., J. Clin. Invest., 114(4):529-541 (2004)). Thus, oxidation of apoA-I amino acid residues by the MPO-$H_2O_2$—$Cl^-$ system is one mechanism for loss of its biological activities.

The lipid and protein content of LDL are also targets for MPO oxidation and presence of chlorotyrosine in LDL extracted from human atherosclerotic tissues has been shown (Hazen, S. et al., J. Clin. Invest., 2075-2081 (1997)). LDL particles exposed to MPO in vitro become aggregated, leading to facilitated uptake via macrophage scavenger receptors and foam cell formation (Hazell, L. J. et al., Biochem. J., 290(Pt. 1): 165-172 (1993); Podrez, E. A. et al., J. Clin. Invest., 105:1095-1108 (2000)). Thus, MPO appears to play a role in the generation of oxidized LDL, which contributes to atherosclerosis plaque development.

Further evidence implicating MPO in the pathophysiology of atherosclerosis comes from the study of hMPO transgenic mice crossed with LDL-R KO mice (Castelini L. W. et al., J. Lipid Res., 47:1366-1377 (2006)). These mice expressed MPO in lesions and developed significantly larger aortic lesions than control LDL-R KO mice.

Many clinical studies have implicated MPO in cardiovascular disease in human patients. Patients with established coronary artery disease have higher plasma and leukocyte MPO levels than healthy controls (Zhang, R. et al., JAMA, 286(17):2136-2142 (2001)). Moreover, in three large prospective studies plasma levels of MPO predicted the risk of future coronary events or revascularization (Baldus, S. et al., Circulation, 108(12):1440-1445 (2003); Brennan, M. et al., N. Engl. J. Med., 349(17):1595-1604 (2003); Kohli, P. et al., Circulation, 122:A13175 (2010)). In two recent large nested case control prospective studies, the EPIC-Norfolk and MONICA-/KORA Augsburg studies, baseline MPO levels in these initially healthy populations turned out to be an excellent predictor of future risk of CAD and CHD respectively, showing that this inflammatory marker precedes the presentation of clinical symptoms of CVD (Meuwese, M. C. et al., J. Am. Coll. Cardiol., 50:159-165 (2007); Karakas et al., J. Int. Med., 271:43-50 (2011)). Interestingly, MPO deficient humans are less affected by cardiovascular disease than controls with normal MPO levels (Kutter, D. et al., Acta Haematol., 104:10-15 (2000)). A polymorphism in the MPO promoter affects expression leading to high and low MPO expressing individuals. In three different studies the high expression genotype has been associated with an increased risk of cardiovascular disease (Nikpoor, B. et al., Am. Heart J., 142(2):336-339 (2001); Makela, R. et al., Lab. Invest., 83(7):919-925 (2003); Asselbergs, F. W. et al., Am. J. Med., 116(6):429-430 (2004)).

MPO inhibitors are expected to preserve heart function and reduce heart failure burden in patients. In MPO null mice, preservation of left ventricular (LV) function has been observed in both a coronary artery ligation model (Askari, A. T. et al., J. Exp. Med., 197:615-624 (2003)) and an ischemia reperfusion model (Vasilyev, N. et al., Circulation, 112:2812-2820 (2005)), suggesting that MPO may provide a mechanistic link between inflammation, oxidant stress, and impaired cardiac remodeling. High circulating levels of MPO have also been linked to chronic heart failure in patients. Systemic MPO was increased in patients with established chronic systolic HF and correlated with diastolic dysfunction independent of age and plasma B-type natriuretic peptide (Tang, W. H. et al., *Am. J. Cardiol.*, 98:796-799 (2006)). Studies also showed that systemic MPO in subjects with myocardial infarction (MI) (Mocatta, T. J. et al., *J. Am. Coll. Cardiol.*, 49:1993-2000 (2007)) or chronic systolic HF (Tang, W. H. et al., *J. Am. Coll. Cardiol.*, 49:2364-2370 (2007)) may predict long-term adverse clinical events.

Inhibitors of MPO or EPX may be used to treat other neuroinflammatory diseases, including multiple sclerosis, Alzheimer's disease, Parkinson's disease, multiple system atrophy, and stroke as well as other inflammatory diseases or conditions like asthma, COPD, cystic fibrosis, inflammatory bowel disease, chronic kidney disease, renal glomerular damage and rheumatoid arthritis.

In these chronic inflammatory diseases, a role of MPO in the development of tissue injury has been suggested. In lesional tissues of patients with Alzheimer's disease, MPO protein was detected along with elevated levels of chlorotyrosine (Green, P. S. et al., *J. Neurochem.*, 90:724-733 (2004)). In an animal model of Parkinson's disease, increased levels of chlorotyrosine and HOCl-modified proteins in brain tissues have been reported (Choi, D. K. et al., *J. Neuroscience*, 25(28):6394-6600 (2005)). In asthmatic patients the level of bromotyrosine, a molecular fingerprint of eosinophil-catalyzed oxidation was associated with symptom severity (Wedes, S. H. et al., *J. Pediatr.*, 248-255 (2011)). Upon allergen challenge, a model that elicits primarily a strong eosinophilic response, lung segments of asthmatic subjects exhibit a >10 fold increase in bronchioalveolar lavage 3-bromotyrosine an indicator of eosinophil activity vs. a 3-fold increase in 3-chlorotyrosine characteristic of MPO activity (Wu, W. et al., *JCI*, 105:1455-1463 (2000)). The presence of HOCl-modified protein was also detected in patients with membranous glomerulonephritis (Grone et al., *Lab. Invest.*, 82:5-14 (2002)). High MPO circulating levels have been implicated in the development of cardiovascular and chronic kidney disease in patients on hemodialysis (Honda, H. et al., *Clin. J. Am. Soc., Nephrol.*, 142-151 (2009). In addition MPO activity and 3-chlorotyrosine levels were also increased during hemodyalisis in patients with end-stage renal disease (Delporte, C et al., *Talanta*, 99:603-609 (2012)). Similarly, there is accumulation of neutrophils and eosinophils in conjunction with MPO and EPX seen in intestinal mucosa of patients with inflammatory bowel disease (Kruidenier, L. et al., *J. Pathol.*, 201:17-27 (2003); Carlson, M. et al., *Am. J. Gastrol.*, 94(7): 1876-1883 (1999)) and in synovial fluids of rheumatoid arthritis patients (Edwards, S. W. et al., *Biochem. J.*, 250: 81-85 (1988); Nucombe, H. L. et al., *Ann. Rheum. Dis.*, 50:237-242 (1991)).

Thus, there is considerable evidence that MPO and/or EPX derived oxidants contribute to tissue injury in chronic inflammatory disorders. MPO and/or EPX inhibitors are anticipated to reduce the levels of oxidants and tissue injury associated with the progression of these diseases.

SUMMARY OF THE INVENTION

The present disclosure provides novel triazolopyridine compounds, including stereoisomers, tautomers, pharmaceutically acceptable salts, or solvates thereof, which are useful as MPO inhibitors and/or EPX inhibitors.

The present invention also provides processes and intermediates for making the compounds of the present invention.

The present invention also provides pharmaceutical compositions comprising a pharmaceutically acceptable carrier and at least one of the compounds of the present invention or stereoisomers, tautomers, pharmaceutically acceptable salts, or solvates thereof.

The compounds of the invention may be used in the treatment and/or prophylaxis of diseases or disorders associated with the activity of MPO and/or EPX.

The compounds of the invention may be used in therapy.

The compounds of the invention may be used for the manufacture of a medicament for the treatment and/or prophylaxis of diseases or disorders associated with the activity of MPO and/or EPX.

Examples of diseases or disorders associated with the activity of MPO and/or EPX include, but are not limited to, atherosclerosis, coronary artery disease, acute coronary syndrome, dyslipidemias and the sequelae thereof, heart failure, lung diseases including asthma, COPD and cystic fibrosis, and neuroinflammatory diseases, including multiple sclerosis, Alzheimer's disease, Parkinson's disease, multiple system atrophy, and stroke, as well as chronic inflammatory diseases such as inflammatory bowel disease, renal glomerular damage and rheumatoid arthritis.

The compounds of the invention can be used alone, in combination with other compounds of the present invention, or in combination with one or more, preferably one to two other agent(s).

Other features and advantages of the invention will be apparent from the following detailed description and claims.

DETAILED DESCRIPTION OF THE INVENTION

I. Compounds of the Invention

In a first aspect, the present invention provides, inter alia, a compound of Formula (I):

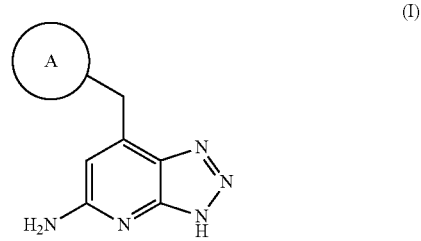

or a stereoisomer, a tautomer, a pharmaceutically acceptable salt, or a solvate thereof, wherein:

ring A is independently selected from: phenyl, naphthyl and a 6-membered heteroaryl comprising carbon atoms and 1 to 2 nitrogen atoms; wherein each ring moiety is substituted with 0-1 $R^2$ and 0-3 $R^3$;

$R^2$ is independently selected from: halogen, $C_{1-4}$ alkyl substituted with 0-1 OH, $C_{1-4}$ alkoxy, $C_{1-4}$ haloalkyl, $C_{1-4}$ haloalkoxy, CN, $CO_2(C_{1-4}$ alkyl), $SO_2(C_{1-4}$ alkyl), $-(CH_2)_n(X_1)_n(CH_2)_nR^4$, and $-(CH_2)_nCONH(CH_2)_mR^4$;

$X_1$ is independently selected from: O, CO, $NR^1$ and $S(O)_p$;

$R^1$ is independently selected from: H and $C_{1-4}$ alkyl;

$R^3$ is, independently at each occurrence, selected from: OH, halogen, $C_{1-4}$ alkyl, $C_{1-4}$ alkoxy, $C_{1-4}$ haloalkyl, and $C_{1-4}$ haloalkoxy;

alternatively, when $R^2$ and one of the $R^3$s are attached to two adjacent carbon atoms of ring A selected from phenyl and pyridyl, they can be combined with the two attached carbon atoms to form a 5- to 6-membered carbocycle or heterocycle comprising carbon atoms and 0-3 additional heteroatoms selected from N, $NR^b$, O, and $S(O)_p$, wherein said carbocycle or heterocycle is substituted with 0-2 $R^a$;

$R^4$ is independently at each occurrence selected from: $C_{3-6}$ cycloalkyl substituted with 0-3 $R^c$, phenyl substituted with 0-4 $R^c$, and 5- to 10-membered heterocycle comprising carbon atoms and 1-4 heteroatoms selected from N, $NR^b$, O, and S; wherein said heterocycle is substituted with 0-3 $R^c$;

$R^a$ is, independently at each occurrence, selected from: OH, CN, halogen, $C_{1-4}$ alkyl, $C_{1-4}$ alkoxy, $C_{1-4}$ haloalkyl, and $C_{1-4}$ haloalkoxy;

$R^b$ is, independently at each occurrence, selected from: H, $C_{1-4}$ alkyl, $C_{1-4}$ haloalkyl, $CO(C_{1-4}$ alkyl), $CO_2(C_{1-4}$ alkyl), $SO_2(C_{1-4}$ alkyl), —$(CH_2)_t$-phenyl substituted with 0-1 $R^d$;

$R^c$ is, independently at each occurrence, selected from: OH, halogen, $C_{1-6}$ alkyl substituted with 0-1 OH, $C_{1-4}$ alkoxy, $C_{1-4}$ haloalkyl, $C_{1-4}$ haloalkoxy, CN, $CONH_2$, $CONH(C_{1-4}$ alkyl), $CON(C_{1-4}$ alkyl)$_2$, —$(O)_n(CH_2)_t$—$C_{3-6}$ carbocycle, —$(CH_2)_t(O)_n(C_{3-6}$ carbocycle), and —$(CH_2)_t$-(5- to 6-membered heterocycle comprising carbon atoms and 1-4 heteroatoms selected from N, $NR^b$, O, and S); wherein said carbocycle and heterocycle are substituted with 0-2 $R^d$;

$R^d$ is independently at each occurrence, selected from the group consisting of halogen, $C_{1-4}$ alkyl substituted with 0-1 OH, $C_{1-4}$ haloalkyl, $C_{1-4}$ alkoxy, $C_{1-4}$ haloalkoxy, CN, —$(CH_2)_t(O)_n$—$(C_{3-6}$ carbocycle) and —$(O)_n(CH_2)_t$—$(C_{3-6}$ carbocycle);

m is, independently at each occurrence, selected from 1, 2 and 3;

n is, independently at each occurrence, selected from 0 and 1;

p is, independently at each occurrence, selected from 0, 1 and 2; and t is, independently at each occurrence, selected from 0, 1, 2, and 3.

In a second aspect, the present invention includes a compound of Formula (I), or a stereoisomer, a tautomer, a pharmaceutically acceptable salt, or a solvate thereof, within the scope of the first aspect; wherein:

ring A is independently phenyl substituted with 0-1 $R^2$ and 0-3 $R^3$, pyridyl substituted with 0-1 $R^2$ and 0-2 $R^3$, or naphthyl substituted with 0-3 $R^3$.

In a third aspect, the present invention includes a compound of Formula (I), or a stereoisomer, a tautomer, a pharmaceutically acceptable salt, or a solvate thereof, within the scope of the first or second aspect; wherein:

ring A is independently phenyl substituted with 0-1 $R^2$ and 0-3 $R^3$ or pyridyl substituted with 0-1 $R^2$ and 0-2 $R^3$.

In a fourth aspect, the present invention includes a compound of Formula (I), or a stereoisomer, a tautomer, a pharmaceutically acceptable salt, or a solvate thereof, within the scope of the first aspects, wherein:

ring A is independently selected from:

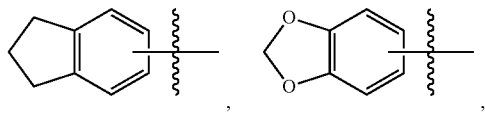

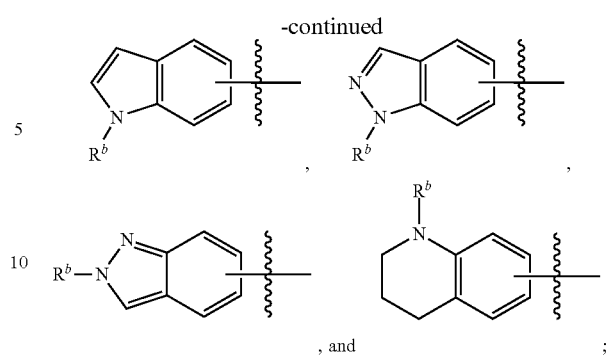

wherein each ring moiety is substituted with 0-1 $R^3$.

In a fifth aspect, the present invention includes a compound of Formula (II),

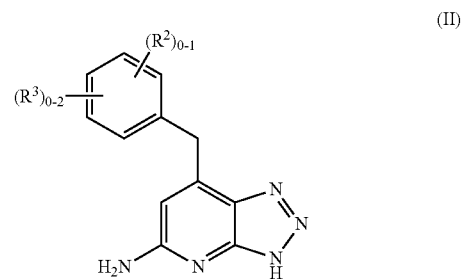

or a stereoisomer, a tautomer, a pharmaceutically acceptable salt, or a solvate thereof, within the scope of any of the first, second, and third aspects.

In a sixth aspect, the present invention includes a compound of Formula (I) or (II), or a stereoisomer, a tautomer, a pharmaceutically acceptable salt, or a solvate thereof, within the scope of any of the first, second, third, and fifth aspects, wherein:

$R^2$ is independently selected from: halogen, $C_{1-4}$ alkyl, $C_{1-4}$ alkoxy, $C_{1-4}$ haloalkyl, $C_{1-4}$ haloalkoxy, $CO_2(C_{1-4}$ alkyl), CN, Ph, Bn, 3-halo-Ph, 4-$C_{1-4}$ alkyl-Ph, 4-halo-phenoxy, OBn, COPh, —CONHBn, —CONHCH$_2$CH$_2$Ph, $SO_2(C_{1-4}$ alkyl), —CH$_2$SO$_2$Ph, pyrazol-1-yl, 1-Bn-pyrazol-3-yl,

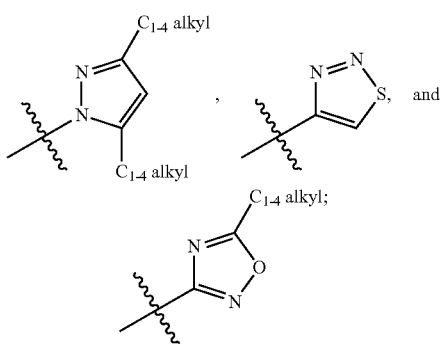

and $R^3$ is independently selected from: halogen, $C_{1-4}$ alkyl, and $C_{1-4}$ alkoxy.

In a seventh aspect, the present invention includes a compound of Formula (I) or (II), or a stereoisomer, a tautomer, a pharmaceutically acceptable salt, or a solvate thereof, within the scope of any of the first, second, third, fifth and sixth aspects, wherein:

R² is independently selected from: F, Cl, Me, t-Bu, OMe, CF₃, OCF₃, CO₂Me, CN, Ph, Bn, 3-F-Ph, 4-Me-Ph, 4-F-phenoxy, OBn, COPh, —CONH(CH₂)₁₋₂Ph, SO₂Me, —CH₂SO₂Ph, pyrazol-1-yl, 1-Bn-pyrazol-3-yl,

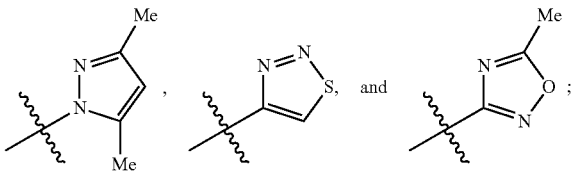 [SMILES: *n1nc(C)cc1C ; *c1csnn1 ; "and" ; *c1noc(C)n1]

and

R³ is independently selected from: F, Me and OMe.

In another embodiment, ring A is phenyl substituted with 0-1 R² and 0-3 R³.

In another embodiment, ring A is phenyl substituted with 0-1 R² and 0-2 R³.

In another embodiment, ring A is phenyl substituted with 1 R² and 0-2 R³.

In another embodiment, ring A is phenyl para- or meta-substituted with 1 R² and further substituted with 0-2 R³.

In another embodiment, ring A is naphthyl substituted with 0-1 R² and 0-3 R³.

In another embodiment, ring A is naphthyl substituted with 0-2 R³.

In another embodiment, ring A is pyridyl substituted with 0-1 R² and 0-2 R³.

In another embodiment, ring A is pyridyl substituted with 0-1 R² and 0-1 R³.

In an eighth aspect, the present invention provides a compound selected from the exemplified examples or a stereoisomer, a tautomer, a pharmaceutically acceptable salt, or a solvate thereof.

In another aspect, the present invention provides a compound selected from any subset list of compounds within the scope of the tenth aspect.

In another embodiment, the compounds of the present invention have IC₅₀ values ≤10 μM, using the MPO peroxidation assay disclosed herein, preferably, IC₅₀ values ≤3 μM, more preferably, IC₅₀ values ≤0.3 μM, even more preferably, IC₅₀ values ≤0.1 μM.

In another embodiment, the compounds of the present invention have IC₅₀ values ≤10 μM, using the MPO chlorination assay disclosed herein, preferably, IC₅₀ values ≤3 μM, more preferably, IC₅₀ values ≤0.3 μM, even more preferably, IC₅₀ values ≤0.1 μM.

In another embodiment, the compounds of the present invention have IC₅₀ values ≤10 μM, using the EPX bromination assay described herein, preferably, IC₅₀ values ≤3 μM, more preferably, IC₅₀ values ≤0.3 μM, even more preferably, IC₅₀ values ≤0.1 μM.

II. Other Embodiments of the Invention

In another embodiment, the present invention provides a composition comprising at least one of the compounds of the present invention or a stereoisomer, a tautomer, a pharmaceutically acceptable salt, or a solvate thereof.

In another embodiment, the present invention provides a pharmaceutical composition comprising a pharmaceutically acceptable carrier and at least one of the compounds of the present invention or a stereoisomer, a tautomer, a pharmaceutically acceptable salt, or a solvate thereof.

In another embodiment, the present invention provides a pharmaceutical composition, comprising a pharmaceutically acceptable carrier and a therapeutically effective amount of at least one of the compounds of the present invention or a stereoisomer, a tautomer, a pharmaceutically acceptable salt, or a solvate thereof.

In another embodiment, the present invention provides a pharmaceutical composition as defined above further comprising additional therapeutic agent(s).

In another embodiment, the present invention provides a process for making a compound of the present invention.

In another embodiment, the present invention provides an intermediate for making a compound of the present invention.

In another embodiment, the present invention provides a compound of the present invention, for use in therapy, alone, or optionally in combination with another compound of the present invention and/or at least one other type of therapeutic agent.

In another embodiment, the present invention provides a compound of the present invention for use in therapy, for the treatment and/or prophylaxis of diseases or disorders associated with the activity of MPO and/or EPX, alone, or optionally in combination with another compound of the present invention and/or at least one other type of therapeutic agent.

In another embodiment, the present invention provides a method for the treatment and/or prophylaxis of diseases or disorders associated with the activity of MPO and/or EPX, comprising administering to a patient in need of such treatment and/or prophylaxis a therapeutically effective amount of at least one of the compounds of the present invention, alone, or optionally in combination with another compound of the present invention and/or at least one other type of therapeutic agent.

In another embodiment, the present invention provides a method for the treatment and/or prophylaxis of diseases or disorders associated with the activity of MPO and/or EPX, comprising administering to a patient in need thereof a therapeutically effective amount of a first and second therapeutic agent, wherein the first therapeutic agent is a compound of the present invention and the second therapeutic agent is one other type of therapeutic agent.

In another embodiment, the present invention also provides the use of a compound of the present invention for the manufacture of a medicament for the treatment and/or prophylaxis of diseases or disorders associated with the activity of MPO and/or EPX, alone, or optionally in combination with another compound of the present invention and/or at least one other type of therapeutic agent.

In another embodiment, the present invention provides a combined preparation of a compound of the present invention and additional therapeutic agent(s) for simultaneous, separate or sequential use in therapy.

In another embodiment, the present invention provides a combined preparation of a compound of the present invention and additional therapeutic agent(s) for simultaneous, separate or sequential use in the treatment and/or prophylaxis of diseases or disorders associated with the activity of MPO and/or EPX.

Examples of diseases or disorders associated with the activity of MPO and/or EPX that may be prevented, modulated, or treated according to the present invention include, but are not limited to, atherosclerosis, coronary heart disease, coronary artery disease, coronary vascular disease, cerebrovascular disorders, peripheral vascular disease, dyslipidemias and the sequelae thereof, cardiovascular disorders, angina, ischemia, cardiac ischemia, heart failure, stroke, myocardial infarction, reperfusion injury, angioplastic restenosis, hypertension, vascular complications of diabetes, obesity or endotoxemia.

In one embodiment, examples of diseases or disorders include, but are not limited to, atherosclerosis, coronary artery disease, acute coronary syndrome, dyslipidemias and the sequelae thereof, heart failure, lung diseases including asthma, COPD and cystic fibrosis, and neuroinflammatory diseases, including multiple sclerosis, Alzheimer's disease, Parkinson's disease, multiple system atrophy, transient ischemic attack and stroke. In one embodiment, examples of diseases or disorders include atherosclerosis, coronary heart disease, cerebrovascular disorders and dyslipidemias and the sequelae thereof. In one embodiment, examples of diseases or disorders include coronary artery disease and acute coronary syndrome. In one embodiment, examples of diseases or disorders include dyslipidemias and the sequelae thereof. In one embodiment, examples of diseases or disorders include heart failure. In one embodiment, examples of diseases or disorders include lung diseases including asthma, COPD and cystic fibrosis. In one embodiment, examples of diseases or disorders include neuroinflammatory diseases, including multiple sclerosis, Alzheimer's disease, Parkinson's disease, multiple system atrophy, and stroke.

The compounds of the present invention may be employed in combination with additional therapeutic agent(s) selected from one or more, preferably one to three, of the following therapeutic agents: anti-atherosclerotic agents, anti-dyslipidemic agents, anti-diabetic agents, antihyperglycemic agents, anti-hyperinsulinemic agents, anti-thrombotic agents, anti-retinopathic agents, anti-neuropathic agents, anti-nephropathic agents, anti-ischemic agents, antihypertensive agents, diurectics, mineralocorticoid receptor antagonists, calcium channel blockers, anti-obesity agents, anti-hyperlipidemic agents, anti-hypertriglyceridemic agents, anti-hypercholesterolemic agents, anti-restenotic agents, anti-pancreatic agents, lipid lowering agents, anorectic agents, memory enhancing agents, anti-dementia agents, cognition promoting agents, appetite suppressants, agents for treating heart failure, agents for treating peripheral arterial disease, agents for treating malignant tumors, and anti-inflammatory agents.

In another embodiment, additional therapeutic agent(s) used in combined pharmaceutical compositions or combined methods or combined uses, are selected from one or more, preferably one to three, of the following therapeutic agents in treating atherosclerosis: anti-hyperlipidemic agents, plasma high-density lipoprotein (HDL)-raising agents, antihypercholesterolemic agents, cholesterol biosynthesis inhibitors (such as HMG CoA reductase inhibitors), acyl-coenzyme A:cholesterol acyltransferase (ACAT) inhibitors, cholesterylester transfer protein (CETP) inhibitors, liver X receptor (LXR) agonists, anti-probucol, raloxifene, nicotinic acid, niacinamide, cholesterol absorption inhibitors, bile acid sequestrants (such as anion exchange resins, or quaternary amines (e.g., cholestyramine or colestipol)), low density lipoprotein receptor inducers, clofibrate, fenofibrate, benzofibrate, cipofibrate, gemfibrizol, vitamin $B_6$, vitamin $B_{12}$, anti-oxidant vitamins, β-blockers, diurectics, mineralocorticoid receptor antagonists, calcium channel blockers, anti-diabetes agents, angiotensin II receptor antagonists, angiotensin converting enzyme inhibitors, platelet aggregation inhibitors, factor Xa inhibitors, anti-thrombotic agents, renin inhibitors, fibrinogen receptor antagonists, aspirin and fibric acid derivatives.

In another embodiment, additional therapeutic agent(s) used in combined pharmaceutical compositions or combined methods or combined uses, are selected from one or more, preferably one to three, of the following therapeutic agents in treating cholesterol biosynthesis inhibitor, particularly an HMG-CoA reductase inhibitor. Examples of suitable HMG-CoA reductase inhibitors include, but are not limited to, lovastatin, simvastatin, pravastatin, fluvastatin, atorvastatin, and rosuvastatin.

The present invention may be embodied in other specific forms without parting from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also understood that each individual element of the embodiments is its own independent embodiment. Furthermore, any element of an embodiment is meant to be combined with any and all other elements from any embodiment to describe an additional embodiment.

III. Chemistry

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Many geometric isomers of C=C double bonds, C=N double bonds, ring systems, and the like can also be present in the compounds, and all such stable isomers are contemplated in the present invention. Cis- and trans- (or E- and Z-) geometric isomers of the compounds of the present invention are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization. Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

As used herein, the term "alkyl" or "alkylene" is intended to include both branched and straight-chain saturated aliphatic hydrocarbon groups having the specified number of carbon atoms. For example, "$C_1$ to $C_{10}$ alkyl" or "$C_{1-10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$ to $C_6$ alkyl" or "$C_{1-6}$ alkyl" denotes alkyl having 1 to 6 carbon atoms. Alkyl group can be unsubstituted or substituted with at least one hydrogen being replaced by another chemical group. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl). When "$C_0$ alkyl" or "$C_0$ alkylene" is used, it is intended to denote a direct bond.

"Alkenyl" or "alkenylene" is intended to include hydrocarbon chains of either straight or branched configuration having the specified number of carbon atoms and one or more, preferably one to two, carbon-carbon double bonds that may occur in any stable point along the chain. For example, "$C_2$ to $C_6$ alkenyl" or "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3, pentenyl, 4-pentenyl, 2-hexenyl, 3-hexenyl, 4-hexenyl, 5-hexenyl, 2-methyl-2-propenyl, and 4-methyl-3-pentenyl.

"Alkynyl" or "alkynylene" is intended to include hydrocarbon chains of either straight or branched configuration having one or more, preferably one to three, carbon-carbon triple bonds that may occur in any stable point along the chain. For example, "$C_2$ to $C_6$ alkynyl" or "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, and hexynyl.

The term "alkoxy" or "alkyloxy" refers to an —O-alkyl group. "$C_1$ to $C_6$ alkoxy" or "$C_{1-6}$ alkoxy" (or alkyloxy), is intended to include $C_1$, $C_2$, $C_3$, $C_4$, $C_5$, and $C_6$ alkoxy groups. Example alkoxy groups include, but are not limited to, methoxy, ethoxy, propoxy (e.g., n-propoxy and isopropoxy), and t-butoxy. Similarly, "alkylthio" or "thioalkoxy" represents an alkyl group as defined above with the indicated number of carbon atoms attached through a sulphur bridge; for example methyl-S— and ethyl-S—.

"Halo" or "halogen" includes fluoro, chloro, bromo, and iodo. "Haloalkyl" is intended to include both branched and straight-chain saturated aliphatic hydrocarbon groups having the specified number of carbon atoms, substituted with one or more halogens. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with one or more fluorine atoms.

"Haloalkoxy" or "haloalkyloxy" represents a haloalkyl group as defined above with the indicated number of carbon atoms attached through an oxygen bridge. For example, "$C_1$ to $C_6$ haloalkoxy" or "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, and pentafluorothoxy. Similarly, "haloalkylthio" or "thiohaloalkoxy" represents a haloalkyl group as defined above with the indicated number of carbon atoms attached through a sulphur bridge; for example trifluoromethyl-S-, and pentafluoroethyl-S-.

The term "cycloalkyl" refers to cyclized alkyl groups, including mono-, bi- or poly-cyclic ring systems. "$C_3$ to $C_7$ cycloalkyl" or "$C_{3-7}$ cycloalkyl" is intended to include $C_3$, $C_4$, $C_5$, $C_6$, and $C_7$ cycloalkyl groups. Example cycloalkyl groups include, but are not limited to, cyclopropyl, cyclobutyl, cyclopentyl, cyclohexyl, and norbornyl. Branched cycloalkyl groups such as 1-methylcyclopropyl and 2-methylcyclopropyl are included in the definition of"cycloalkyl".

As used herein, "carbocycle", "carbocyclyl", or "carbocyclic residue" is intended to mean any stable 3-, 4-, 5-, 6-, 7-, or 8-membered monocyclic or bicyclic or 7-, 8-, 9-, 10-, 11-, 12-, or 13-membered bicyclic or tricyclic ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2]bicyclooctane). Preferred carbocycles, unless otherwise specified, are cyclopropyl, cyclobutyl, cyclopentyl, cyclohexyl, phenyl, indanyl, and tetrahydronaphthyl. When the term "carbocycle" is used, it is intended to include "aryl." A bridged ring occurs when one or more, preferably one to three, carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge.

As used herein, the term "bicyclic carbocycle" or "bicyclic carbocyclic group" is intended to mean a stable 9- or 10-membered carbocyclic ring system that contains two fused rings and consists of carbon atoms. Of the two fused rings, one ring is a benzo ring fused to a second ring; and the second ring is a 5- or 6-membered carbon ring which is saturated, partially unsaturated, or unsaturated. The bicyclic carbocyclic group may be attached to its pendant group at any carbon atom which results in a stable structure. The bicyclic carbocyclic group described herein may be substituted on any carbon if the resulting compound is stable. Examples of a bicyclic carbocyclic group are, but not limited to, naphthyl, 1,2-dihydronaphthyl, 1,2,3,4-tetrahydronaphthyl, and indanyl.

"Aryl" groups refer to monocyclic or polycyclic aromatic hydrocarbons, including, for example, phenyl, naphthyl, and phenanthranyl. Aryl moieties are well known and described, for example, in *Hawley's Condensed Chemical Dictionary* (15th ed.), R. J. Lewis, ed., J. Wiley & Sons, Inc., New York, 2007. "$C_6$ or $C_{10}$ aryl" or "$C_{6-10}$ aryl" refers to phenyl and naphthyl.

The term "benzyl", as used herein, refers to a methyl group on which one of the hydrogen atoms is replaced by a phenyl group.

As used herein, the term "heterocycle", "heterocyclyl", or "heterocyclic group" is intended to mean a stable 3-, 4-, 5-, 6-, or 7-membered monocyclic or bicyclic or 7-, 8-, 9-, 10-, 11-, 12-, 13-, or 14-membered polycyclic heterocyclic ring that is saturated, partially unsaturated, or fully unsaturated, and that contains carbon atoms and 1, 2, 3 or 4 heteroatoms independently selected from the group consisting of N, O and S; and including any polycyclic group in which any of the above-defined heterocyclic rings is fused to a benzene ring. The nitrogen and sulfur heteroatoms may optionally be oxidized (i.e., N→O and $S(O)_p$, wherein p is 0, 1 or 2). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle" is used, it is intended to include heteroaryl.

Examples of heterocycles include, but are not limited to, acridinyl, azetidinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, imidazolopyridinyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolopyridinyl, pyrazolyl, pyridazinyl, pyridooxazolyl, pyridoimidazolyl, pyridothiazolyl, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thiazolopyridinyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

Examples of 5- to 10-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl.

Examples of 5- to 6-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, and triazolyl. Also included are fused ring and spiro compounds containing, for example, the above heterocycles.

As used herein, the term "bicyclic heterocycle" or "bicyclic heterocyclic group" is intended to mean a stable 9- or 10-membered heterocyclic ring system which contains two fused rings and consists of carbon atoms and 1, 2, 3, or 4 heteroatoms independently selected from the group consisting of N, O and S. Of the two fused rings, one ring is a 5- or 6-membered monocyclic aromatic ring comprising a 5-membered heteroaryl ring, a 6-membered heteroaryl ring or a benzo ring, each fused to a second ring. The second ring is a 5- or 6-membered monocyclic ring which is saturated, partially unsaturated, or unsaturated, and comprises a 5-membered heterocycle, a 6-membered heterocycle or a carbocycle (provided the first ring is not benzo when the second ring is a carbocycle).

The bicyclic heterocyclic group may be attached to its pendant group at any heteroatom or carbon atom which results in a stable structure. The bicyclic heterocyclic group described herein may be substituted on carbon or on a nitrogen atom if the resulting compound is stable. It is preferred that when the total number of S and O atoms in the heterocycle exceeds 1, then these heteroatoms are not adjacent to one another. It is preferred that the total number of S and O atoms in the heterocycle is not more than 1.

Examples of a bicyclic heterocyclic group are, but not limited to, quinolinyl, isoquinolinyl, phthalazinyl, quinazolinyl, indolyl, isoindolyl, indolinyl, 1H-indazolyl, benzimidazolyl, 1,2,3,4-tetrahydroquinolinyl, 1,2,3,4-tetrahydroisoquinolinyl, 5,6,7,8-tetrahydro-quinolinyl, 2,3-dihydrobenzofuranyl, chromanyl, 1,2,3,4-tetrahydro-quinoxalinyl, and 1,2,3,4-tetrahydro-quinazolinyl.

As used herein, the term "aromatic heterocyclic group" or "heteroaryl" is intended to mean stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, and benzodioxane. Heteroaryl groups are substituted or unsubstituted. The nitrogen atom is substituted or unsubstituted (i.e., N or NR wherein R is H or another substituent, if defined). The nitrogen and sulfur heteroatoms may optionally be oxidized (i.e., N—O and S(O)$_p$, wherein p is 0, 1 or 2).

Examples of 5- to 6-membered heteroaryls include, but are not limited to, pyridinyl, furanyl, thienyl, pyrrolyl, pyrazolyl, pyrazinyl, imidazolyl, imidazolidinyl, tetrazolyl, isoxazolyl, oxazolyl, oxadiazolyl, oxazolidinyl, thiadiazinyl, thiadiazolyl, thiazolyl, triazinyl, and triazolyl.

Bridged rings are also included in the definition of heterocycle. A bridged ring occurs when one or more, preferably one to three, atoms (i.e., C, O, N, or S) link two non-adjacent carbon or nitrogen atoms. Examples of bridged rings include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

The term "counter ion" is used to represent a negatively charged species such as chloride, bromide, hydroxide, acetate, and sulfate or a positively charged species such as sodium (Na+), potassium (K+), ammonium ($R_nNH_m+$ where n=0-4 and m=0-4) and the like.

When a dotted ring is used within a ring structure, this indicates that the ring structure may be saturated, partially saturated or unsaturated.

As used herein, the term "amine protecting group" means any group known in the art of organic synthesis for the protection of amine groups which is stable to an ester reducing agent, a disubstituted hydrazine, R4-M and R7-M, a nucleophile, a hydrazine reducing agent, an activator, a strong base, a hindered amine base and a cyclizing agent. Such amine protecting groups fitting these criteria include those listed in Wuts, P. G. M. and Greene, T. W. *Protecting Groups in Organic Synthesis,* 4th Edition, Wiley (2007) and *The Peptides: Analysis. Synthesis. Biology,* Vol. 3, Academic Press, New York (1981), the disclosure of which is hereby incorporated by reference. Examples of amine protecting groups include, but are not limited to, the following: (1) acyl types such as formyl, trifluoroacetyl, phthalyl, and p-toluenesulfonyl; (2) aromatic carbamate types such as benzyloxycarbonyl (Cbz) and substituted benzyloxycarbonyls, 1-(p-biphenyl)-1-methylethoxycarbonyl, and 9-fluorenylmethyloxycarbonyl (Fmoc); (3) aliphatic carbamate types such as tert-butyloxycarbonyl (Boc), ethoxycarbonyl, diisopropylmethoxycarbonyl, and allyloxycarbonyl; (4) cyclic alkyl carbamate types such as cyclopentyloxycarbonyl and adamantyloxycarbonyl; (5) alkyl types such as triphenylmethyl and benzyl; (6) trialkylsilane such as trimethylsilane; (7) thiol containing types such as phenylthiocarbonyl and dithiasuccinoyl; and (8) alkyl types such as triphenylmethyl, methyl, and benzyl; and substituted alkyl types such as 2,2,2-trichloroethyl, 2-phenylethyl, and t-butyl; and trialkylsilane types such as trimethylsilane.

As referred to herein, the term "substituted" means that at least one hydrogen atom is replaced with a non-hydrogen group, provided that normal valencies are maintained and that the substitution results in a stable compound. When a substituent is keto (i.e., =O), then 2 hydrogens on the atom are replaced. Keto substituents are not present on aromatic moieties. When a ring system (e.g., carbocyclic or heterocyclic) is said to be substituted with a carbonyl group or a double bond, it is intended that the carbonyl group or double bond be part (i.e., within) of the ring. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative.

When any variable occurs more than one time in any constituent or formula for a compound, its definition at each occurrence is independent of its definition at every other occurrence. Thus, for example, if a group is shown to be substituted with 0-3 R groups, then said group may optionally be substituted with up to three R groups, and at each occurrence R is selected independently from the definition of R.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent.

Combinations of substituents and/or variables are permissible only if such combinations result in stable compounds.

As a person of ordinary skill in the art would be able to understand, a ketone (—CH—C=O) group in a molecule may tautomerize to its enol form (—C=C—OH). Thus, this disclosure is intended to cover all possible tautomers even when a structure depicts only one of them.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington: The Science and Practice of Pharmacy,* $22^{nd}$ Edition, Allen, L. V. Jr., Ed.; Pharmaceutical Press, London, UK (2012), the disclosure of which is hereby incorporated by reference.

In addition, compounds of the present invention may have prodrug forms. Any compound that will be converted in vivo to provide the bioactive agent (i.e., a compound of Formula (I) or Formula (II)) is a prodrug within the scope and spirit of the invention. Various forms of prodrugs are well known in the art. For examples of such prodrug derivatives, see:
- (a) Bundgaard, H., ed., *Design of Prodrugs,* Elsevier (1985), and Widder, K. et al., eds., *Methods in Enzymology,* 112:309-396, Academic Press (1985);
- b) Bundgaard, H., Chapter 5, "Design and Application of Prodrugs," *A Textbook of Drug Design and Development,* pp. 113-191, Krosgaard-Larsen, P. et al., eds., Harwood Academic Publishers (1991);
- c) Bundgaard, H., *Adv. Drug Deliv. Rev.,* 8:1-38 (1992);
- d) Bundgaard, H. et al., *J. Pharm. Sci.,* 77:285 (1988);
- e) Kakeya, N. et al., *Chem. Pharm. Bull.,* 32:692 (1984); and
- f) Rautio, J (Editor). *Prodrugs and Targeted Delivery (Methods and Principles in Medicinal Chemistry),* Vol 47, Wiley-VCH, 2011.

Compounds containing a carboxy group can form physiologically hydrolyzable esters that serve as prodrugs by being hydrolyzed in the body to yield Formula (I) or Formula (II) compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of Formula (I) or Formula (II) include $C_1$ to $C_6$ alkyl, $C_1$ to $C_6$ alkylbenzyl, 4-methoxybenzyl, indanyl, phthalyl, methoxymethyl, $C_{1-6}$ alkanoyloxy-$C_{1-6}$ alkyl (e.g., acetoxymethyl, pivaloyloxymethyl or propionyloxymethyl), $C_1$ to $C_6$ alkoxycarbonyloxy-$C_1$ to $C_6$ alkyl (e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl), and other well known physiologically hydrolyzable esters used, for example, in the penicillin and cephalosporin arts. Such esters may be prepared by conventional techniques known in the art.

Preparation of prodrugs is well known in the art and described in, for example, King, F. D., ed., *Medicinal Chemistry: Principles and Practice*, The Royal Society of Chemistry, Cambridge, UK ($2^{nd}$ edition, reproduced, 2006); Testa, B. et al., *Hydrolysis in Drug and Prodrug Metabolism. Chemistry Biochemistry and Enzymology*, VCHA and Wiley-VCH, Zurich, Switzerland (2003); Wermuth, C. G., ed., *The Practice of Medicinal Chemistry*, $3^{th}$ edition, Academic Press, San Diego, Calif. (2008).

The present invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds have a variety of potential uses, e.g., as standards and reagents in determining the ability of a potential pharmaceutical compound to bind to target proteins or receptors, or for imaging compounds of this invention bound to biological receptors in vivo or in vitro.

"Stable compound" and "stable structure" are meant to indicate a compound that is sufficiently robust to survive isolation to a useful degree of purity from a reaction mixture, and formulation into an efficacious therapeutic agent. It is preferred that compounds of the present invention do not contain a N-halo, $S(O)_2H$, or $S(O)H$ group.

The term "solvate" means a physical association of a compound of this invention with one or more solvent molecules, whether organic or inorganic. This physical association includes hydrogen bonding. In certain instances the solvate will be capable of isolation, for example when one or more, preferably one to three, solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

Abbreviations as used herein, are defined as follows: "1x" for once, "2x" for twice, "3x" for thrice, "° C." for degrees Celsius, "aq" for aqueous, "Col" for column, "eq" for equivalent or equivalents, "g" for gram or grams, "mg" for milligram or milligrams, "L" for liter or liters, "mL" for milliliter or milliliters, "μL" for microliter or microliters, "N" for normal, "M" for molar, "nM" for nanomolar, "mol" for mole or moles, "mmol" for millimole or millimoles, "min" for minute or minutes, "h" for hour or hours, "rt" for room temperature, "RT" for retention time, "ON" for overnight, "atm" for atmosphere, "psi" for pounds per square inch, "conc." for concentrate, "aq" for "aqueous", "sat" or "sat'd" for saturated, "MW" for molecular weight, "mw" or "μwave" for microwave, "mp" for melting point, "Wt" for weight, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "nOe" for nuclear Overhauser effect spectroscopy, "$^1H$" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

Ac: Acetic (AcOH: acetic acid, EtOAc: ethyl acetate)
ACN (or MeCN): acetonitrile
APF: aminophenyl fluorescein
BINAP: 2,2'-bis(diphenylphosphino)-1,1'-binaphthyl
Bn: benzyl
Boc: tert-butyl carbonyl
$Boc_2O$: Di-tert-butyl dicarbonate
Bu: butyl
dba ($Pd_2(dba)_3$): dibenzylideneacetone
DCM: dichloromethane
DEAD: diethyl azodicarboxylate
DIEA: diisopropylethylamine or Hunig's base
DMAP: 4-dimethylaminopyridine
DME: dimethoxyethane
DMF: dimethylformamide
DMSO: dimethyl sulfoxide
dppf ($PdCl_2(dppf)$): 1,1'-bis(diphenylphosphino)ferrocene
EDC: 1-Ethyl-3-(3-dimethylaminopropyl)carbodiimide
EPX: eosinophil peroxidase
Et: ethyl (EtOH: ethanol, EtOAc: ethyl acetate)
HATU: 2-(7-Aza-1H-benzotriazole-1-yl)-1,1,3,3-tetramethyluronium hexafluorophosphate
HBTU: 2-(1H-Benzotriazole-1-yl)-1,1,3,3-tetramethyluronium hexafluorophosphate
iBu: isobutyl
iPr: isopropyl
Me: methyl (MeOH: methanol, MeCN: acetonitrile)
MPO: myeloperoxidase
NMP: N-methylpyrrolidone
Ph: phenyl
Pr: propyl
Psig: gauge pressure in pounds per square inch
rt: room temperature
tBu: tert-butyl
T3P: propylphosphonic anhydride
TCA: trichloroacetic acid
TEA: triethylamine
TFA: trifluoroacetic acid
THF: tetrahydrofuran Ts: tosyl
Trt: trityl Synthesis The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent or solvent mixture appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

A particularly useful compendium of synthetic methods which may be applicable to the preparation of compounds of the present invention may be found in Larock, R. C., *Comprehensive Organic Transformations*, VCH Publishers, Inc., New York, N.Y. (1999). Preferred methods include, but are not limited to, those described below. All references cited herein are hereby incorporated in their entirety herein by reference.

It will also be recognized that another major consideration in the planning of any synthetic route in this field is the judicious choice of the protecting group used for protection of the reactive functional groups present in the compounds described in this invention. An authoritative account describing the many alternatives to the trained practitioner is Wuts, P. G. M. and Greene, T. W. *Protecting Groups in Organic Synthesis*, 4th Edition, Wiley (2007)).

Compounds having the general Formula (I):

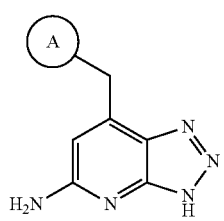

(I)

wherein A is defined above, can be prepared by the following one or more of the synthetic Schemes.

Schemes 1-5 describe synthetic routes for making intermediates and compounds of the present invention. Scheme 1 shows the formation of compounds of Formula (I) from the C-7 bromotriazolopyridine intermediate 1-1. Scheme 2 demonstrates the preparation of compounds of Formula (I) by processes analogous to that outlined in Scheme 1 where the sequence of steps have been reordered. Scheme 3 illustrates a general procedure for the elaboration of 4-alkyl-2,6-diaminopyridine intermediates 3-1 to compounds of Formula (I-III). Schemes 4 and 5 outline alternative preparations of diamine intermediates 3-1 which are then converted to compounds of Formula I via the processes outlined in Scheme 3.

Scheme 1 describes a preparation of compounds of Formula (I) of the present invention from the commercially available 4-bromo-2,6-diaminopyridine 1-1. Reaction mixture of 1-1 with freshly prepared 4-chlorophenyldiazonium chloride (adapted from Yao et al., *Arch. Pharm. Chem. Life Sci.*, 342:274 (2009)) either in an aqueous environment or a biphasic mixture of EtOAc and water from 0° C. to rt results in the preparation of diazine intermediate 1-2. This diazine intermediate is then reduced with either zinc and acetic acid in EtOH, or hydrazine-hydrochloride in EtOH. The resulting triamine intermediate 1-3 is treated with isoamylnitrite in THF, where acetic acid may or may not be added to increase reaction rate, to furnish bromotriazolopyridine intermediate 1-4. Compounds of Formula (I) were prepared from intermediate 1-4 via a Negishi cross-coupling reaction (Negishi, E.-i. in Chapter 1, *Metal-Catalyzed Cross-Coupling Reaction Mixtures*, Diederich, F. et al., eds., Wiley-VCH, New York (1998)) with a variety of either commercially available or freshly prepared (according to the general procedure outlined by Sher et al., *J. Comb. Chem.*, 7:99 (2005)) organozinc reagents under standard conditions (Netherton, M. R. et al., *Org. Lett.*, 3:4295 (2001)) using $Pd_2(dba)_3$, $tBu_3P\text{-}HBF_4$. Alternatively, intermediate 1-4 can be protected as a regioisomeric mixture of bis-tritylated compounds 1-5 prior to the Negishi cross-coupling, which yields intermediate 1-6, followed by removal of the protecting groups to furnish compounds of Formula (I).

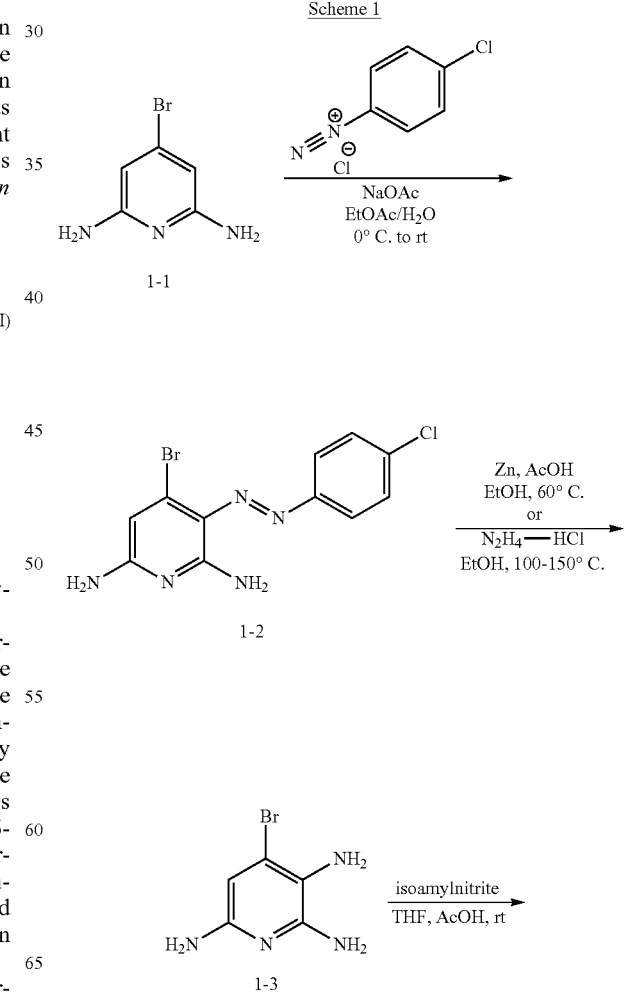

-continued

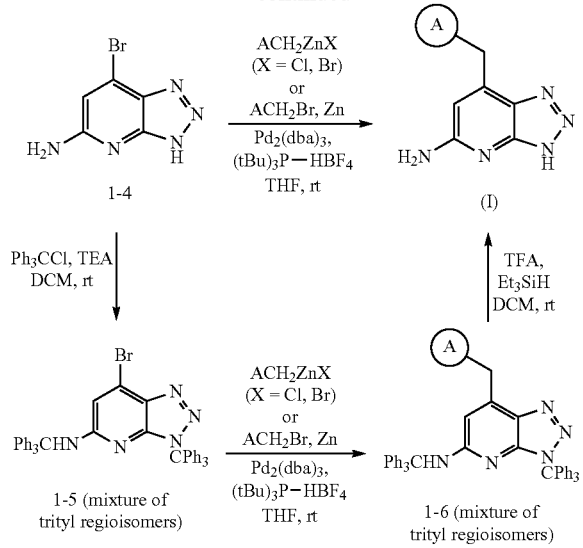

Alternatively Scheme 2 illustrates how the steps from Scheme 1 can be reordered to produce compounds of Formula (I) by moving the Neghishi cross-coupling reaction mixture sequence earlier in the process.

Scheme 3 outlines a general procedure for the elaboration of C-7 substituted 2,6-diaminopyridines 3-1 (syntheses of which are described in Schemes 4-5) to compounds of Formula (I) via diazotization with 4-chlorophenyldiazonium chloride (adapted from Yao et al., *Arch. Pharm. Chem. Life Sci.*, 342:274 (2009)). The resulting diazine intermediates 3-2 were then reduced either with zinc/acetic acid or hydrazine to furnish triamine intermediates 3-3. These triamine intermediates were then cyclized by treatment with isoamylnitrite in THF, where acetic acid may or may not be added to increase reaction rate, to furnish compounds of Formula (I).

Scheme 3

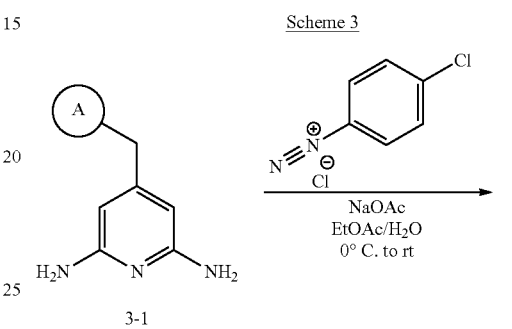

Scheme 2

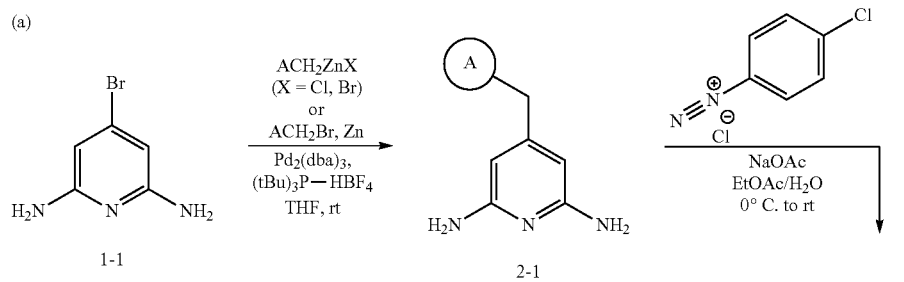

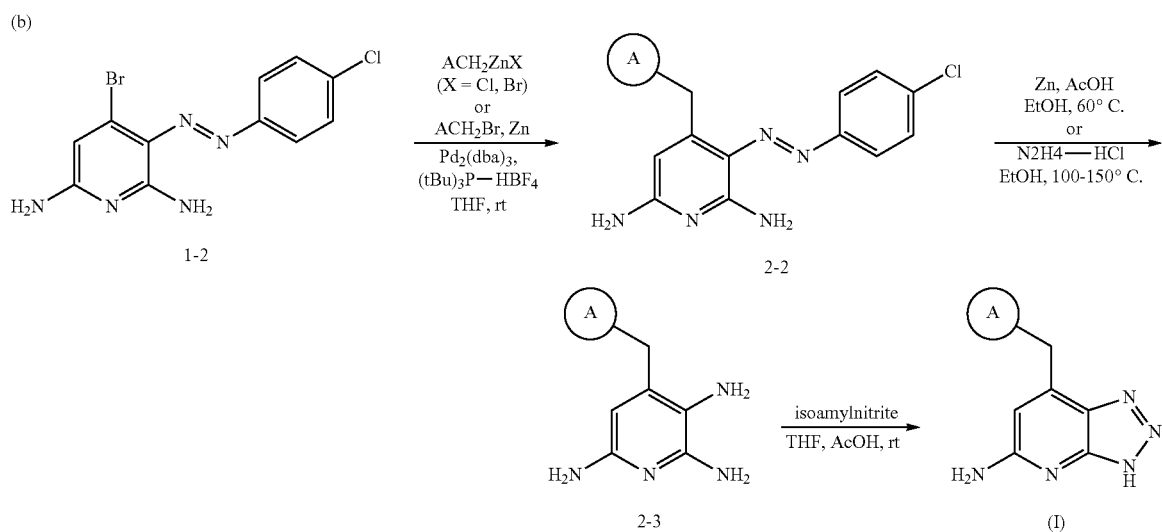

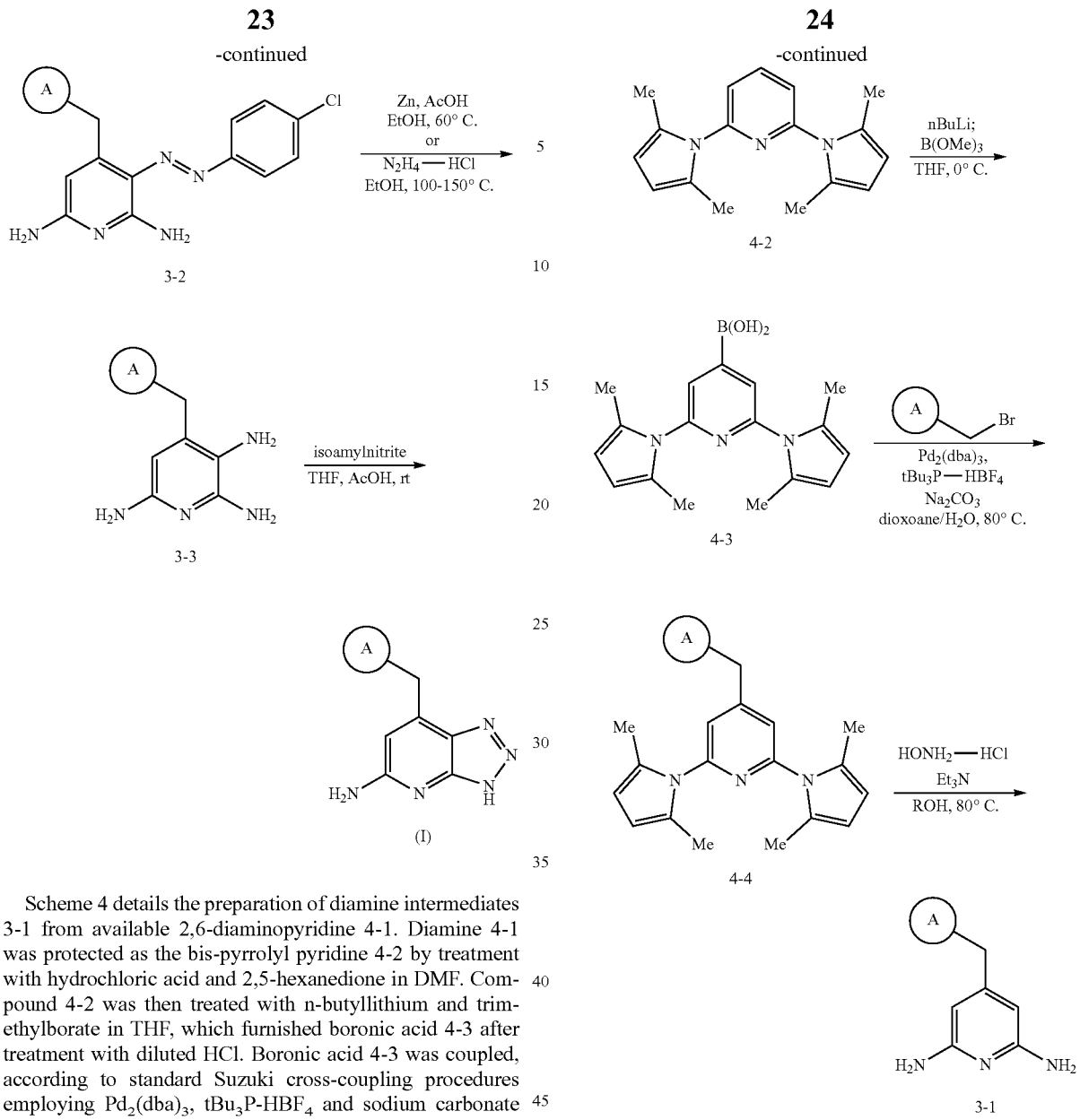

Scheme 4 details the preparation of diamine intermediates 3-1 from available 2,6-diaminopyridine 4-1. Diamine 4-1 was protected as the bis-pyrrolyl pyridine 4-2 by treatment with hydrochloric acid and 2,5-hexanedione in DMF. Compound 4-2 was then treated with n-butyllithium and trimethylborate in THF, which furnished boronic acid 4-3 after treatment with diluted HCl. Boronic acid 4-3 was coupled, according to standard Suzuki cross-coupling procedures employing Pd$_2$(dba)$_3$, tBu$_3$P-HBF$_4$ and sodium carbonate solution, to either commercially available benzyl halides or benzyl halides which can be prepared from the corresponding alcohols according to standard procedures (Kanamathareddy, S. et al., *J. Org. Chem.,* 61:2511 (1996)). Treatment of intermediate 4-4 with hydroxylamine hydrochloride and Et$_3$N in an alcoholic solvent, where water may or may not be added as a cosolvent, results in the formation of key diamine intermediate 3-1.

Scheme 5 illustrates an alternative synthesis of key diamine intermediate 3-1 from 4-bromo-2,6-diaminopyridine 1-1 or 2,6-diaminopyridine 4-1. The starting diamines 1-1 or 4-1 were treated with HBr (where X=Br) or HCl (where X=H) and 2,5-hexanedione in DMF to furnish protected pyridines 5-1 or 4-2, respectively. Lithiation of intermediates 5-1 or 4-2 followed by trapping with an aldehyde results in the formation of secondary alcohol 5-2. Use of the des-bromo analog 4-2 may result in the formation of varying levels of regioisomeric 3-pyridyl product. Treatment of secondary alcohol 5-2 with acetic anhydride, DMAP and pyridine results in the formation of ester 5-3. Subjecting ester 5-3 to samarium iodide in the presence of an alcoholic additive such as tert-butanol or isopropanol results in the formation of intermediate 4-4. Treatment of intermediate 4-4 with hydroxylamine hydrochloride and Et$_3$N in an alcoholic solvent, where water may or may not be added as a cosolvent, results in the formation of key diamine intermediate 3-1.

Scheme 5

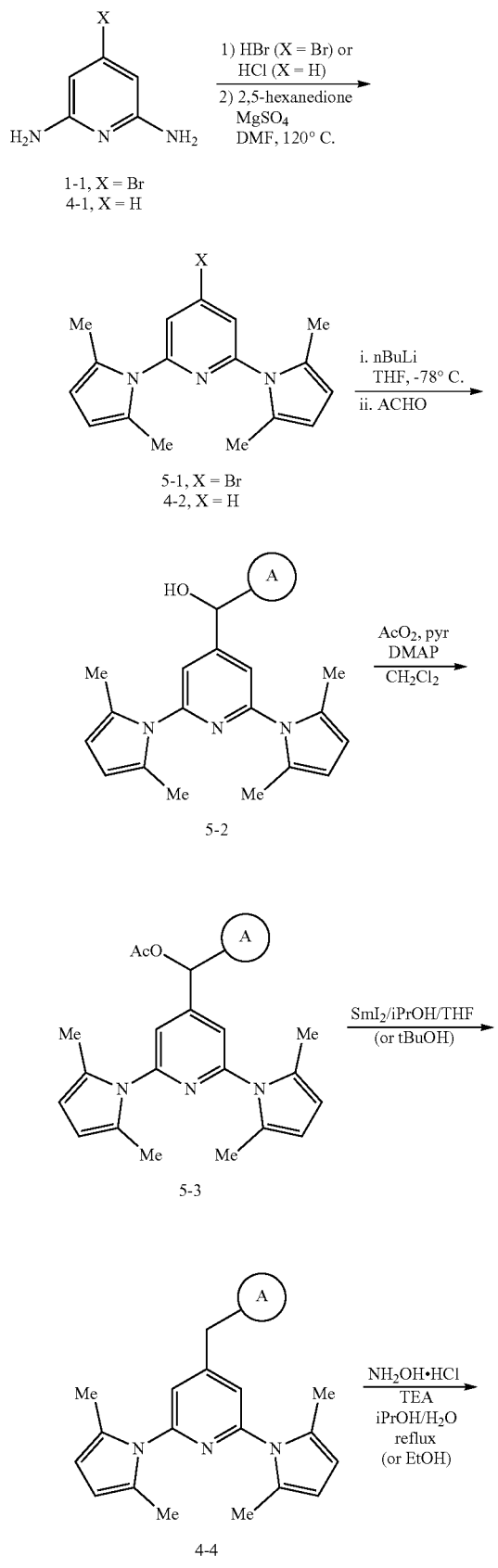

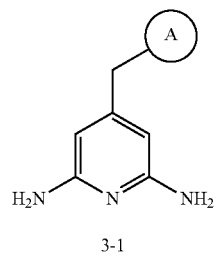

General Methods

The following methods were used in the exemplified Examples, except where noted otherwise.

Purification of intermediates and final products was carried out via either normal or reverse phase chromatography. Normal phase chromatography was carried out using pre-packed $SiO_2$ cartridges eluting with either gradients of hexanes and ethyl acetate or DCM and MeOH unless otherwise indicated. For highly polar amines, gradients of DCM and 1M $NH_3$ in MeOH were used. Reverse phase preparative HPLC was carried out using C18 columns with UV 220 nm or prep LCMS detection eluting with gradients of Solvent A (90% water, 10% MeOH, 0.1% TFA) and Solvent B (10% water, 90% MeOH, 0.1% TFA) or with gradients of Solvent A (90% water, 10% ACN, 0.1% TFA) and Solvent B (10% water, 90% ACN, 0.1% TFA) or with gradients of Solvent A (95% water, 2% ACN, 0.1% HCOOH) and Solvent B (98% ACN, 2% water, 0.1% HCOOH) or with gradients of Solvent A (95% water, 5% ACN, 10 mM $NH_4OAc$) and Solvent B (98% ACN, 5% water, 10 mM $NH_4OAc$) or with gradients of Solvent A (95% water, 2% ACN, 0.1% $NH_4OH$) and Solvent B (98% ACN, 2% water, 0.1% $NH_4OH$).

Analytical HPLC: Methods Employed in Characterization of Examples

Products were analyzed by reverse phase analytical HPLC: carried out on a Shimadzu Analytical HPLC: system running Discovery VP software. RT=retention time.

Method A: Linear gradient of 0 to 100% B over 10 min, with 5 min hold at 100% B;
 UV visualization at 254 nm
 Column: SunFire C18; 3.5 µm; 4.6×150 mm
 Flow rate: 1 mL/min (Method A).
 Solvent A: 10% acetonitrile, 90% water, 0.05% TFA
 Solvent B: 10% water, 90% acetonitrile, 0.05% TFA Method B: Linear gradient of 0 to 100% B over 10 min, with 5 min hold at 100% B;
 UV visualization at 254 nm
 Column: XBridge Phenyl 3.5 um; 4.6×150 mm
 Flow rate: 1 mL/min (Method A).
 Solvent A: 10% acetonitrile, 90% water, 0.05% TFA
 Solvent B: 10% water, 90% acetonitrile, 0.05% TFA Method C: Linear gradient: 0-100% B over 3 min, then a 0.75-min hold at 100% B
 Temperature: 50° C.
 UV visualization at 220 nm
 Column: Waters Acquity UPLC BEH C18, 1.7 µm; 2.1×50 mm
 Flow: 1.11 mL/min (Method A).
 Solvent A: 5:95 acetonitrile:water with 0.1% TFA
 Solvent B: 95:5 acetonitrile:water with 0.1% TFA Method D: Linear gradient: 0-100% B over 3 min, then a 0.75-min hold at 100% B
 Temperature: 50° C.

UV visualization at 220 nm
Column: Waters Acquity UPLC BEH C18, 1.7 µm; 2.1×50 mm
Flow: 1.11 mL/min (Method A).
Solvent A: 5:95 acetonitrile:water with 10 mM ammonium acetate
Solvent B: 95:5 acetonitrile:water with 10 mM ammonium acetate
Method E: Linear Gradient: 0.5 min hold at 0% B, 0-100% B over 4 minutes, then a
0.5-min hold at 100% B
Column: Waters BEH C18, 2.0×50 mm, 1.7-µm particles
Temperature: 40° C.;
Flow: 1 mL/min
Solvent A: 5:95 acetonitrile:water with 10 mM ammonium acetate
Solvent B: 95:5 acetonitrile:water with 10 mM ammonium acetate
LC/MS Methods Employed in Characterization of Examples
Reverse phase analytical HPLC/MS was performed on Shimadzu LC10AS systems coupled with Waters ZMD Mass Spectrometers (Methods A-E) or Waters Acquity system coupled with a Waters MICROMASS® ZQ Mass Spectrometer (Method F).
Method A: Linear gradient of 0 to 100% B over 4 min, with 1 min hold at 100% B;
UV visualization at 220 nm
Column: PHENOMENEX® Luna C18 4.6×50 mm
Flow rate: 4 mL/min (Method A).
Solvent A: 0.1% trifluoroacetic acid, 90% water, 10% acetonitrile
Solvent B: 0.1% trifluoroacetic acid, 90% acetonitrile, 10% water.
Method B: Linear gradient of 0 to 100% B over 4 min, with 1 min hold at 100% B;
UV visualization at 220 nm
Column: PHENOMENEX® Luna C18 2×50 mm
Flow rate: 4 mL/min (Method A).
Solvent A: 98% water, 2% methanol, 0.1% formic acid
Solvent B: Methanol, 0.1% formic acid.
Method C: Linear gradient of 0 to 100% B over 4 min, with 1 min hold at 100% B;
UV visualization at 220 nm
Column: PHENOMENEX® Luna C18 4.6×50 mm
Flow rate: 4 mL/min (Method A).
Solvent A: 0.1% trifluoroacetic acid, 90% water, 10% methanol
Solvent B: 0.1% trifluoroacetic acid, 90% methanol, 10% water.
Method D: Linear gradient of 0 to 100% B over 2 min, with 1 min hold at 100% B;
UV visualization at 220 nm
Column: PHENOMENEX® Luna C18 2.0×30 mm
Flow rate: 1 mL/min (Method A).
Solvent A: 0.1% trifluoroacetic acid, 90% water, 10% methanol
Solvent B: 0.1% trifluoroacetic acid, 90% methanol, 10% water.
Method E: Linear gradient of 0 to 100% B over 2 min, with 1 min hold at 100% B;
UV visualization at 220 nm
Column: PHENOMENEX® Luna C18 2.0×30 mm
Flow rate: 1 mL/min (Method A).
Solvent A: 98% water, 2% methanol, 0.1% formic acid
Solvent B: Methanol, 0.1% formic acid.
Method F: Linear gradient of 2 to 98% B over 1 min, with 0.5 min hold time at 98% B;
UV visualization at 220 nm
Column: Waters BEH C18 2.1×50 mm
Flow rate: 0.8 mL/min (Method A).
Solvent A: 0.05% TFA, 100% water
Solvent B: 0.05% TFA, 100% acetonitrile
Preparative HPLC: Methods Employed in the Purification of Products
Method G: Linear gradient of 20 to 100% B over 10 min, with 2 min hold time at 100% B
Shimadzu LC-8A binary pumps
Shimadzu SPD-10 A or 20A UV detector
UV visualization at 220 nm
Column: Waters SunFire 19×100 mm 5 µm C18
Flow rate: 20 mL/min (Method A).
Solvent A: 0.1% TFA, 10% MeOH, 90% water
Solvent B: 0.1% TFA, 90% MeOH, 10% water
Method J: Linear gradient of 20 to 100% B over 10 min, with 2 min hold time at 100% B
Shimadzu LC-8A binary pumps
Shimadzu SPD-10A or 20A UV detector
UV visualization at 220 nm
Column: PHENOMENEX® Luna Axia 30×100 mm 5 µm C18
Flow rate: 20 mL/min (Method A).
Peak collection triggered by UV absorbance
Solvent A: 0.1% TFA, 10% MeOH, 90% water
Solvent B: 0.1% TFA, 90% MeOH, 10% water
Method K: Linear gradient of 0 to 100% B over 10 min, with 2 min hold time at 100% B
Shimadzu LC-8A binary pumps
Shimadzu SPD-20A UV detector
UV visualization at 220 nm
Column: PHENOMENEX® Luna Axia 30×75 mm 5 µm C18
Flow rate: 20 mL/min (Method A).
Peak collection triggered by UV absorbance
Solvent A: 0.1% TFA, 10% ACN, 90% water
Solvent B: 0.1% TFA, 90% ACN, 10% water
NMR Employed in Characterization of Examples
$^1$H NMR spectra were obtained with Bruker or JEOL® Fourier transform spectrometers operating at frequencies as follows: $^1$H NMR: 400 MHz (Bruker or JEOL®) or 500 MHz (Bruker or JEOL®). $^{13}$C NMR: 100 MHz (Bruker or JEOL®). Spectra data are reported in the format: chemical shift (multiplicity, coupling constants, number of hydrogens). Chemical shifts are specified in ppm downfield of a tetramethylsilane internal standard (8 units, tetramethylsilane=0 ppm) and/or referenced to solvent peaks, which in $^1$H NMR spectra appear at 2.49 ppm for $CD_2HSOCD_3$, 3.30 ppm for $CD_2HOD$, 1.94 for $CD_3CN$, and 7.24 ppm for $CHCl_3$, and which in $^{13}$C NMR spectra appear at 39.7 ppm for $CD_3SOCD_3$, 49.0 ppm for $CD_3OD$, and 77.0 ppm for $CDCl_3$.

IV. Biology

Myeloperoxidase (MPO) and eosinophil peroxidase (EPX) are heme-containing enzymes and are members of the family of mammalian heme peroxidases that also includes salivary peroxidase, lactoperoxidase (LPO), thyroid peroxidase (TPO), prostaglandin H synthase and others. Both MPO and EPX use hydrogen peroxide to oxidize an array of substrates to either hypohalous acids or free radicals. Whereas both EPX and MPO are able to oxidize bromine (Br⁻), iodine (I⁻) and thiocyanate (⁻SCN), MPO is also able to oxidize chloride (Cl⁻) to hypochlorous acid (HOCl) efficiently.

MPO is present predominantly in neutrophils and to a lesser extent in monocytes and subtypes of tissue macrophages. The processed mature form of the enzyme is a glycosylated 146 kDa homodimer. Each subunit is made of a light and heavy polypeptide chain and contains a protoporphyrin IX group with a central iron. The three-fold linkage of the heme is unique compared to other heme proteins and provides specific spectral and catalytic properties to MPO. MPO uses hydrogen peroxide to oxidize an array of substrates to either hypohalous acids or free radicals. The main substrate for MPO is generally accepted to be chloride, which is oxidized to hypochlorous acid. This is one of the most reactive oxidants produced in vivo. Other substrates include thiocyanate, bromide, tyrosine, tryptophan, sulfhydryls, phenol and indole derivatives, ascorbate, nitrite, nitric oxide, and urate.

The physiological role of MPO is to participate in the killing of invading bacterial and fungal pathogens (Klebanoff, S. J., *J. Exp Med.*, 126:1063-1078 (1967); Klebanoff, S. J., *J. Bacteriol.*, 95:2131-2138 (1968); Klebanoff, S. J., *Science*, 169:1095-1097 (1970)). However, excessive generation of oxidants by MPO and other peroxidases has been linked to tissue damage in many diseases, especially those characterized by acute or chronic inflammation. At sites of inflammation, PMNs or tissue macrophages can generate hydrogen peroxide and upon activation also produce myeloperoxidase. This is evidenced by the fact that, in many cases, enzymatically active MPO in conjunction with 3-chlorotyrosine, a tissue marker for HOCl-mediated damage, or HOCl-modified proteins can be detected in diseased tissues colocalized with neutrophils or macrophages (Daugherty, A. et al., *JCI*, 94:437-444 (1994); Bergt et al., *Proc. Natl. Acad. Sci.*, 101:13032-13037 (2004); Pennathur, S. et al., *JBC*, 279:42977-42983 (2004); Choi, D. K. et al., *J. Neurosci.*, 25(28):6394-6600 (2005)).

Eosinophil peroxidase (EPX) is a cationic heme-containing protein, and represents nearly 25% of the total mass of the secondary granule protein in eosinophils. It is a highly basic 77 kDa protein made up of two subunits containing a modified Fe-protoporphyrin-IX prosthetic group. EPX shares with MPO the ability to use $H_2O_2$ to oxidize thiocyanate, bromide, and nitrite in vivo to kill bacteria, and viruses (Jong, E. C. et al., *J. Immunol.*, 124:1949-1953 (1980)). Eosinophils play a unique role in host defense mechanisms but increased levels of circulating and tissue eosinophils are implicated in promoting cellular and tissue injury in particular in asthma, and during allergic inflammatory responses of lung diseases.

MPO Peroxidation Assay (Amplex Red Assay)

MPO peroxidation activity was measured in 100 mM KPi (pH 7.4) by utilizing the non-fluorescent reagent Amplex Red (Invitrogen catalog # A12222) which can be oxidized to the highly fluorescent resorufin. Amplex Red is oxidized by the peroxidase action of MPO to resorufin. Reactions were carried out in 50 µL total volume by adding a 25 µL mixture of 200 pM myeloperoxidase and 40 nM $H_2O_2$ (Sigma #349887) to 100 nL inhibitor in 100% DMSO in a 384 well Perkin Elmer Optiplate. Enzyme and compound were preincubated for ten minutes at room temperature.

After the ten minute preincubation, 25 µL of an Amplex Red mixture containing 200 µM Amplex Red and 10 mM $H_2O_2$ was added to the plate. Kinetic determinations were carried out immediately on a Perkin Elmer Envision (15 minute kinetic read, Ex: 535 nm, Em: 590 nm).

$IC_{50}$ values were calculated by determining the slope of the linear portion of the kinetic trace (180-540 secs), and using that calculated slope to determine % inhibition occurring at each concentration of inhibitor using the following equation:

$$Y = A + \frac{B - A}{1 + (C/x)^D}$$

where A=minimal Y value (activity level of inhibited sample), B=maximal Y value (activity level of uninhibited sample), C=Log $IC_{50}$, D=Hill Slope, x=concentration of inhibitor.

MPO Chlorination Assay (APF Assay)

MPO chlorination activity was measured in 100 mM KPi (pH 7.4) by utilizing the non-fluorescent reagent Aminophenyl fluorescein (APF, Invitrogen catalog #A36003). APF is cleaved by (—OCl) to yield the fluorescent compound fluorescein. Reactions were carried out in 50 µL total volume by adding a 25 µL mixture of 200 pM myeloperoxidase and 120 mM NaCl to 100 nL inhibitor in 100% DMSO in a 384 well, non-binding surface clear bottom plate (CORNING® #3655). Enzyme, inhibitor, and chloride were preincubated for ten minutes at room temperature.

After the ten minute preincubation, 25 µL of an APF mixture containing 10 mM APF, 120 mM NaCl and 10 µM $H_2O_2$ was added to the plate using the internal dispensing system of a Hammatsu FDSS 6000. Kinetic determinations were carried out immediately on the FDSS 6000 (3 minute kinetic read, 1 read every second, ex: 485 nm, em: 535 nm). $IC_{50}$ values for inhibitors were calculated by taking the slope of the linear portion of the kinetic measurement (20 seconds to ~80-120 secs).

$IC_{50}$ values were calculated by determining the slope of the linear portion of the kinetic trace (180-540 secs), and using that calculated slope to determine % inhibition occurring at each concentration of inhibitor using the following equation:

$$Y = A + \frac{B - A}{1 + (C/x)^D}$$

where A=minimal Y value (activity level of inhibited sample), B=maximal Y value (activity level of uninhibited sample), C=Log $IC_{50}$, D=Hill Slope, x=concentration of inhibitor.

EPX Bromination Assay

EPX bromination activity was measured in 100 mM KPi (pH 7.4) by monitoring the $H_2O_2$ catalyzed formation of 3-bromo tyrosine from tyrosine and potassium bromide. A 50 µl mixture of 0.6 µM EPX (Lee Biosolutions Cat#342-60) was added to 100 nL inhibitor in 100% DMSO in a 384 well REMP plate. Enzyme and compound were preincubated for ten minutes at room temperature.

After the ten minute preincubation of enzyme and inhibitor, 25 µL of a mixture containing 400 µM tyrosine and 1200 µM potassium bromide was added to the plate containing enzyme and inhibitor, followed by the addition of 25 µl of 20 µM $H_2O_2$. The reaction was allowed to proceed for 15 minutes, at which time it was quenched with 10 µL of 20% TCA. The final concentrations of all components were 0.3 µM EPX, 100 µM tyrosine, 400 µM potassium bromide, 5 µM $H_2O_2$, 0.1% DMSO, 2.0% TCA.

IC$_{50}$ values were determined by determining the peak areas of 3-bromo-tyrosine present at the end of the 15 minute reaction and fitting the data to:

$$Y = A + \frac{B-A}{1+(C/x)^D}$$

where A=minimal Y value (activity level of inhibited sample), B=maximal Y value (activity level of uninhibited sample), C=Log IC$_{50}$, D=Hill Slope, x=concentration of inhibitor.

Reversed-phase analysis was performed on a Waters Acquity Ultra Performance LC system using an Acquity UPLC BEH C$_{18}$ 1.7 µM, 2.1×50 mm analytical column. The column was maintained at 60° C. Samples were eluted using a gradient of 0%-100% B over 2.5 minutes, followed by equilibration with 100% A for 1 minute where A consisted of 0.1% TFA and B consisted of 90% MeOH/0.1% TFA at a flow rate of 0.6 ml/min. The retention time of 3-bromo tyrosine was 1.22 min.

Many of the exemplified Examples disclosed below were tested in the MPO chlorination assay described above and found having MPO inhibitory activity. A range of IC$_{50}$ values of ≤10 µM (10000 nM) was observed.

The exemplified Examples disclosed below were tested in the MPO peroxidation assay described above and found to having MPO inhibitory activity. A range of IC$_{50}$ values of ≤10 µM (10000 nM) was observed.

Some compounds of the invention were tested in the EPX bromination assay described above and were found to inhibit EPX with a range of IC$_{50}$ values of ≤10 µM (10000 nM), as demonstrated by Example 31 (EPX IC$_{50}$=0.034 µM), Example 57 (EPX IC$_{50}$=0.052 µM), and Example 64 (EPX IC$_{50}$=0.019 µM).

Table 1 below lists IC$_{50}$ value range in the MPO peroxidation (Amplex Red) assay and MPO chlorination assay (APF) measured for the following Examples. Potency ranges A 1-100 nM; B=101-999 nM; C=1000-10000 nM.

TABLE 1

| Example No. | APF Assay IC$_{50}$ value (µM) | Amplex Red Assay IC$_{50}$ value (µM) |
|---|---|---|
| 1 | A | A |
| 2 | — | A |
| 3 | — | B |
| 4 | — | B |
| 5 | — | B |
| 6 | — | B |
| 7 | — | A |
| 8 | — | A |
| 9 | — | A |
| 10 | — | B |
| 11 | B | B |
| 12 | — | B |
| 13 | C | C |
| 14 | A | B |
| 15 | — | B |
| 16 | A | A |
| 17 | — | A |
| 18 | — | A |
| 19 | — | B |
| 20 | — | B |
| 21 | A | A |
| 22 | — | B |
| 23 | — | A |
| 24 | — | A |
| 25 | — | A |
| 26 | — | C |
| 27 | — | B |
| 28 | B | B |
| 29 | B | B |
| 30 | B | A |
| 31 | B | A |
| 32 | — | B |
| 33 | — | A |
| 34 | B | B |
| 35 | — | B |
| 36 | — | C |
| 37 | B | B |
| 38 | — | B |
| 39 | — | B |
| 40 | B | B |
| 41 | — | B |
| 42 | — | A |
| 43 | B | B |
| 44 | B | A |
| 45 | — | A |
| 46 | — | B |
| 47 | B | B |
| 48 | B | A |
| 49 | — | B |
| 50 | B | B |
| 51 | C | B |
| 52 | — | B |
| 53 | — | B |
| 54 | — | B |
| 55 | — | B |
| 56 | B | B |
| 57 | — | A |
| 58 | B | C |
| 59 | — | A |
| 60 | — | B |
| 61 | — | A |
| 62 | A | A |
| 63 | A | A |
| 64 | B | A |
| 65 | A | A |
| 66 | B | B |
| 67 | — | B |
| 68 | — | B |

Accordingly, the compounds of the present invention may be administered to mammals, preferably humans, for the treatment of a variety of conditions and disorders, including, but not limited to, atherosclerosis, coronary artery disease, acute coronary syndrome, dyslipidemias and the sequelae thereof, angina, ischemia, cardiac ischemia, myocardial infarction, reperfusion injury, angioplastic restenosis, hypertension, vascular complications of diabetes, obesity or endotoxemia, heart failure, lung diseases including asthma, COPD and cystic fibrosis, and neuroinflammatory diseases, including multiple sclerosis, Alzheimer's disease, Parkinson's disease, multiple system atrophy, and stroke, as well as chronic inflammatory diseases such as inflammatory bowel disease, renal glomerular damage and rheumatoid arthritis.

V. Pharmaceutical Compositions, Formulations and Combinations

The compounds of this invention can be administered for any of the uses described herein by any suitable means, for example, orally, such as tablets, capsules (each of which includes sustained release or timed release formulations), pills, powders, granules, elixirs, tinctures, suspensions (including nanosuspensions, microsuspensions, spray-dried dispersions), syrups, and emulsions; sublingually; bucally; parenterally, such as by subcutaneous, intravenous, intramuscular, or intrasternal injection, or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories. They can be administered alone, but generally will be administered with a pharmaceutical carrier selected on the basis of the chosen route of administration and standard pharmaceutical practice.

The term "pharmaceutical composition" means a composition comprising a compound of the invention in combination with at least one additional pharmaceutically acceptable carrier. A "pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, anti-bacterial agents, anti-fungal agents, lubricating agents and dispensing agents, depending on the nature of the mode of administration and dosage forms.

Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, Allen, L. V. Jr. et al. *Remington: The Science and Practice of Pharmacy* (2 Volumes), 22nd Edition (2012), Pharmaceutical Press.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired.

By way of general guidance, the daily oral dosage of each active ingredient, when used for the indicated effects, will range between about 0.01 to about 5000 mg per day, preferably between about 0.1 to about 1000 mg per day, and most preferably between about 0.1 to about 250 mg per day. Intravenously, the most preferred doses will range from about 0.01 to about 10 mg/kg/minute during a constant rate infusion. Compounds of this invention may be administered in a single daily dose, or the total daily dosage may be administered in divided doses of two, three, or four times daily.

The compounds are typically administered in admixture with suitable pharmaceutical diluents, excipients, or carriers (collectively referred to herein as pharmaceutical carriers) suitably selected with respect to the intended form of administration, e.g., oral tablets, capsules, elixirs, and syrups, and consistent with conventional pharmaceutical practices.

Dosage forms (pharmaceutical compositions) suitable for administration may contain from about 1 milligram to about 2000 milligrams of active ingredient per dosage unit. In these pharmaceutical compositions the active ingredient will ordinarily be present in an amount of about 0.1-95% by weight based on the total weight of the composition.

A typical capsule for oral administration contains at least one of the compounds of the present invention (250 mg), lactose (75 mg), and magnesium stearate (15 mg). The mixture is passed through a 60 mesh sieve and packed into a No. 1 gelatin capsule.

A typical injectable preparation is produced by aseptically placing at least one of the compounds of the present invention (250 mg) into a vial, aseptically freeze-drying and sealing. For use, the contents of the vial are mixed with 2 mL of physiological saline, to produce an injectable preparation.

The present invention includes within its scope pharmaceutical compositions comprising, as an active ingredient, a therapeutically effective amount of at least one of the compounds of the present invention, alone or in combination with a pharmaceutical carrier. Optionally, compounds of the present invention can be used alone, in combination with other compounds of the invention, or in combination with one or more, preferably one to three, other therapeutic agent(s), e.g., HMG-CoA reductase inhibitors, antihypertensives or other pharmaceutically active material.

The compounds of the present invention may be employed in combination with other suitable therapeutic agents useful in the treatment of the aforementioned diseases or disorders including: anti-atherosclerotic agents, anti-dyslipidemic agents, anti-diabetic agents, anti-hyperglycemic agents, anti-hyperinsulinemic agents, anti-thrombotic agents, anti-retinopathic agents, anti-neuropathic agents, anti-nephropathic agents, anti-ischemic agents, anti-hypertensive agents, anti-obesity agents, anti-hyperlipidemic agents, anti-hypertriglyceridemic agents, anti-hypercholesterolemic agents, anti-restenotic agents, anti-pancreatic agents, lipid lowering agents, anorectic agents, memory enhancing agents, anti-dementia agents, cognition promoting agents, appetite suppressants, agents for treating heart failure, agents for treating peripheral arterial disease, agents for treating malignant tumors, and anti-inflammatory agents.

The compounds of the present invention may be employed in combination with additional therapeutic agent(s) selected from one or more, preferably one to three, of the following therapeutic agents in treating atherosclerosis: anti-hyperlipidemic agents, plasma HDL-raising agents, anti-hypercholesterolemic agents, cholesterol biosynthesis inhibitors (such as HMG CoA reductase inhibitors), LXR agonist, probucol, raloxifene, nicotinic acid, niacinamide, cholesterol absorption inhibitors, bile acid sequestrants (such as anion exchange resins, or quaternary amines (e.g., cholestyramine or colestipol)), low density lipoprotein receptor inducers, clofibrate, fenofibrate, benzofibrate, cipofibrate, gemfibrizol, vitamin $B_6$, vitamin $B_{12}$, anti-oxidant vitamins, f-blockers, anti-diabetes agents, angiotensin II antagonists, angiotensin converting enzyme inhibitors, platelet aggregation inhibitors, fibrinogen receptor antagonists, aspirin and fibric acid derivatives.

The compounds of the present invention may be employed in combination with additional therapeutic agent(s) selected from one or more, preferably one to three, of the following therapeutic agents in treating cholesterol biosynthesis inhibitor, particularly an HMG-CoA reductase inhibitor. Examples of suitable HMG-CoA reductase inhibitors include, but are not limited to, lovastatin, simvastatin, pravastatin, fluvastatin, atorvastatin, and rosuvastatin.

The term HMG-CoA reductase inhibitor is intended to include all pharmaceutically acceptable salt, ester, free acid and lactone forms of compounds which have HMG-CoA reductase inhibitory activity and, therefore, the use of such salts, esters, free acids and lactone forms is included within the scope of this invention. Compounds which have inhibitory activity for HMG-CoA reductase can be readily identified using assays well-known in the art.

The compounds of the invention may be used in combination with one or more, preferably one to three, of the following anti-diabetic agents depending on the desired target therapy. Studies indicate that diabetes and hyperlipidemia modulation can be further improved by the addition of a second agent to the therapeutic regimen. Examples of anti-diabetic agents include, but are not limited to, sulfonylureas (such as chlorpropamide, tolbutamide, acetohexamide, tolazamide, glyburide, gliclazide, glynase, glimepiride, and glipizide), biguanides (such as metformin), thiazolidinediones (such as ciglitazone, pioglitazone, troglitazone, and rosiglitazone), and related insulin sensitizers, such as selective and non-selective activators of PPARα, PPARβ and PPARγ, dehydroepiandrosterone (also referred to as DHEA or its conjugated sulphate ester, DHEA-SO$_4$); anti-glucocorticoids; TNFα ☐inhibitors; dipeptidyl peptidase IV (DPP4) inhibitor (such as sitagliptin, saxagliptin), GLP-1 agonists or analogs (such as exenatide), α-glucosidase inhibitors (such as acarbose, miglitol, and voglibose), pramlintide (a synthetic analog of the human hormone amylin), other insulin secretagogues (such as repaglinide, gliquidone, and nateglinide), insulin, as well as the therapeutic agents discussed above for treating atherosclerosis.

The compounds of the invention may be used in combination with one or more, preferably one to three, of the following anti-obesity agents selected from phenylpropanolamine, phentermine, diethylpropion, mazindol, fenfluramine, dexfenfluramine, phentiramine, β$_3$-adrenoreceptor agonist agents; sibutramine, gastrointestinal lipase inhibitors (such as orlistat), and leptins. Other agents used in treating obesity or obesity-related disorders include neuropeptide Y, enterostatin, cholecytokinin, bombesin, amylin, histamine H$_3$ receptors, dopamine D$_2$ receptor modulators, melanocyte stimulating hormone, corticotrophin releasing factor, galanin and gamma amino butyric acid (GABA).

The above other therapeutic agents, when employed in combination with the compounds of the present invention may be used, for example, in those amounts indicated in the *Physicians' Desk Reference*, as in the patents set out above, or as otherwise determined by one of ordinary skill in the art.

Particularly when provided as a single dosage unit, the potential exists for a chemical interaction between the combined active ingredients. For this reason, when the compound of the present invention and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material that affects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

The compounds of the present invention can be administered alone or in combination with one or more, preferably one to three, additional therapeutic agents. By "administered in combination" or "combination therapy" it is meant that the compound of the present invention and one or more, preferably one to three, additional therapeutic agents are administered concurrently to the mammal being treated. When administered in combination, each component may be administered at the same time or sequentially in any order at different points in time. Thus, each component may be administered separately but sufficiently closely in time so as to provide the desired therapeutic effect.

The compounds of the present invention are also useful as standard or reference compounds, for example as a quality standard or control, in tests or assays involving the myeloperoxidase. Such compounds may be provided in a commercial kit, for example, for use in pharmaceutical research involving myeloperoxidase activity. For example, a compound of the present invention could be used as a reference in an assay to compare its known activity to a compound with an unknown activity. This would ensure the experimenter that the assay was being performed properly and provide a basis for comparison, especially if the test compound was a derivative of the reference compound. When developing new assays or protocols, compounds according to the present invention could be used to test their effectiveness. The compounds of the present invention may also be used in diagnostic assays involving myeloperoxidase.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises a first therapeutic agent, comprising a compound of the present invention or a pharmaceutically acceptable salt form thereof; and, (c) a package insert stating that the pharmaceutical composition can be used for the treatment and/or prophylaxis of dyslipidemias and the sequelae thereof. In another embodiment, the package insert states that the pharmaceutical composition can be used in combination (as defined previously) with a second therapeutic agent for the treatment and/or prophylaxis of dyslipidemias and the sequelae thereof. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

Other features of the invention should become apparent in the course of the above descriptions of exemplary embodiments that are given for illustration of the invention and are not intended to be limiting thereof.

VI. Examples

The following Examples have been prepared, isolated and characterized using the methods disclosed herein. The following examples demonstrate a partial scope of the invention and are not meant to be limiting of the scope of the invention. Unless otherwise noted, the compounds were isolated as the free base.

General Synthesis Procedures:

For Schemes 1-5, the following general procedures are applicable as performed in sequences defined in the appropriate Scheme:

General Diazine Formation Procedure:

According to the procedure of Yao et al. (*Arch. Pharm. Chem. Life. Sci.*, 342:274 (2009)), to a solution or slurry of p-chloroaniline (1.0 eq) in 6N HCl (3.8 eq) at 0° C. was added an aqueous solution of sodium nitrite (1.0 eq). After stirring for 30 min at 0° C., this solution was added to a solution of diaminopyridine (e.g., 1-1, 2-1, or 3-1, 1.0 eq) either in water or a biphasic mixture of water and EtOAc (approximately 1:1 v/v). After 30-60 min of stirring, the resulting mixture may or may not be treated with sodium acetate to facilitate homogenization of the reaction mixture. The mixture was then allowed to stir 0.5-24 h, and then was partitioned between water and EtOAc. The organic layer was then concentrated and purified by silica gel chromatography to yield the desired diazine pyridine intermediates (e.g., 1-2, 2-2, or 3-2).

General Zinc Diazine Reduction Procedure:

A solution of diazine pyridine intermediate (e.g., 1-2, 2-2, or 3-2) in EtOH was treated with acetic acid (1-5 eq) and zinc powder (2-10 eq) and stirred at 60° C. After 10-120 min, the solution was filtered through CELITE® and concentrated, and the residue was purified by silica gel chromatography to yield the desired triamine intermediate (e.g., 1-3, 2-3, or 3-3).

General Hydrazine Diazine Reduction Procedure:

Diazine intermediate (e.g., 1-2, 2-2, or 3-2) was suspended in EtOH in a sealable pressure vial and excess hydrazine (20-40% v/v) added. The vial was sealed and heated either at 100° C. on the bench for 24-48 h or at 150° C. for 2 h in a microwave reactor. After cooling to rt, the reaction mixture was either evaporated to dryness or diluted with EtOAc and washed with water and brine, dried over anh. $Na_2SO_4$, filtered and evaporated, then purified by silica gel chromatography to provide triamine intermediate (e.g., 1-3, 2-3, or 3-3).

General Triazole Formation Procedure:

A solution of triamine intermediate (e.g., 1-3, 2-3, or 3-3, 1.0 eq) in THF was treated with isoamylnitrite (0.9 eq). Several drops of acetic acid may or may not have been added to enhance the reaction rate. In the event of incomplete conversion, additional isoamylnitrite may have been added. After 2-72 h, the reaction may have been treated with 7N methanolic ammonia or urea to consume residual isoamylnitrite. The solution was concentrated, and the residue was purified by column chromatography or preparative HPLC to furnish triazole intermediates 1-4 or examples of the general formula (I).

General Benzyl Halide Suzuki Cross-Coupling Procedure:

Boronic acid 4-3 (1.0 eq), benzyl halide (1.5 eq), palladium acetate (0.1 eq), triphenylphosphine (0.2 eq), and potassium phosphate (2 eq) were slurried in a mixture of DME/EtOH/water (10:1:1, 0.135M) and the suspension was blanketed under argon and heated to 80° C. overnight. The reaction mixture was cooled and partitioned between water and EtOAc. The organic layer was concentrated, and the residue was purified by column chromatography to furnish 4-alkylpyridine 4-4 which was deprotected according to the General Bis-pyrrole Deprotection Procedure to furnish diaminopyridine 3-1, which was elaborated to compounds of the general formula (I) according to procedures described in Scheme 3.

General Bis-Pyrrole Deprotection Procedure:

A 0.1 M solution of bis-pyrrolylpyridine 4-4 (1.0 eq) in either iPrOH/water (4:1), EtOH/water (4:1) or neat EtOH was treated with hydroxylammonium chloride (20 eq) and $Et_3N$ (10 eq). The resulting mixture was heated to 80° C. over 16-96 hours, treated with sodium bicarbonate solution and extracted with EtOAc. The organic layer was concentrated and the residue purified by column chromatography to furnish diaminopyridine intermediate 3-1 which was elaborated to compounds of the general formula (I) according to procedures described in Scheme 3.

For Schemes 1 and 2, the following general procedures are applicable as performed in sequences defined in the appropriate Scheme:

General Negishi Cross-Coupling Procedure 1:

To a solution of aryl bromide intermediate (e.g., 1-1, 1-2, or 1-4, 1.0 eq), tris(dibenzylidineacetone)dipalladium (0.05 eq), and (tri-tert-butylphosphonium) tetrafluoroborate (0.1 eq) in THF was added a solution of organozinc reagent (1-10 eq in THF). The solution was allowed to stir overnight, then concentrated and purified by column chromatography or preparative HPLC to furnish alkylated pyridine intermediates 2-1 or 2-2 (in the case of bromide intermediates 1-1 or 1-2) or examples of the general formula (I) (in the case of bromide intermediate 1-4).

General Negishi Cross-Coupling Procedure 2:

To a slurry of zinc powder (10 eq) in THF was added TMSCl (0.05 eq) and 1,2-dibromoethane (0.05 eq). The slurry was briefly heated to reflux. To this solution was added an appropriate benzyl halide (5 eq) at rt. After 30-60 min, the solution was treated with an aryl bromide intermediate (e.g., 1-1, 1-2, or 1-4, 1.0 eq), tris(dibenzylidineacetone)dipalladium (0.05 eq), and (tri-tert-butylphosphonium) tetrafluoroborate (0.1 eq) in THF. The solution was allowed to stir 1-24 h, then concentrated and purified by column chromatography or preparative HPLC to furnish alkylated pyridine intermediate 2-1 or 2-2 (in the case of bromide intermediates 1-1 or 1-2) or examples of the general formula (I) (in the case of bromide intermediate 1-4).

Example 1: 7-Benzyl-3H-[1,2,3]triazolo[4,5-b]pyridin-5-amine

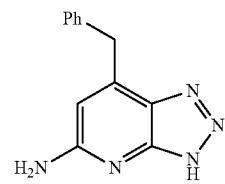

Example 1 as prepared according to procedures described in Scheme 1.

Intermediate 1a: (E)-4-Bromo-3-((4-chlorophenyl)diazenyl)pyridine-2,6-diamine

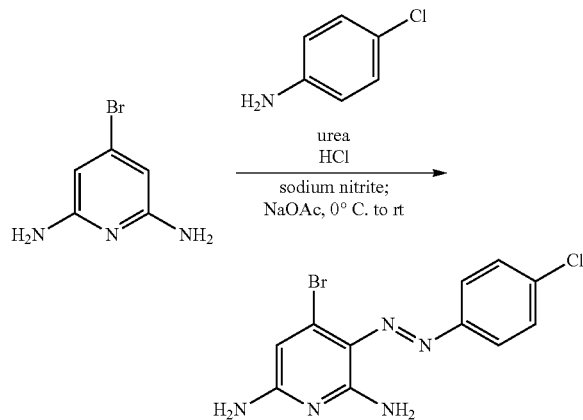

To a solution of 4-chloroaniline (0.678 g, 5.32 mmol) in 6 N HCl (3.4 mL, 20. mmol) at 0° C. was added a solution of sodium nitrite (0.367 g, 5.32 mmol) in water (0.58 mL), and the reaction mixture was stirred for 30 min. The reaction mixture was then treated with urea (0.032 g, 0.53 mmol). The solution was then poured into a solution of 4-bromopyridine-2,6-diamine (1.00 g, 5.32 mmol) in water (14.5 mL). After 30 min, sodium acetate (1.963 g, 23.93 mmol) was added, and the reaction mixture was allowed to stir overnight. The reaction mixture was then filtered, and the filtrate was dried under reduced pressure to furnish the title compound (1a, 1.19 g, 3.65 mmol, 68.7% yield). MS(ESI) m/z 328.0 (M+H).

Intermediate 1b: 4-Bromopyridine-2,3,6-triamine

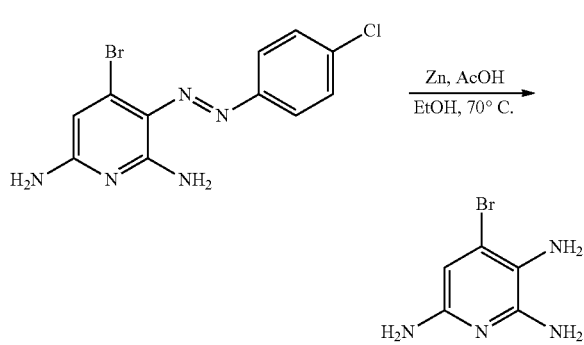

To a solution of (E)-4-bromo-3-((4-chlorophenyl)diazenyl)pyridine-2,6-diamine (1a, 1.19 g, 3.65 mmol) in EtOH (12 mL) was added acetic acid (0.63 mL, 11 mmol) and zinc powder (0.717 g, 11.0 mmol), and the reaction mixture was heated to 70° C. After 90 min, the reaction mixture was filtered through CELITE® and concentrated. The residue was purified by silica gel chromatography to furnish the title compound (1b, 0.568 g, 2.80 mmol, 77.0% yield).

Intermediate 1c: 7-Bromo-3H-[1,2,3]triazolo[4,5-b]pyridin-5-amine

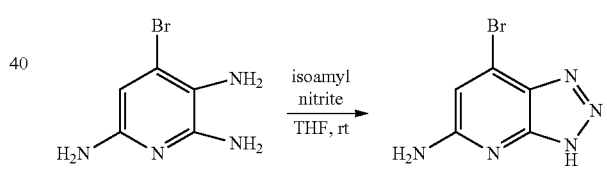

To a solution of 4-bromopyridine-2,3,6-triamine (1b, 0.568 g, 2.80 mmol) in THF (28 mL) was added isoamylnitrite (0.38 mL, 2.8 mmol). The reaction mixture was allowed to stir overnight. The solution was then treated with an additional 0.20 mL of isoamylnitrite and the solution was allowed to stir overnight. The solution was then concentrated, and the residue purified by silica gel chromatography to furnish the title compound (1c, 0.185 g, 0.864 mmol, 30.9% yield). MS(ESI) m/z 214.0 (M+H).

Example 1 (Free Base): 7-benzyl-3H-[1,2,3]triazolo[4,5-b]pyridin-5-amine

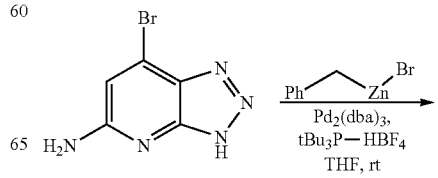

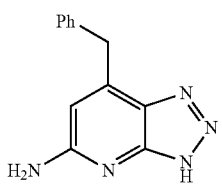 [SMILES: Nc1cc(Cc2ccccc2)c2nn[nH]c2n1]

7-Bromo-3H-[1,2,3]triazolo[4,5-b]pyridin-5-amine (1c, 0.4 g, 1.87 mmol), tri-t-butylphosphonium tetrafluoroborate (0.054 g, 0.19 mmol) and tris(dibenzylideneacetone)dipalladium(0) (0.086 g, 0.093 mmol) was dissolved in THF (19 mL) and added to benzylzinc(II) bromide (11.2 mL, 5.6 mmol, 0.5 M in THF), and the reaction mixture was allowed to stir under argon overnight. The solution was then adsorbed on silica gel and purified by silica gel chromatography to furnish a solid mass, which was then partially dissolved in EtOAc, decanted and concentrated to furnish the title compound (0.168 g, 0.709 mmol, 37.9% yield). MS(ESI) m/z 226.0 (M+H). $^1$H NMR (400 MHz, DMSO-$d_6$) δ 7.43-7.14 (m, 5H), 6.53 (br s, 2H), 6.23 (s, 1H), 4.22 (s, 2H). Analytical HPLC Col A: 5.51 min, 94%; Col B: 6.27 min, 99%. LC RT=4.49 min (Method A).

Alternatively, Example 1 can be prepared as follows:

Intermediate 1d: 7-bromo-N,3-ditrityl-3H-[1,2,3]triazolo[4,5-b]pyridin-5-amine

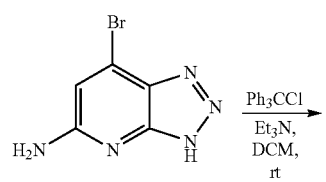

To a suspension 7-bromo-3H-[1,2,3]triazolo[4,5-b]pyridin-5-amine (1c, 1.31, 6.12 mmol), and trityl chloride (3.41 g, 12.2 mmol) slurried in dichloromethane (61 mL) was added triethylamine (2.6 mL, 18 mmol) and the reaction mixture was allowed to stir under argon overnight. The reaction mixture was then concentrated and purified via flash chromatography to furnish the title compound as a mixture of trityl regioisomers (2.69 g, 3.85 mmol, 62.9% yield). MS(ESI) m/z 699.9, 697.9 (M+H).

Intermediate 1e: 7-benzyl-N,3-ditrityl-3H-[1,2,3]triazolo[4,5-b]pyridin-5-amine

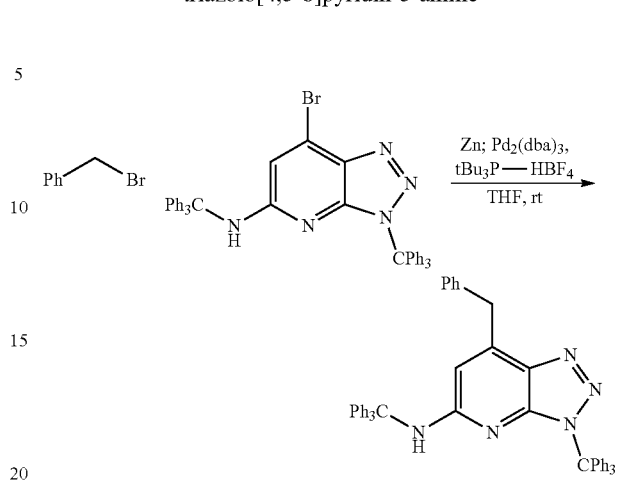

Zinc powder (16.9 g, 258 mmol) in THF (129 mL) was treated with 1,2-dibromoethane (1.7 mL, 19 mmol) and TMS-Cl (2.5 mL, 19 mmol) under argon. After 30 min, the solution was treated with benzylbromide (15 mL, 130 mmol). After 30 min, the solution was cannulated into a mixture of 7-bromo-N,3-ditrityl-3H-[1,2,3]triazolo[4,5-b]pyridin-5-amine (1d, 30 g, 43 mmol), tri-t-butylphosphonium tetrafluoroborate (0.623 g, 2.15 mmol) and tris(dibenzylideneacetone)dipalladium(0) (0.983 g, 1.073 mmol) dissolved in THF (130 mL), and the reaction mixture was allowed to stir under argon overnight at rt. The solution was concentrated and partitioned between NH$_4$Cl and EtOAc, extracted with EtOAc. The organic layers were concentrated and the residue purified by silica gel chromatography to furnish the title compound (18.1 g, 25.6 mmol, 59.5% yield). MS(ESI) m/z 710.1 (M+H). $^1$H NMR major regioisomer (400 MHz, chloroform-d) δ 7.25-7.20 (m, 10H), 7.19-7.10 (m, 19H), 7.08-7.01 (m, 6H), 6.98-6.92 (m, 2H), 5.71 (s, 1H), 5.60 (s, 1H), 4.06 (s, 2H).

Example 1 (TFA salt): 7-benzyl-3H-[1,2,3]triazolo[4,5-b]pyridin-5-amine

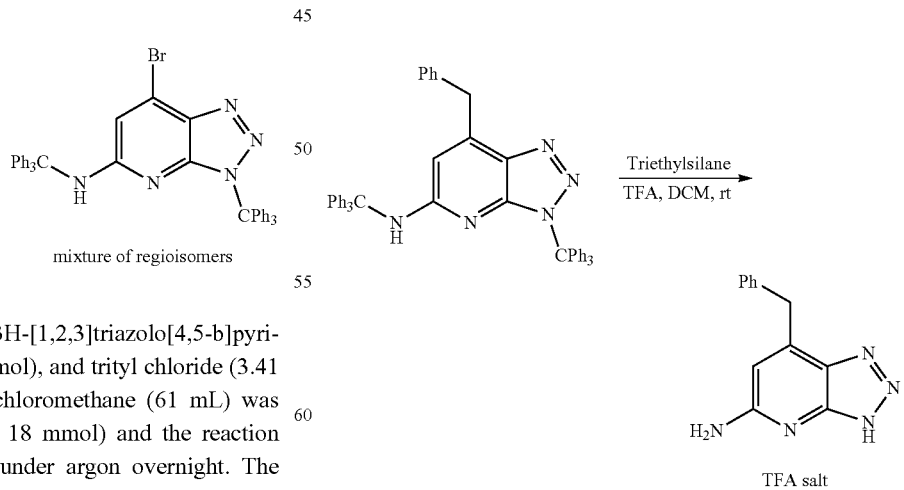

To a solution of 7-benzyl-N, 3-ditrityl-3H-[1,2,3]triazolo[4,5-b]pyridin-5-amine (18.1 g, 25.6 mmol) and triethylsilane (8.2 mL, 51 mmol) dissolved in DCM (204 mL) was added TFA (51 mL) and the reaction mixture was allowed to stir under argon for one hour. The solution was then concentrated and the resulting solids were triturated with ether. The solids were filtered and dried at rt under vacuum for 3 hours to furnish the title compound as the TFA salt (7.26 g, 21.2 mmol, 83% yield). MS(ESI) m/z 226.0 (M+H). $^1$H NMR (400 MHz, DMSO-$d_6$) δ 7.40-7.30 (m, 4H), 7.26 (d, J=6.8 Hz, 1H), 6.33 (br. s., 1H), 4.26 (s, 2H). Analytical HPLC Col A: 4.25 min, 99%; Col B: 4.41 min, 98%. (Method A).

Example 1 (Free Base): 7-benzyl-3H-[1,2,3]triazolo[4,5-b]pyridin-5-amine

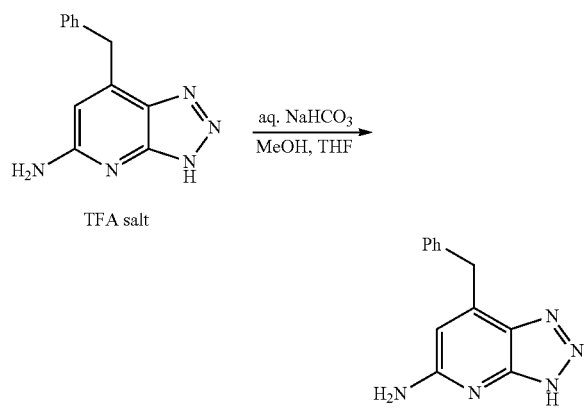

To a solution of 7-benzyl-3H-[1,2,3]triazolo[4,5-b]pyridin-5-amine, TFA (7.000 g, 20.63 mmol) dissolved in MeOH (247 mL) and THF (35 mL) at 40° C. was added a solution of NaHCO$_3$ (1.733 g, 20.63 mmol) in water (35 mL) and stirred. As solids precipitated, the reaction mixture was removed from heat and allowed to stand at rt. The solids were filtered with 0.4 micron glass filter that was washed with minimal MeOH. To the mother liquor was added 2.8 L of water and the resulting solid was filtered washed with water to furnish title compound (2.54 g, 11.3 mmol, 54.9% yield). MS(ESI) m/z 226.0 (M+H). $^1$H NMR (400 MHz, DMSO-$d_6$) δ 7.38-7.29 (m, 4H), 7.26-7.20 (m, 1H), 6.52 (br. s., 2H), 6.25 (s, 1H), 4.24 (s, 2H). Analytical HPLC Col A: 4.34 min, 100%; Col B: 4.42 min, 100%. (Method A).

Examples 2-6 (Table 2) were prepared according the procedures described for Example 1 using the appropriate benzylzinc halides, which were either commercially available or readily prepared in situ according to the procedure of Sher et al. (*J. Comb. Chem.*, 7:99 (2005)).

Example 7: Methyl 3-((5-amino-3H-[1,2,3]triazolo[4,5-b]pyridin-7-yl)methyl)benzoate

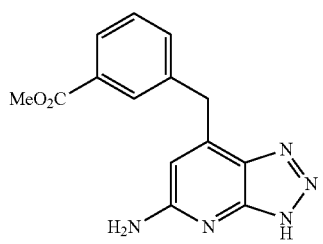

Example 7 as prepared according to procedures outlined in Scheme 2, route (a).

Intermediate 7a: Methyl 3-((2,6-diaminopyridin-4-yl)methyl)benzoate

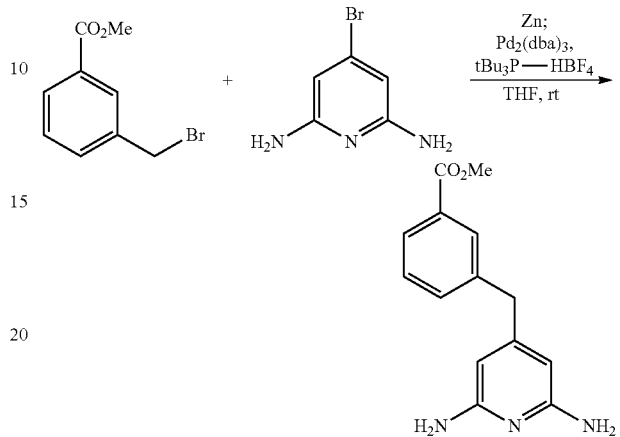

Zinc powder (0.696 g, 10.6 mmol) in THF (11 mL) was treated with 1,2-dibromoethane (0.014 mL, 0.16 mmol) and TMS-Cl (0.020 mL, 0.16 mmol) under argon. After 30 min, the solution was treated with methyl 3-(bromomethyl)benzoate (1.22 g, 5.32 mmol) dissolved in minimal amount of THF. After 30 min, the solution was treated with 4-bromopyridine-2,6-diamine (0.200 g, 1.06 mmol), tri(tert-butylphosphonium)tetrafluoroborate (0.031 g, 0.11 mmol) and Pd$_2$(dba)$_3$ (0.049 g, 0.053 mmol) and allowed to stir overnight. The solution was extracted from water with EtOAc. The organic layer was concentrated, and the residue purified by silica gel chromatography to furnish the title compound (7a, 0.175 g, 0.680 mmol, 63.9% yield). MS(ESI) m/z 258.0 (M+H).

Intermediate 7b: (E)-Methyl 3-((2,6-diamino-3-((4-chlorophenyl)diazenyl)pyridin-4-yl)methyl)benzoate

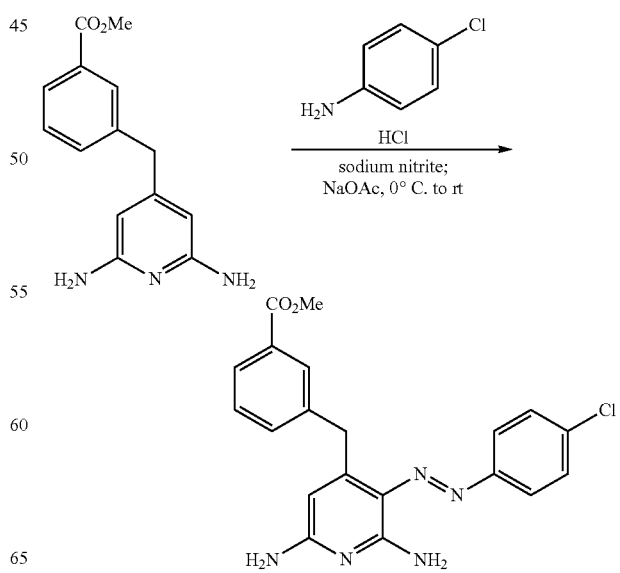

To a solution of 4-chloroaniline (0.087 g, 0.68 mmol) in 6N HCl (0.43 mL, 2.6 mmol) was added a solution of sodium nitrite (0.047 g, 0.68 mmol) in water (0.07 mL), and the reaction mixture was stirred for 30 min. The above solution was poured into a solution of methyl 3-((2,6-diaminopyridin-4-yl)methyl)benzoate (7a, 0.175 g, 0.680 mmol) in water (1.9 mL). After 30 min, sodium acetate (0.251 g, 3.06 mmol) was added, and the reaction mixture was allowed to stir overnight. The slurry was filtered and dried under high vacuum to furnish the title compound (7b, 0.160 g, 0.404 mmol, 59.4% yield). MS(ESI) m/z 396.0 (M+H).

Intermediate 7c: Methyl 3-((2,3,6-triaminopyridin-4-yl)methyl)benzoate

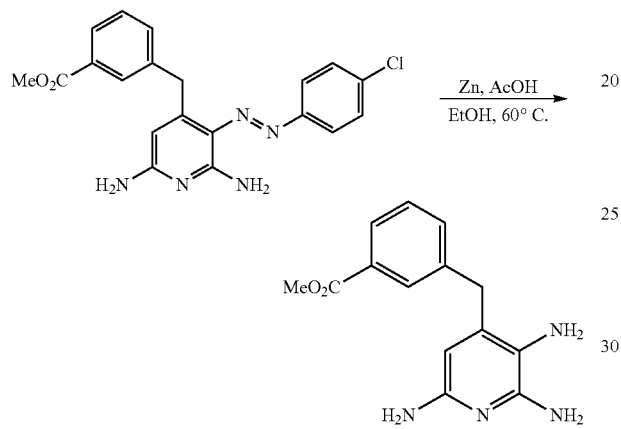

To a solution of (E)-methyl 3-((2,6-diamino-3-((4-chlorophenyl)diazenyl)pyridin-4-yl)methyl)benzoate (7b, 0.145 g, 0.366 mmol) in EtOH (3.7 mL) was added acetic acid (0.063 mL, 1.1 mmol) and zinc powder (0.072 g, 1.1 mmol), and the reaction mixture was heated to 60° C. for 10 min. The reaction mixture was then filtered and concentrated, and the residue purified by silica gel chromatography to furnish the title compound (7c, 0.060 g, 0.22 mmol, 60% yield). MS(ESI) m/z 273.1 (M+H).

Example 7

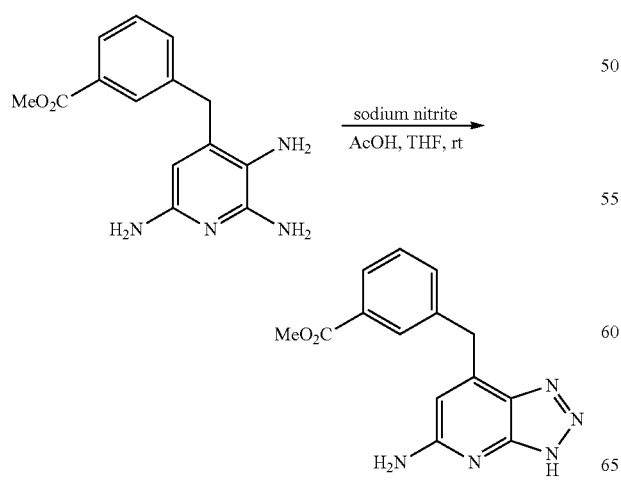

A slurry of methyl 3-((2,3,6-triaminopyridin-4-yl)methyl)benzoate (7c, 0.060 g, 0.22 mmol) and sodium nitrite (0.017 g, 0.24 mmol) in THF (2.2 mL) was treated with acetic acid (0.038 mL, 0.66 mmol), and the reaction mixture was stirred overnight. The slurry was filtered and concentrated, and the residue purified by preparatory HPLC to furnish the title compound (0.0026 g, 8.7 µmol, 4.0% yield). MS(ESI) m/z 284.1 (M+H). $^1$H NMR (500 MHz, DMSO-$d_6$) δ 7.96 (s, 1H), 7.85 (d, J=7.7 Hz, 1H), 7.66 (d, J=7.7 Hz, 1H), 7.53-7.47 (m, 1H), 6.32 (br. s., 1H), 4.35 (s, 2H), 3.88-3.82 (m, 3H). Analytical HPLC Col A: 4.93 min, 88%; Col B: 5.24 min, 89%. LC RT=4.93 min (Method A).

Examples 8-16 (Table 2) were prepared using procedures similar to that described for Example 7 by using the appropriate benzylzinc halides, which were either commercially available or readily prepared in situ according to the procedure of Sher et al. (*J. Comb. Chem.*, 7:99 (2005)).

Example 17: 7-(Biphenyl-3-ylmethyl)-3H-[1,2,3]triazolo[4,5-b]pyridin-5-amine

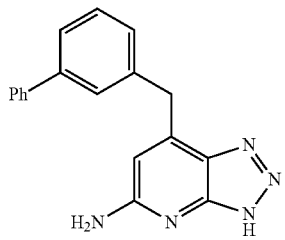 [SMILES: Nc1cc(Cc2cccc(-c3ccccc3)c2)c2nn[nH]c2n1]

Example 17 as prepared according to Scheme 2, route (b):

Intermediate 17a: (E)-4-(Biphenyl-3-ylmethyl)-3-((4-chlorophenyl)diazenyl)pyridine-2,6-diamine

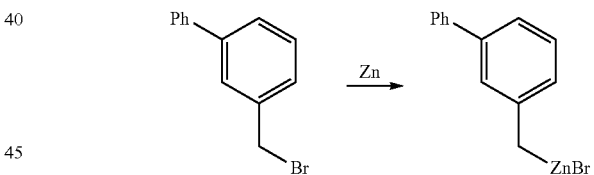

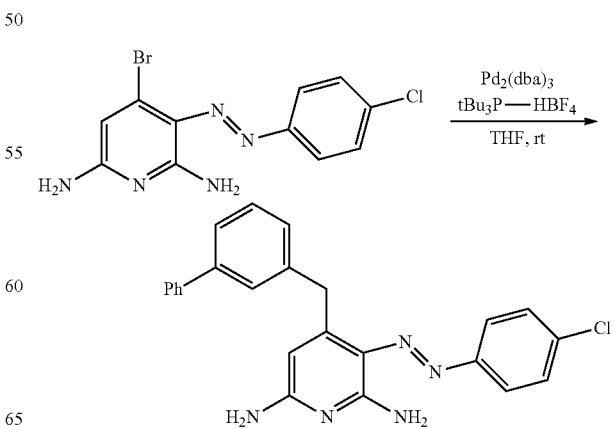

To a slurry of zinc (0.654 g, 10.0 mmol) in THF (5.0 mL) was added ethylene dibromide (21.6 mL, 0.250 mmol) and TMS-Cl (0.032 mL, 0.25 mmol). The reaction mixture was heated to reflux briefly, and then allowed to cool to rt. After 30 min, the solution was treated with 3-(bromomethyl) biphenyl (1.24 g, 5.00 mmol) and after 30 min assayed by ¹H NMR in CD₃OD, which indicated partial conversion (ca. 60:40 benzylzinc/benzylbromide by ¹H NMR). To this slurry of 3-bromozinc methyl biphenyl (1.24 g, 5.00 mmol) in THF (5 mL) was added Pd₂(dba)₃ (0.023 g, 0.025 mmol), tri(tert-butylphosphonium)tetrafluoroborate (0.015 g, 0.051 mmol) and (E)-4-bromo-3-((4-chlorophenyl)diazenyl)pyridine-2,6-diamine (1a, 0.165 g, 0.505 mmol) in THF (5.0 mL). After 1 h, the solution was quenched with NH₄Cl, extracted with EtOAc, concentrated and the residue purified by silica gel chromatography to furnish the title compound (17a, 0.123 g, 0.297 mmol, 58.8% yield). MS(ESI) m/z 414.2 (M+H).

Intermediate 17b:
4-(Biphenyl-3-ylmethyl)pyridine-2,3,6-triamine

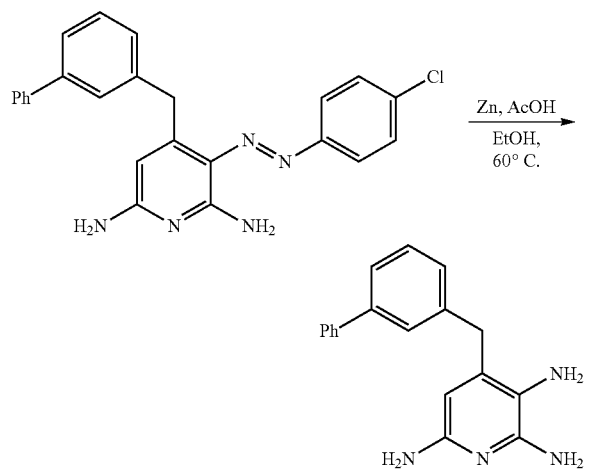

To a solution of (E)-4-(biphenyl-3-ylmethyl)-3-((4-chlorophenyl)diazenyl)pyridine-2,6-diamine (17a, 0.123 g, 0.297 mmol) in EtOH (1.0 mL) was added acetic acid (0.051 mL, 0.89 mmol) and zinc powder (0.058 g, 0.89 mmol), and the reaction mixture was heated to 60° C. After 30 min, the reaction slurry was filtered through CELITE® and concentrated, and the residue purified by silica gel chromatography to furnish the title compound (17b, 0.029 g, 0.100 mmol, 33.6% yield). MS(ESI) m/z 291.2 (M+H).

Example 17

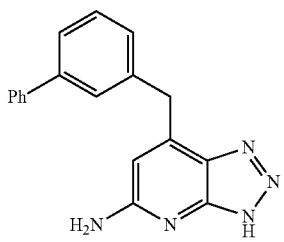

A slurry of 4-(biphenyl-3-ylmethyl)pyridine-2,3,6-triamine (17b, 0.029 g, 0.10 mmol) and sodium nitrite (7.58 mg, 0.110 mmol) in THF (1.0 mL) was treated with acetic acid (0.017 mL, 0.30 mmol), and the reaction mixture stirred overnight. The reaction slurry was filtered and concentrated, and the residue was purified by preparatory HPLC to furnish the title compound (0.0063 g, 0.021 mmol, 21% yield). MS(ESI) m/z 291.2 (M+H). ¹H NMR (500 MHz, DMSO-d₆) δ 7.70 (s, 1H), 7.67-7.63 (m, 2H), 7.55 (d, J=7.7 Hz, 1H), 7.50-7.34 (m, 5H), 6.40 (br. s., 1H), 4.35 (s, 2H). Analytical HPLC Col A: 6.25 min, 100%; Col B: 6.74 min, 99%. LC RT=6.25 min (Method A).

Examples 18-45 (Table 2) were prepared according the procedures described for Example 17 by using the appropriate benzylzinc halides, which were either commercially available or readily prepared in situ according to the procedure of Sher et al. (*J. Comb. Chem.*, 7:99 (2005)). Examples 18-22 were isolated as the TFA salt.

Example 46: 3-((5-Amino-3H-[1,2,3]triazolo[4,5-b]pyridin-7-yl)methyl)-N-benzylbenzamide

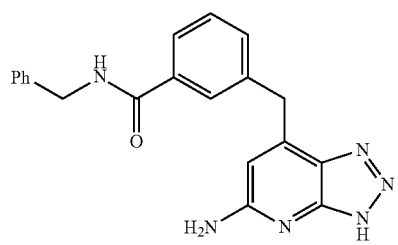 [SMILES: Nc1cc(Cc2cccc(C(=O)NCc3ccccc3)c2)c2nn[nH]c2n1]

Intermediate 46a: N-Benzyl-3-((2,6-diaminopyridin-4-yl)methyl)benzamide

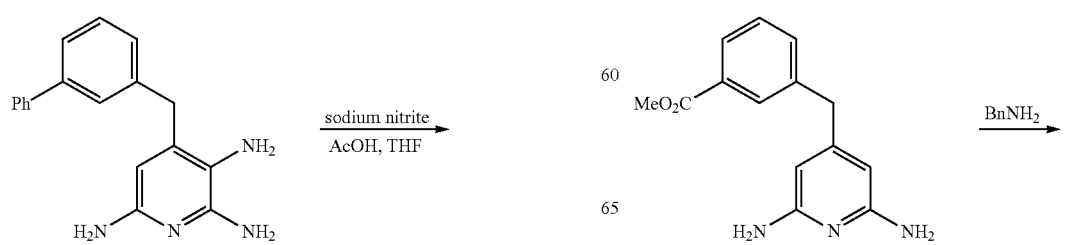

49

-continued

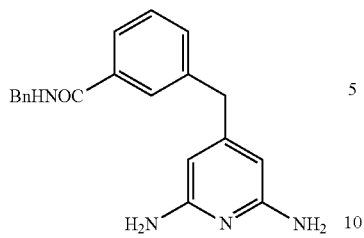

Methyl 3-((2,6-diaminopyridin-4-yl)methyl)benzoate (7a, 0.200 g, 0.777 mmol) was suspended in phenylmethanamine (1.0 mL, 9.2 mmol), and the reaction mixture was heated to 100° C. overnight. The reaction mixture was cooled and concentrated, and the residue was purified silica gel chromatography to furnish the title compound (46a, 0.200 g, 0.602 mmol, 77% yield). MS(ESI) m/z 333.1 (M+H).

Intermediate 46b: (E)-N-Benzyl-3-((2,6-diamino-3-((4-chlorophenyl)diazenyl)pyridin-4-yl)methyl)benzamide

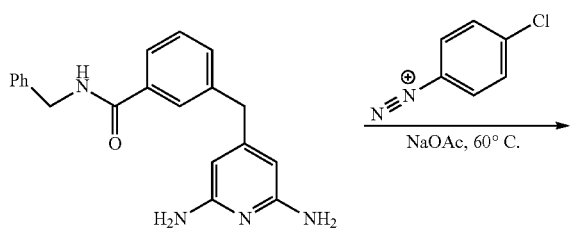

A solution of 4-chlorobenzenediazonium chloride salt (0.105 g, 0.602 mmol) was poured into a solution of N-benzyl-3-((2,6-diaminopyridin-4-yl)methyl)benzamide (46a, 0.200 g, 0.602 mmol) in water (6.0 mL)/EtOAc (6.0 mL) (+few drops of MeOH to ensure homogeneity). After 60 min, sodium acetate (0.222 g, 2.71 mmol) was added, and the reaction mixture was allowed to stir overnight. The solution was partitioned between water and EtOAc. The organic layer was concentrated and the residue purified by silica gel chromatography to furnish the title compound (46b, 0.218 g, 0.463 mmol, 77% yield). MS(ESI) m/z 470.9 (M+H).

50

Intermediate 46c: N-Benzyl-3-((2,3,6-triaminopyridin-4-yl)methyl)benzamide

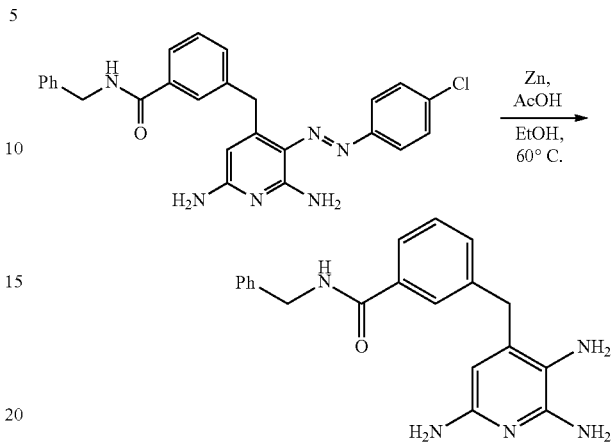

To a solution of (E)-N-benzyl-3-((2,6-diamino-3-((4-chlorophenyl)diazenyl)pyridin-4-yl)methyl)benzamide (46b, 0.218 g, 0.463 mmol) in EtOH (4.6 mL) was added acetic acid (0.079 mL, 1.4 mmol) and zinc powder (0.091 g, 1.4 mmol). The reaction mixture was heated to 60° C. for 20 min, and then filtered through CELITE® and concentrated. The residue was then purified by silica gel chromatography to furnish the title compound (46c, 0.020 g, 0.058 mmol, 12% yield), which was used without delay.

Example 46

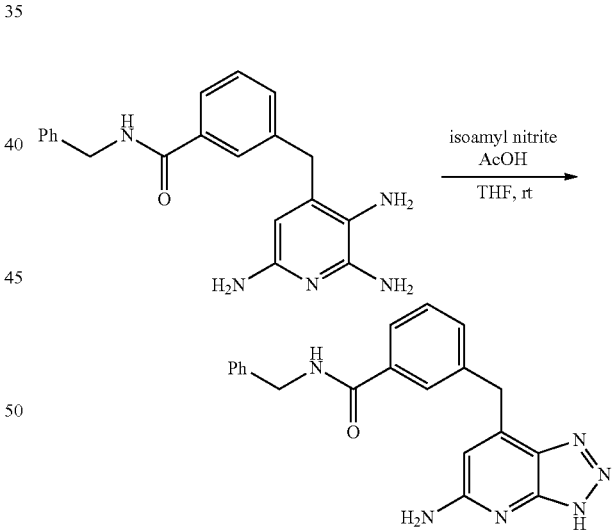

To a solution of N-benzyl-3-((2,3,6-triaminopyridin-4-yl)methyl)benzamide (46c, 0.070 g, 0.20 mmol) in THF (2.0 mL) was added AcOH (0.012 mL, 0.20 mmol) and isoamylnitrite (0.024 mL, 0.18 mmol), and the reaction mixture was stirred overnight. The reaction mixture was then concentrated, and the residue was purified by preparative HPLC to furnish the title compound (0.0016 g, 3.8 μmol, 1.9% yield). MS(ESI) m/z 359.1 (M+H). $^1$H NMR (500 MHz, methanol-$d_4$) δ 7.88 (s, 1H), 7.83-7.74 (m, 1H), 7.59 (d, J=8.0 Hz, 1H), 7.55-7.43 (m, 1H), 7.40-7.30 (m, 4H), 7.29-7.21 (m, 1H), 6.57 (s, 1H), 4.59 (s, 2H), 4.45 (s, 2H).

Analytical HPLC Col A: 4.93 min, 85%; Col B: 5.24 min, 85%. LC RT=5.02 min (Method A).

Example 47: 3-((5-Amino-3H-[1,2,3]triazolo[4,5-b]pyridin-7-yl)methyl)-N-phenethylbenzamide Intermediate 47a: 3-((2,6-Diaminopyridin-4-yl)methyl)-N-phenethylbenzamide Methyl 3-((2,6-diaminopyridin-4-yl)methyl)benzoate (7a, 0.100 g, 0.389 mmol) was suspended in 2-phenylethanamine (0.50 mL, 4.0 mmol), and the reaction mixture was heated to 100° C. overnight. The reaction mixture was concentrated, and the residue was purified by silica gel chromatography to furnish the title compound (47a, 0.106 g, 0.306 mmol, 79% yield). MS(ESI) m/z 347.1 (M+H).

Intermediate 47b: (E)-3-((2,6-Diamino-3-((4-chlorophenyl)diazenyl)pyridin-4-yl)methyl)-N-phenethylbenzamide

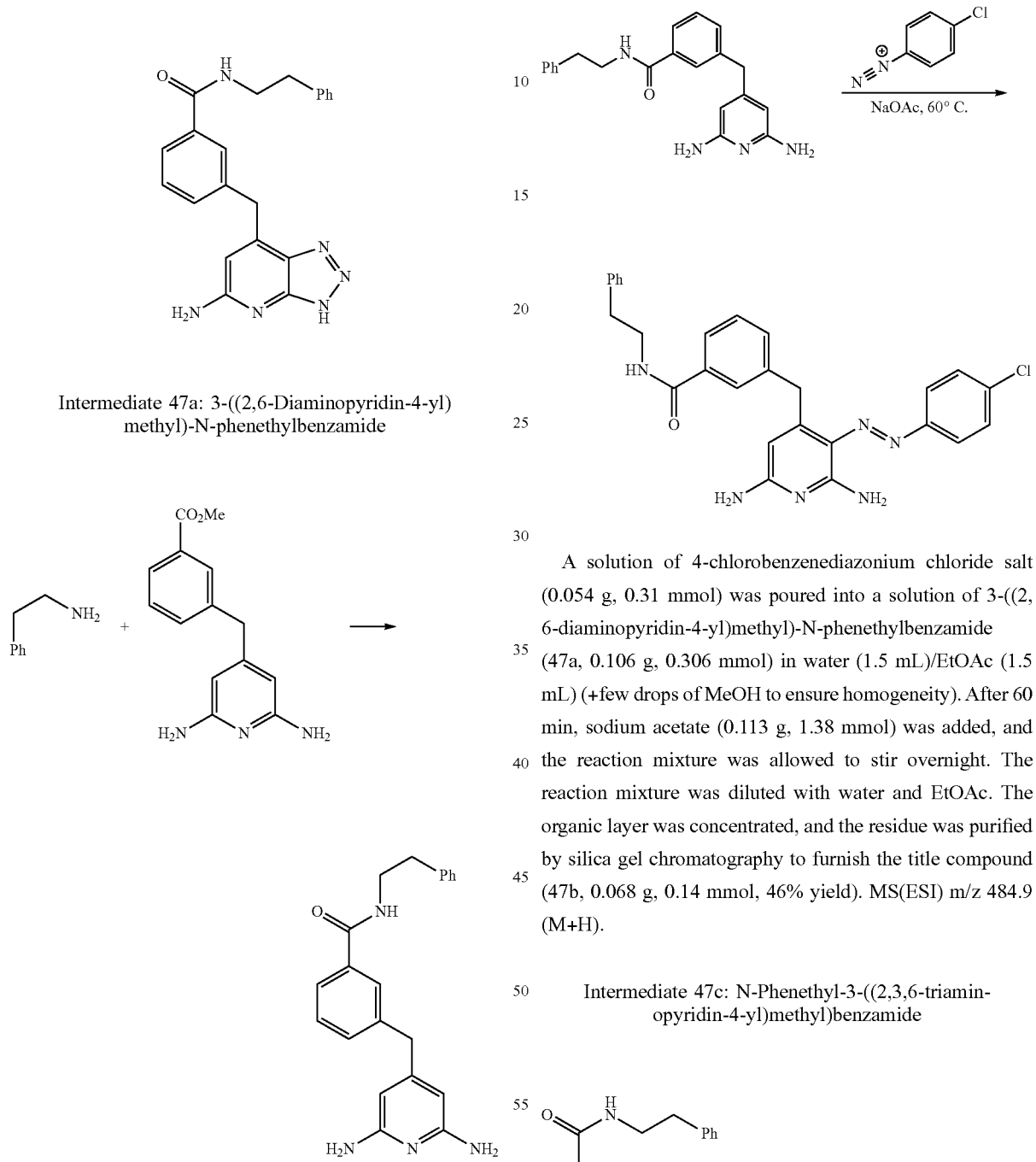

A solution of 4-chlorobenzenediazonium chloride salt (0.054 g, 0.31 mmol) was poured into a solution of 3-((2,6-diaminopyridin-4-yl)methyl)-N-phenethylbenzamide (47a, 0.106 g, 0.306 mmol) in water (1.5 mL)/EtOAc (1.5 mL) (+few drops of MeOH to ensure homogeneity). After 60 min, sodium acetate (0.113 g, 1.38 mmol) was added, and the reaction mixture was allowed to stir overnight. The reaction mixture was diluted with water and EtOAc. The organic layer was concentrated, and the residue was purified by silica gel chromatography to furnish the title compound (47b, 0.068 g, 0.14 mmol, 46% yield). MS(ESI) m/z 484.9 (M+H).

Intermediate 47c: N-Phenethyl-3-((2,3,6-triaminopyridin-4-yl)methyl)benzamide

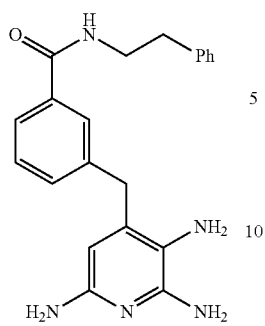

To a solution of (E)-3-((2,6-diamino-3-((4-chlorophenyl)diazenyl)pyridin-4-yl)methyl)-N-phenethylbenzamide (47b, 0.068 g, 0.14 mmol) in EtOH (1.4 mL) was added acetic acid (0.024 mL, 0.42 mmol) and zinc powder (0.028 g, 0.42 mmol), and the reaction mixture was heated to 60° C. for 20 min, then filtered through CELITE® and concentrated. The residue was then purified by silica gel chromatography to furnish the title compound (47c, 0.040 g, 0.11 mmol, 79% yield) which was used directly.

Example 47

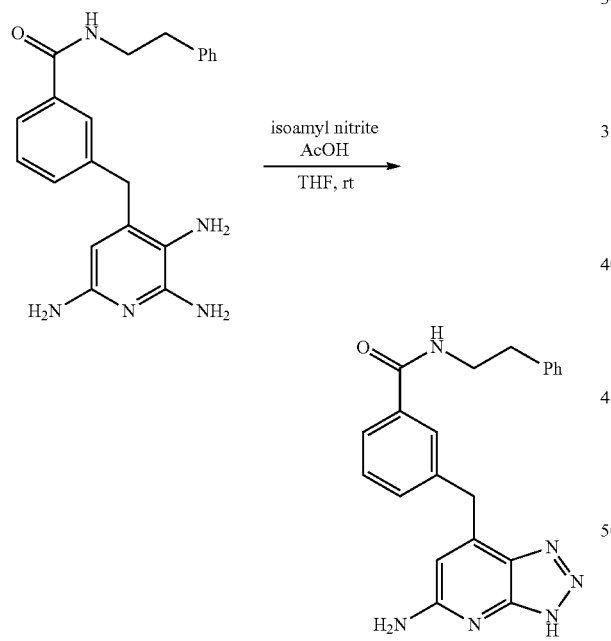

To a solution of N-phenethyl-3-((2,3,6-triaminopyridin-4-yl)methyl)benzamide (47c, 0.040 g, 0.11 mmol) in THF (1.1 mL) was added AcOH (6 μL, 0.1 mmol) and isoamyl nitrite (0.013 mL, 0.10 mmol), and the reaction mixture was allowed to stir overnight. The solution was concentrated and the residue purified by preparative HPLC to furnish the title compound (0.0105 g, 0.0270 mmol, 24.7% yield). MS(ESI) m/z 373.0 (M+H). $^1$H NMR (500 MHz, DMSO-d) δ 8.54 (t, J=5.5 Hz, 1H), 7.80 (s, 1H), 7.70 (d, J=7.7 Hz, 1H), 7.51 (d, J=7.7 Hz, 1H), 7.45-7.39 (m, 1H), 7.33-7.26 (m, 2H), 7.25-7.16 (m, 3H), 6.33 (br. s., 1H), 4.32 (s, 2H), 3.57-3.39 (m, 2H), 2.84 (t, J=7.6 Hz, 2H). Analytical HPLC Col A: 4.93 min, 98%; Col B: 5.24 min, 98%. LC RT=6.00 min (Method A).

Example 48: 7-(3-(1-Benzyl-1H-pyrazol-3-yl)benzyl)-3H-[1,2,3]triazolo[4,5-b]pyridin-5-amine

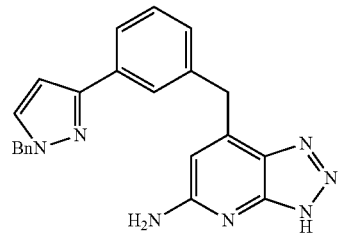 [SMILES: Nc1cc(Cc2cccc(-c3ccn(Cc4ccccc4)n3)c2)c2nn[nH]c2n1]

Intermediate 48a:
4-(3-Chlorobenzyl)pyridine-2,6-diamine

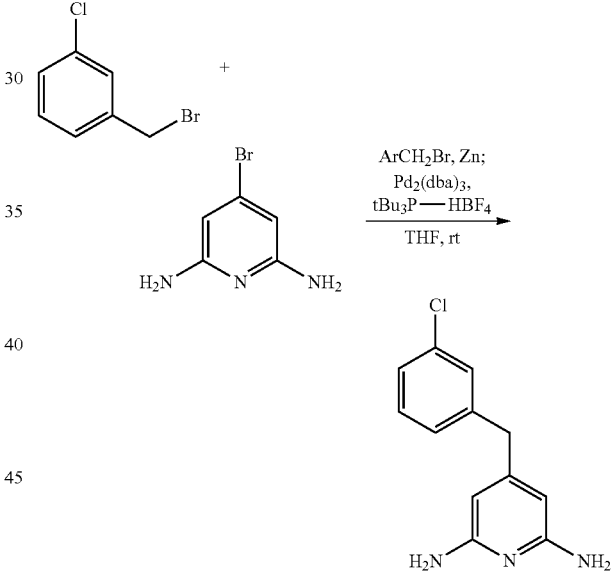

Zinc powder (12.5 g, 191 mmol) in THF (319 mL) was treated with 1,2-dibromoethane (0.41 mL, 4.8 mmol) and TMS-Cl (0.61 mL, 4.8 mmol) under argon. After 30 min, the solution was treated with 1-(bromomethyl)-3-chlorobenzene (20 g, 96 mmol) dissolved in a minimal amount of THF to maintain a free flowing solution. After 30 min, the solution was treated with 4-bromopyridine-2,6-diamine (6.0 g, 32 mmol), tri(tert-butylphosphonium)tetrafluoroborate (0.926 g, 3.19 mmol) and Pd$_2$(dba)$_3$ (1.46 g, 1.60 mmol), and the reaction mixture was allowed to stir overnight. The reaction mixture was extracted from water with EtOAc, and the organic layer concentrated. The residue was purified by silica gel chromatography to furnish the title compound (48a, 4.373 g, 18.71 mmol, 58.6% yield). MS(ESI) m/z 234.1 (M+H). $^1$H NMR (500 MHz, DMSO-d$_6$) δ 7.39-7.34 (m, 1H), 7.33-7.29 (m, 2H), 7.20 (d, J=7.4 Hz, 1H), 5.64 (s, 2H), 3.73 (s, 2H).

Intermediate 48b: 4-(3-(1-Benzyl-1H-pyrazol-4-yl)benzyl)pyridine-2,6-diamine

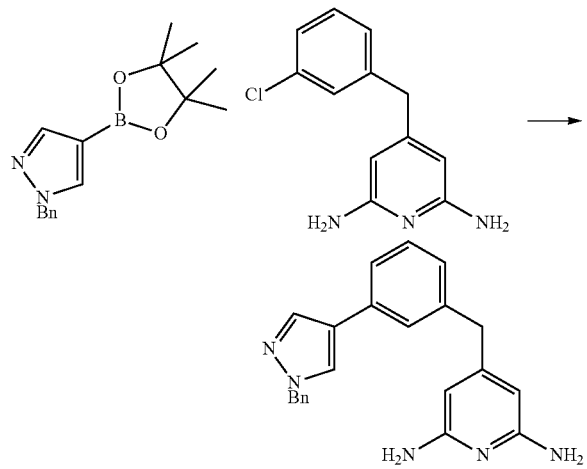

A suspension of 1-benzyl-4-(4,4,5,5-tetramethyl-1,3,2-dioxaborolan-2-yl)-1H-pyrazole (0.973 g, 3.42 mmol), 4-(3-chlorobenzyl)pyridine-2,6-diamine (48a, 0.400 g, 1.71 mmol), Pd(OAc)$_2$ (0.038 g, 0.17 mmol), K$_2$CO$_3$ (1.183 g, 8.56 mmol), 2-dicyclohexylphosphino-2',6'-dimethoxy-1,1'-biphenyl (0.070 g, 0.17 mmol) was heated in DME (7 mL)/water (1.4 mL) at 100° C. overnight. The solution was partitioned between EtOAc and water. The organic layer was concentrated, and the residue was purified by silica gel chromatography to furnish the title compound (48b, 0.365 g, 1.03 mmol, 60.0% yield). MS(ESI) m/z 356.1 (M+H).

Intermediate 48c: (E)-4-(3-(1-Benzyl-1H-pyrazol-3-yl)benzyl)-3-((4-chlorophenyl)diazenyl)pyridine-2,6-diamine

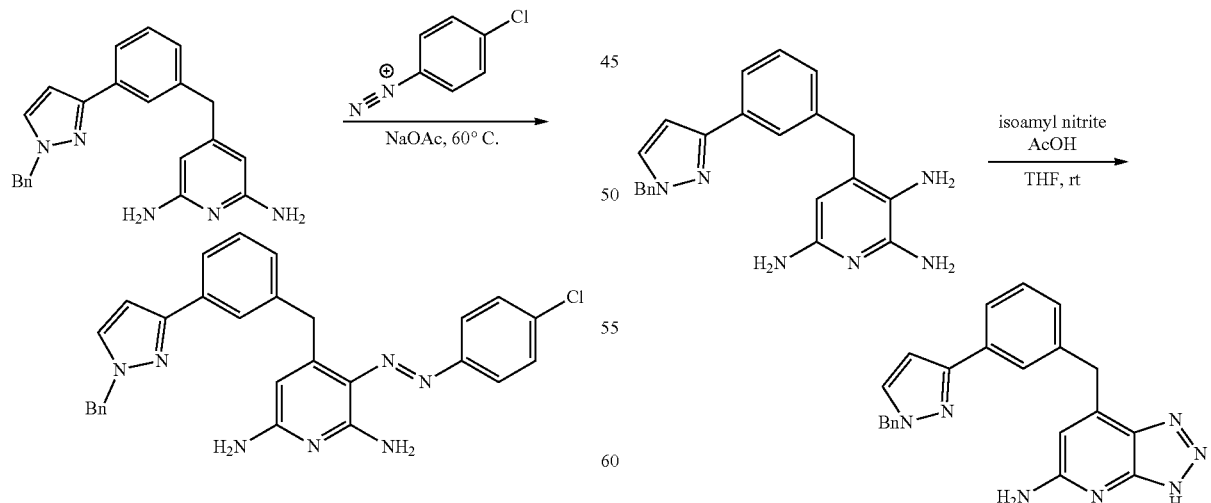

A solution of 4-chlorobenzenediazonium chloride salt (0.180 g, 1.03 mmol) was poured into a solution of 4-(3-(1-benzyl-1H-pyrazol-3-yl)benzyl)pyridine-2,6-diamine (48b, 0.365 g, 1.03 mmol) in water (10 mL)/EtOAc (10 mL) (+few drops of MeOH to ensure homogeneity). After 60 min, sodium acetate (0.379 g, 4.62 mmol) was added, and the reaction mixture was allowed to stir overnight. The reaction mixture was partitioned between water and EtOAc. The organic layer was concentrated and purified by silica gel chromatography to furnish the title compound (48c, 0.452 g, 0.915 mmol, 89% yield). MS(ESI) m/z 494.0 (M+H).

Intermediate 48d: 4-(3-(1-Benzyl-1H-pyrazol-3-yl)benzyl)pyridine-2,3,6-triamine

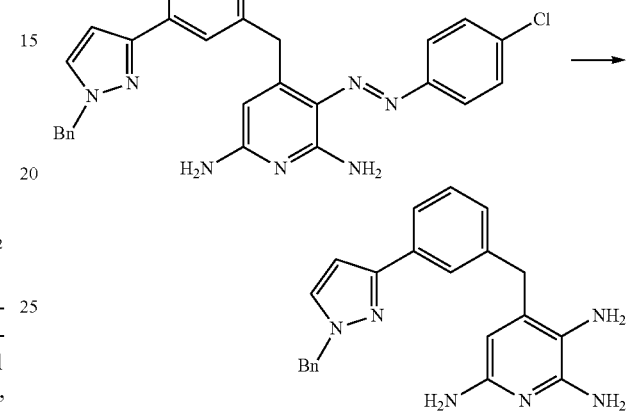

To a solution of (E)-4-(3-(1-benzyl-1H-pyrazol-3-yl)benzyl)-3-((4-chlorophenyl)diazenyl)pyridine-2,6-diamine (48c, 0.422 g, 0.854 mmol) in EtOH (8.5 mL) was added acetic acid (0.15 mL, 2.6 mmol) and zinc powder (0.168 g, 2.56 mmol), and the reaction mixture was heated to 60° C. for 20 min, then filtered through CELITE® and concentrated. The residue was then purified by silica gel chromatography to furnish the title compound (48d, 0.241 g, 0.651 mmol, 76% yield), which was used without delay.

Example 48

To a solution of 4-(3-(1-benzyl-1H-pyrazol-3-yl)benzyl)pyridine-2,3,6-triamine (48d, 0.241 g, 0.651 mmol) in THF (13 mL) was added AcOH (0.04 mL, 0.7 mmol) and isoamyl nitrite (0.079 mL, 0.59 mmol), and the reaction mixture was allowed to stir overnight. The reaction mixture was quenched with 1 eq 7N NH₃ in MeOH. After 1 h the mixture was concentrated and purified by preparative HPLC to furnish the title compound (0.0857 g, 0.156 mmol, 23.9% yield) as the TFA salt. MS(ESI) m/z 382.2 (M+H). ¹H NMR (500 MHz, DMSO-d₆) δ 8.26 (s, 1H), 7.90 (d, J=0.5 Hz, 1H), 7.60 (s, 1H), 7.49-7.09 (m, 8H), 6.32 (br. s., 1H), 5.35 (s, 2H), 4.28 (s, 2H). Analytical HPLC Col A: 4.93 min, 90%; Col B: 5.24 min, 89%. LC RT=5.33 min (Method A).

For all diamines prepared below according to the procedures outlined in Schemes 4 and 5, the resulting diamines 3-1 were converted to the corresponding examples of the general formula (I) according to the previously described general procedures in the sequence outlined originally in Scheme 3: diamine intermediates 3-1 were diazotized according to the General Diazine Formation Procedure to furnish diazine pyridine 3-2. Diazine pyridine 3-2 was reduced either according to General Zinc Diazine Reduction Procedure or General Hydrazine Diazine Reduction Procedure to furnish triamine 3-3 which was immediately treated according to the General Triazole Formation Procedure to furnish compounds of the general formula (I).

Example 49: 7-(3-(Benzyloxy)benzyl)-3H-[1,2,3]triazolo[4,5-b]pyridin-5-amine

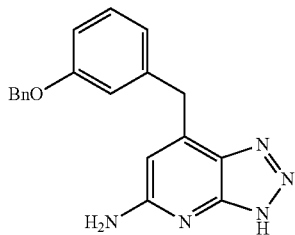 [SMILES: Nc1cc(Cc2cccc(OCc3ccccc3)c2)c2nn[nH]c2n1]

Example 49 as prepared according to procedures outlined in Scheme 4.

Intermediate 49a:
2,6-(2,5-Dimethylpyrrol-1-yl)-pyridine

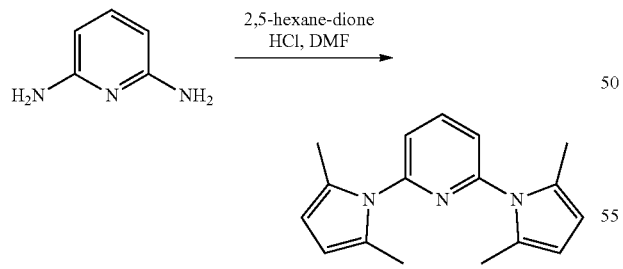

Pyridine-2,6-diamine (2.00 g, 18.3 mmol) was dissolved in HCl (10.3 mL, 41.2 mmol) with sufficient MeOH added to ensure homogeneity. The solution was concentrated using MeOH as an azeotrope, then the solid residue was triturated with ether and placed under vacuum overnight. The material was diluted in DMF (37 mL), then treated with hexane-2,5-dione (6.45 mL, 55.0 mmol) and MgSO₄ (11 g, 92 mmol), and allowed to stir for 1 h at 120° C. The solution was then filtered and partitioned between water and EtOAc. The organic layer was extracted with water and brine, dried over Na₂SO₄, filtered through a silica gel plug and concentrated. The residue was triturated with a minimal quantity of ether to furnish the title compound (49a, 2.062 g, 7.77 mmol, 42.4% yield). MS(ESI) m/z 266.1 (M+H). ¹H NMR (500 MHz, CDCl₃) δ 7.98 (t, J=7.7 Hz, 1H), 7.27 (d, J=8.0 Hz, 2H), 5.92 (s, 4H), 2.17 (s, 12H).

Intermediate 49b:
2,6-(2,5-Dimethylpyrrol-1-yl)-pyridylboronic acid

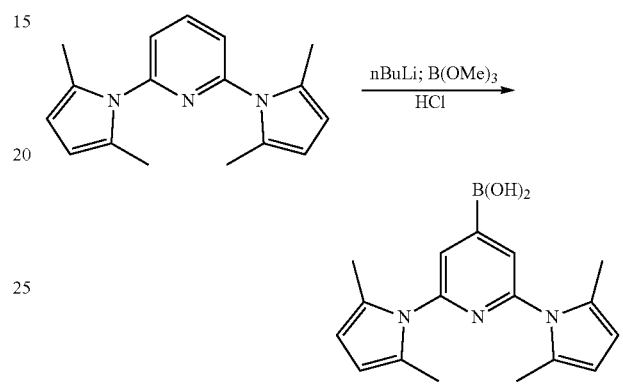

A solution of 2,6-bis(2,5-dimethyl-1H-pyrrol-1-yl)pyridine (49a, 1.00 g, 3.77 mmol) in THF (19 mL) was cooled to 0° C. and treated with nBuLi (1.80 mL, 4.15 mmol) added slowly. After 10 min the solution was transferred to a solution of trimethyl borate (0.55 mL, 4.9 mmol) in ether (19 mL) and allowed to stir for 1 h while warming to rt. The solution was cooled to 0° C. and treated with HCl (1.8 mL, 5.5 mmol), then stirred for 10 min. The ether layer was then dried over Na₂SO₄, filtered and concentrated to furnish the title compound (49b, 1.17 g, 3.78 mmol, 100% yield). ¹H NMR (500 MHz, DMSO-d₆) δ 7.67 (s, 2H), 5.83 (s, 4H), 2.06 (s, 12H).

Intermediate 49c: 4-(3-(Benzyloxy)benzyl)-2,6-bis(2,5-dimethyl-1H-pyrrol-1-yl)pyridine

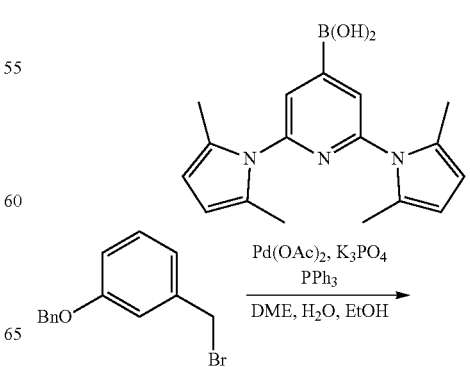

-continued

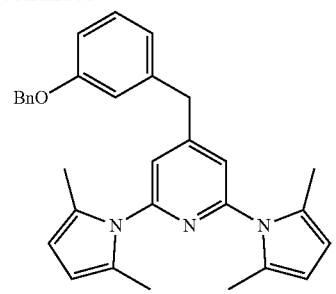

(2,6-Bis(2,5-dimethyl-1H-pyrrol-1-yl)pyridin-4-yl)boronic acid (49b, 0.500 g, 0.809 mmol), 1-(benzyloxy)-3-(bromomethyl)benzene (0.336 g, 1.21 mmol), palladium acetate (0.018 g, 0.081 mmol), phosphoric acid, potassium salt (0.343 g, 1.62 mmol) and triphenylphosphine (0.042 g, 0.16 mmol) were slurried in DME (5 mL)/ethanol (0.5 mL)/water (0.5 mL) and blanketed under argon. The slurry was heated to 80° C. and stirred overnight. The reaction mixture was partitioned between EtOAc and water. The organic layer was concentrated, and the residue was purified by silica gel chromatography to furnish the title compound (49c, 0.514 g) contaminated with residual impurities. MS(ESI) m/z 462.1 (M+H).

Intermediate 49d:
4-(3-(Benzyloxy)benzyl)pyridine-2,6-diamine

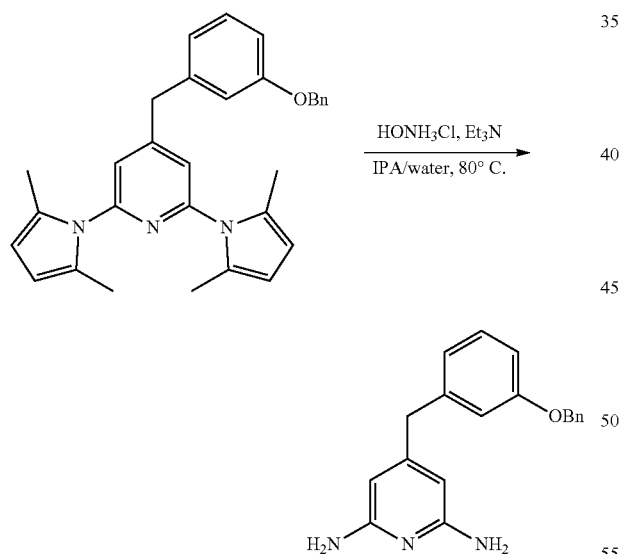

A slurry of 4-(3-(benzyloxy)benzyl)-2,6-bis(2,5-dimethyl-1H-pyrrol-1-yl)pyridine (49c, 0.514 g, 1.11 mmol), hydroxylamine hydrochloride (1.55 g, 22.3 mmol), and Et$_3$N (1.55 mL, 11.1 mmol) in iPrOH (8.9 mL)/water (2.2 mL) was heated to 80° C. in a sealed vessel overnight. The solution was extracted from sat. aq. bicarbonate with EtOAc. The organic layer was concentrated, and the residue was purified by silica gel chromatography to furnish the title compound (49d, 0.235 g, 0.770 mmol, 69.1% yield). MS(ESI) m/z 306.1 (M+H).

Intermediate 49e: (E)-4-(3-(Benzyloxy)benzyl)-3-((4-chlorophenyl)diazenyl)pyridine-2,6-diamine

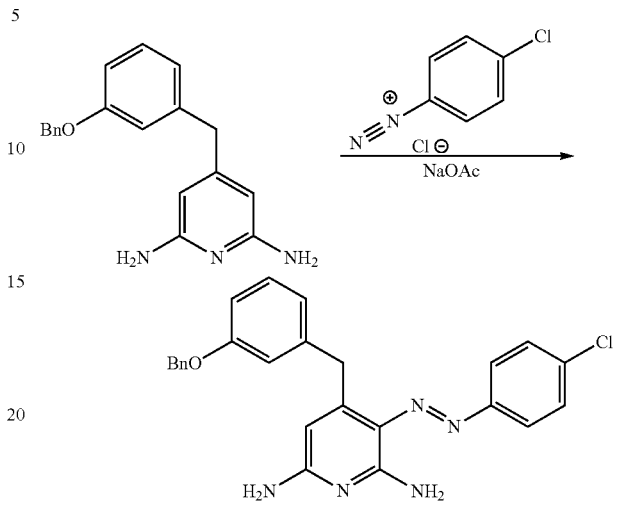

A solution of 4-chlorobenzenediazonium chloride salt (49d, 0.135 g, 0.770 mmol) was poured into a solution of 4-(3-(benzyloxy)benzyl)pyridine-2,6-diamine (0.235 g, 0.770 mmol) in water (7.7 mL)/EtOAc (7.7 mL). After 60 min, sodium acetate (0.284 g, 3.46 mmol) was added, and the reaction mixture was allowed to stir overnight. The reaction mixture was partitioned between water and EtOAc. The organic layer was concentrated and purified by silica gel chromatography to furnish the title compound (49e, 0.085 g, 0.19 mmol, 25% yield). MS(ESI) m/z 444.0 (M+H).

Intermediate 49f:
4-(3-(Benzyloxy)benzyl)pyridine-2,3,6-triamine

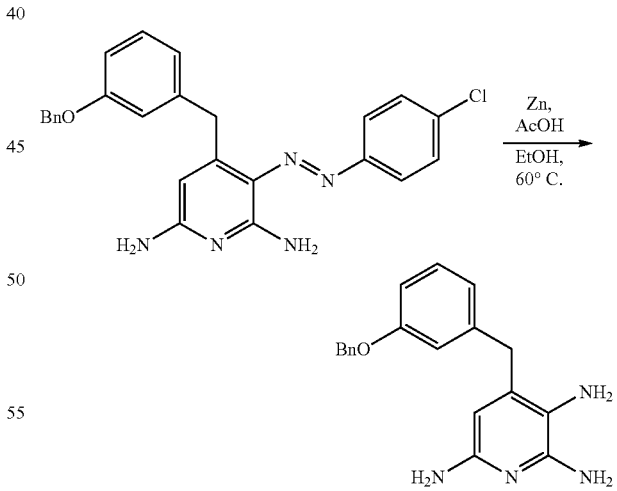

To a solution of (E)-4-(3-(benzyloxy)benzyl)-3-((4-chlorophenyl)diazenyl)pyridine-2,6-diamine (49e, 0.085 g, 0.19 mmol) in EtOH (1.9 mL) was added acetic acid (0.03 mL, 0.6 mmol) and zinc powder (0.038 g, 0.57 mmol). The reaction mixture was heated to 60° C. for 20 min, then filtered through CELITE® and concentrated. The residue was purified by silica gel chromatography to furnish the title compound (49f, 0.030 g, 0.094 mmol, 49% yield).

Example 49

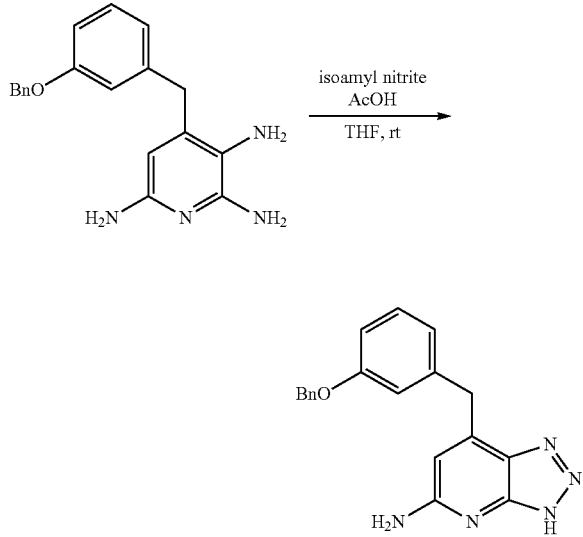 [SMILES: Nc1cc(Cc2cccc(OCc3ccccc3)c2)c(N)c(N)n1 ; Nc1cc(Cc2cccc(OCc3ccccc3)c2)c2nn[nH]c2n1]

To a solution of 4-(3-(benzyloxy)benzyl)pyridine-2,3,6-triamine (49f, 0.030 g, 0.094 mmol) in THF (0.9 mL) was added AcOH (5 µl, 0.09 mmol) and isoamylnitrite (0.011 mL, 0.084 mmol), and the reaction mixture was stirred overnight. The reaction mixture was concentrated, and the residue was purified by preparatory HPLC to furnish the title compound (0.0054 g, 0.016 mmol, 17% yield). MS(ESI) m/z 332.1 (M+H). $^1$H NMR (500 MHz, DMSO-$d_6$) δ 7.46-7.42 (m, 2H), 7.41-7.36 (m, 2H), 7.36-7.30 (m, 1H), 7.25 (t, J=7.8 Hz, 1H), 7.03 (s, 1H), 6.94 (d, J=7.4 Hz, 1H), 6.90 (d, J=8.3 Hz, 1H), 6.32 (br. s., 1H), 5.07 (s, 2H), 4.23 (br. s., 2H). Analytical HPLC Col A: 6.631 min, 97.4%; Col B: 6.973 min, 99.4%. LC RT=6.36 min (Method A).

Example 50 (Table 2) was prepared according the procedures described for Example 49 described above by using the appropriate benzyl halide, which was prepared from the corresponding alcohol according to standard methods.

Example 51: 7-((6-Methoxypyridin-2-yl)methyl)-3H-[1,2,3]triazolo[4,5-b]pyridin-5-amine (TFA Salt)

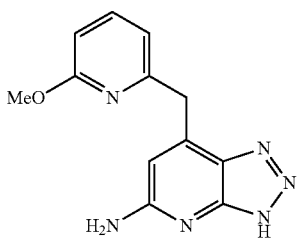 [SMILES: COc1cccc(Cc2cc(N)nc3[nH]nnc23)n1]

Example 51 as prepared according to the procedures described in Scheme 5:

Intermediate 51a: 2,6-(2,5-Dimethylpyrrol-1-yl)-4-bromo-pyridine

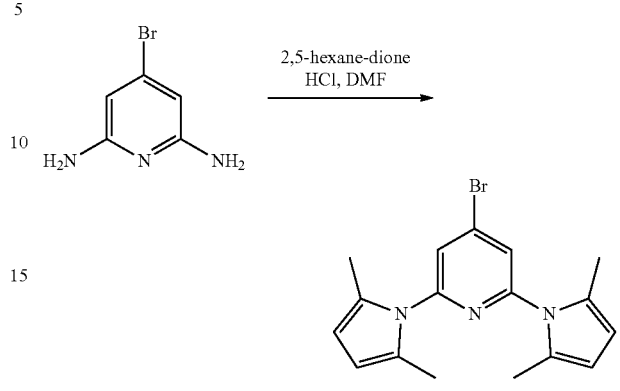

4-Bromopyridine-2,6-diamine (20 g, 106 mmol) was suspended in iPrOH (100 mL) and conc HBr (29.9 mL, 266 mmol). The mixture was stirred at rt under argon overnight. The precipitated hydrobromide salt was collected by filtration and washed with a minimal amount of iPrOH and dried under vacuum. The filtrate was evaporated, and the residue was dried under vacuum for several hours then triturated with Et$_2$O three times. The resulting solid was dried in vacuo and combined with the first crop for a total of 26.9 g of yellow 4-bromopyridine-2,6-diamine, hydrobromide. 4-bromopyridine-2,6-diamine, hydrobromide (26.9 g, 100 mmol) was taken up in DMF (200 mL), and 2,5-hexanedione (36.7 mL, 300 mmol) and MgSO$_4$ (60.2 g, 500 mmol) were added. The mixture was heated under argon at 120° C. for ~4 hr, then cooled to rt and filtered. The solid was washed thoroughly with EtOAc. The combined filtrate and washings were extracted with aq. sat. NaHCO$_3$, 10% aq LiCl and brine, then dried over MgSO$_4$, filtered, and evaporated. The residue was taken up in DCM, and absorbed onto a silica gel pad, which was then eluted with 10% Et$_2$O in hexanes until most of the orange color had eluted. The eluent was evaporated and the solid dried thoroughly in vacuo to provide 2,6-(2,5-dimethylpyrrol-1-yl)-4-bromo-pyridine (51a, 25.1 g, 72.7%). MS(ESI) m/z: 344.0 (M+H)$^+$ $^1$H NMR (500 MHz, CDCl$_3$) δ 7.40 (s, 2H), 5.91 (s, 4H), 2.18 (s, 12H).

General Lithiation/Addition Procedure:

A solution of nBuLi (1.6 M in hexanes, 1.05 eq.) is added dropwise at −78° C. over 2-3 min to a solution of 5-1 or 4-2 (1.05 eq) in THF in an oven-dried flask with stirring under argon. The mixture is stirred for a total of 10 min at −78° C. followed by rapid addition of a solution of the appropriate aldehyde (1.0 eq) in 3-5 mL THF. After stirring for an additional 30 min at −78° C., the reaction mixture is allowed to warm to rt, stirred for 1-1.5 h then quenched with sat. aq. NH$_4$Cl, diluted with water and extracted with EtOAc. Combined extracts are washed with brine, dried over Na$_2$SO$_4$, filtered and evaporated to furnish 5-2 which may or may not be used as is. Alternatively chromatography on silica gel provides pure alcohol intermediates 5-2.

General Alcohol Acetylization Procedure:

Alcohols 5-2 (1.0 eq) are taken up in DCM and treated at rt with pyridine (1.2 eq), acetic anhydride (1.2 eq) and DMAP (0.2 eq). Reaction mixtures are stirred from 1-24 h, then diluted with additional DCM, washed with sat. aq. NaHCO$_3$ and brine, dried over Na$_2$SO$_4$, filtered and evaporated. Acetate products 5-3 are purified by chromatography on silica gel or used directly without purification in next step.

General Samarium Diiodide Reduction Procedure:

Acetates 5-3 are taken up in a few mL of THF and transferred to an argon-flushed flask sealed with a rubber septum. iPrOH or tBuOH (1.5 eq) is added via syringe, and the contents of the flask are degassed by careful evacuation and flushing with argon. A solution of SmI$_2$ (0.1 M in THF, 4 eq) is then added dropwise over 10-20 min, resulting in a dark blue solution, which is stirred under argon for 24-72 h at rt. The reaction mixture is quenched by addition of water or MeOH and brine and extracted with EtOAc. The combined extracts are washed with brine, dried over Na$_2$SO$_4$, filtered and evaporated. Product 4-4 is purified by silica gel chromatography or used directly in next step. Intermediate 4-4 was deprotected according to the General Bis-pyrrole Deprotection Procedure to furnish diaminopyridine 3-1, which was elaborated to compounds of the general formula (I) according to the general procedures outlined in General Route 3 (Scheme 3).

Intermediate 51b: (2,6-Bis(2,5-dimethyl-1H-pyrrol-1-yl)pyridin-4-yl)(6-methoxypyridin-2-yl)methanol

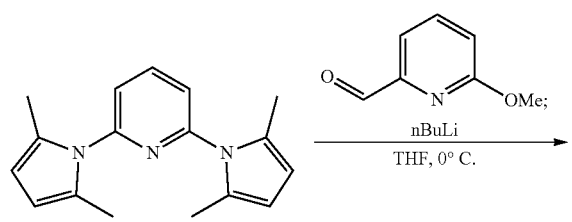

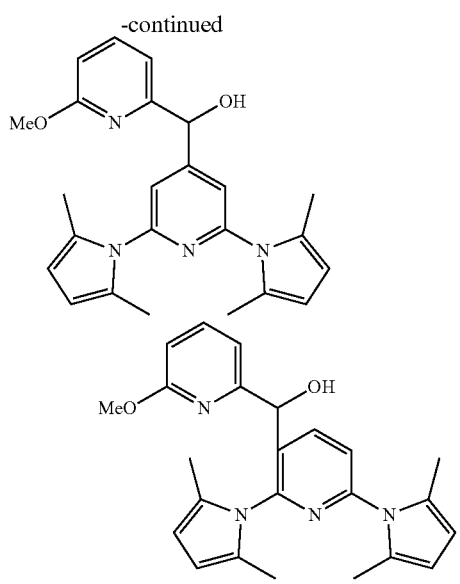

A solution of 2,6-bis(2,5-dimethyl-1H-pyrrol-1-yl)pyridine (49a, 0.730 g, 2.75 mmol) in THF (12.5 mL) was treated with nBuLi (1.15 mL, 2.88 mmol) at 0° C. and stirred for 15-20 min. To this solution was added 6-methoxypicolinaldehyde (0.343 g, 2.50 mmol). After 1 h, the reaction mixture was extracted from water with EtOAc, concentrated and used as is as the title compound (51b, 1.006 g, 2.500 mmol, contaminated with pyridin-3yl regioisomer). MS(ESI) m/z 403.1 (M+H).

Intermediate 51c: (2,6-Bis(2,5-dimethyl-1H-pyrrol-1-yl)pyridin-4-yl)(6-methoxypyridin-2-yl)methylacetate

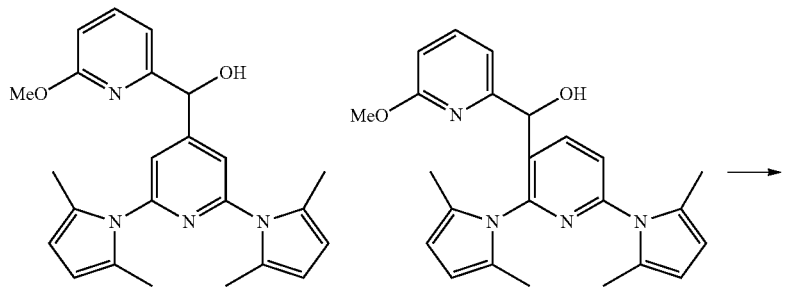

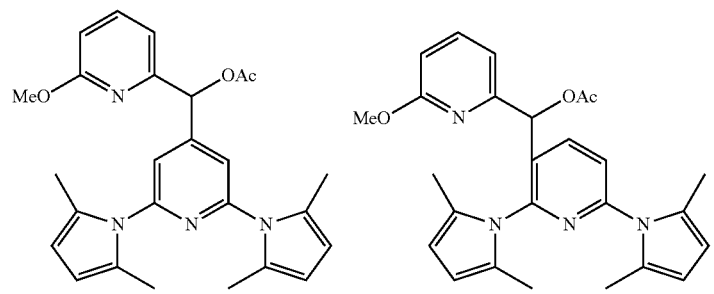

To a solution of (2,6-bis(2,5-dimethyl-1H-pyrrol-1-yl)pyridin-4-yl)(6-methoxypyridin-2-yl)methanol (51b, 1.006 g, 2.5 mmol) in DCM (12.5 mL) was added acetic anhydride (0.283 mL, 3.00 mmol), DMAP (0.031 g, 0.25 mmol) and Et₃N (0.418 mL, 3.00 mmol), and the reaction mixture was allowed to stir overnight. The reaction mixture was partitioned between sat aq NaHCO₃ and EtOAc. The organics were concentrated, and the residue was purified by silica gel chromatography to furnish the title compound (51c, 0.638 g, 1.43 mmol, contaminated with pyridin-3yl regioisomer). MS(ESI) m/z 445.0 (M+H).

Intermediate 51d: 2,6-Bis(2,5-dimethyl-1H-pyrrol-1-yl)-4-((6-methoxypyridin-2-yl)methyl)pyridine

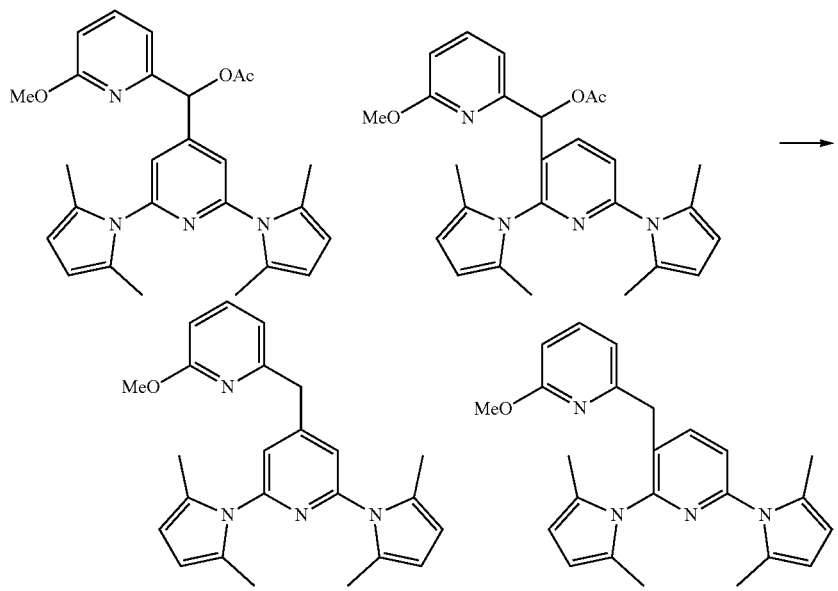

To a solution of (2,6-bis(2,5-dimethyl-1H-pyrrol-1-yl)pyridin-4-yl)(6-methoxypyridin-2-yl)methylacetated (51c, 0.638 g, 1.43 mmol) in THF (14.4 mL) under argon was added iPrOH (0.166 mL, 2.15 mmol) and SmI₂ (57.4 mL, 5.74 mmol), and the reaction mixture was stirred overnight. The reaction mixture was partitioned between brine and EtOAc. The organic layer was concentrated, and the residue was purified by silica gel chromatography to furnish the title compound (51d, 0.448 g, 1.159 mmol, contaminated with pyridin-3yl regioisomer). MS(ESI) m/z 387.1 (M+H).

Intermediate 51e: 4-((6-Methoxypyridin-2-yl)methyl)pyridine-2,6-diamine

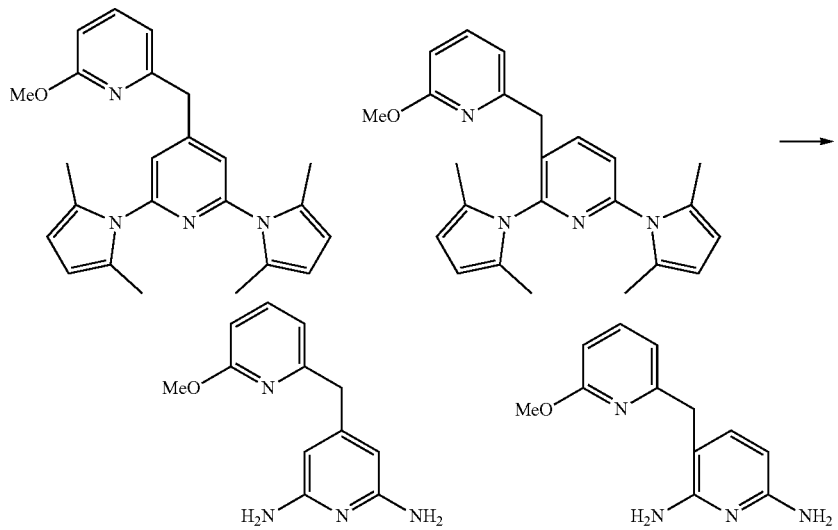

A slurry of 2,6-bis(2,5-dimethyl-1H-pyrrol-1-yl)-4-((6-methoxypyridin-2-yl)methyl)pyridine (51d, 0.448 g, 1.16 mmol), hydroxylamine hydrochloride (1.611 g, 23.18 mmol), Et$_3$N (1.616 mL, 11.59 mmol) in iPrOH (9.3 mL)/water (2.3 mL) was prepared and heated to 80° C. in a sealed vessel overnight. The reaction mixture was partitioned between a saturated aqueous sodium bicarbonate solution and EtOAc. The organic layer was concentrated, and the residue was purified by silica gel chromatography to furnish the title compound (51e, 0.474 g contaminated with pyridin-3yl regioisomer+other impurities). MS(ESI) m/z 231.1 (M+H).

Intermediate 51f: (E)-3-((4-Chlorophenyl)diazenyl)-4-((6-methoxypyridin-2-yl)methyl)pyridine-2,6-diamine Intermediate 51g: 4-((6-Methoxypyridin-2-yl)methyl)pyridine-2,3,6-triamine

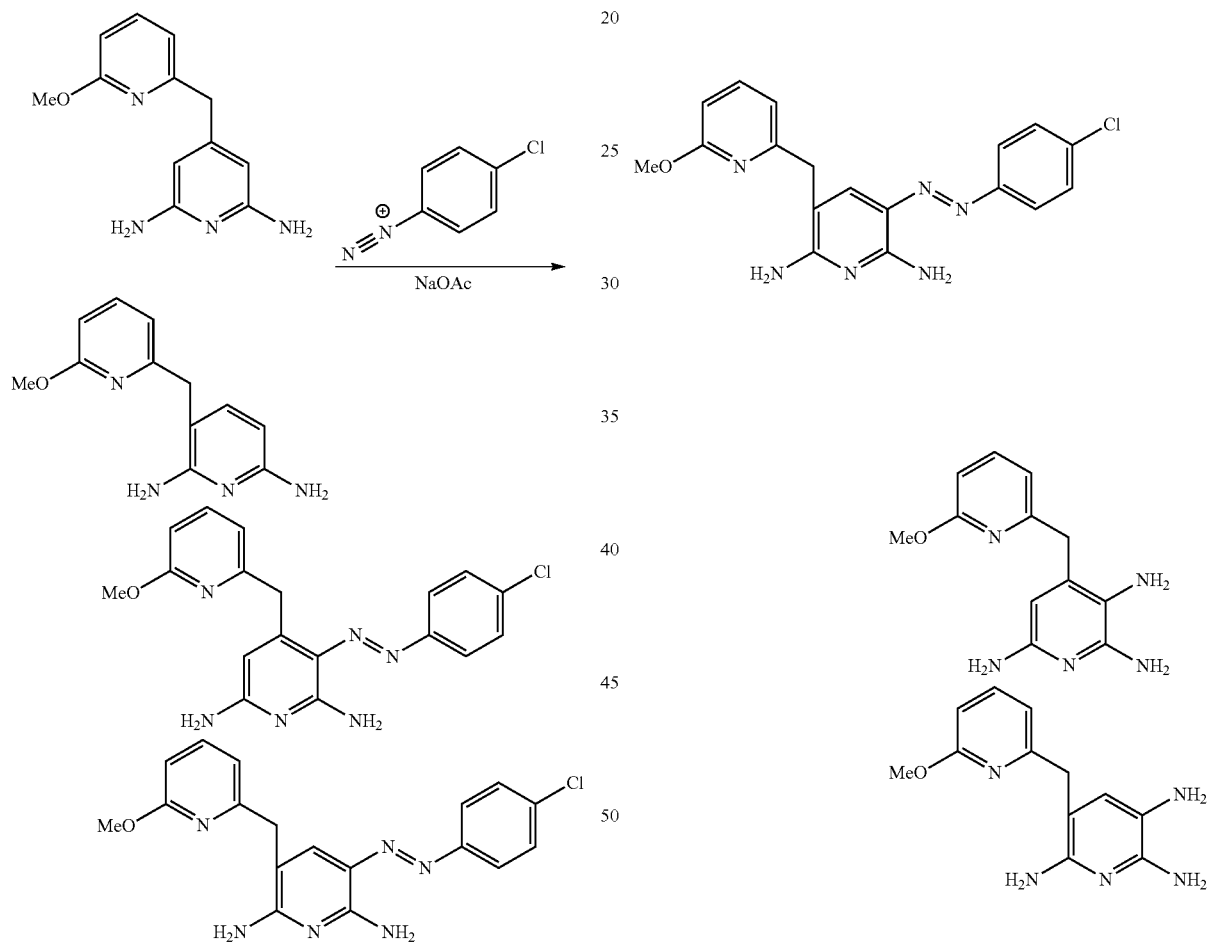

A solution of 4-chlorobenzenediazonium chloride salt (0.360 g, 2.06 mmol) was poured into a solution of 4-((6-methoxypyridin-2-yl)methyl)pyridine-2,6-diamine (51e, 0.474 g, 2.06 mmol) in water (10.29 mL)/EtOAc (10.29 mL) containing a few drops of MeOH. After 60 min, sodium acetate (0.760 g, 9.26 mmol) was added, and the reaction mixture was allowed to stir overnight. The reaction mixture was partitioned between water and EtOAc. The organic layer was concentrated and purified by silica gel chromatography to furnish the title compound (51f, 0.302 g, 0.819 mmol). MS(ESI) m/z 369.0 (M+H).

To a solution of (E)-3-((4-chlorophenyl)diazenyl)-4-((6-methoxypyridin-2-yl)methyl)pyridine-2,6-diamine (51f, 0.302 g, 0.819 mmol) in EtOH (8.19 mL) was added acetic acid (0.141 mL, 2.46 mmol) and zinc powder (0.161 g, 2.46 mmol), and the reaction mixture was heated to 60° C. for 20 min, then filtered through CELITE® and concentrated. The residue was then purified by silica gel chromatography to furnish the title compound (51g, 0.130 g, 0.530 mmol, 64.7% yield).

Example 51

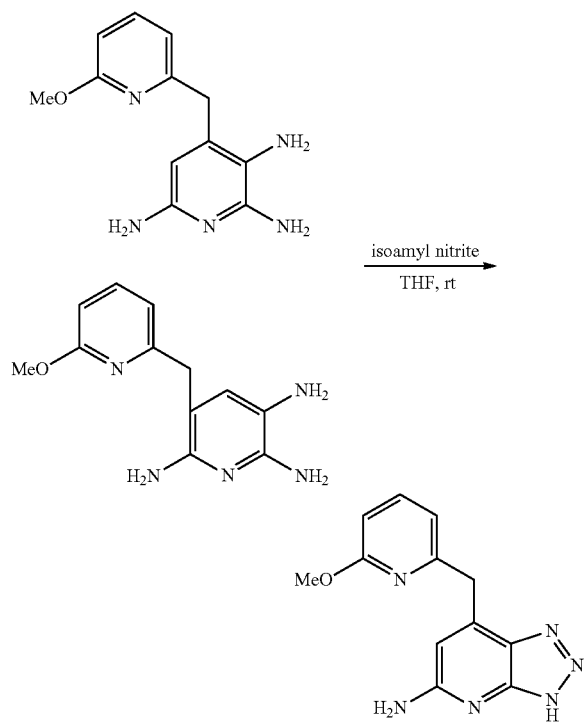

To a solution of 4-((6-methoxypyridin-2-yl)methyl)pyridine-2,3,6-triamine (51 g, 0.130 g, 0.530 mmol) in THF (11 mL) was added isoamylnitrite (0.064 mL, 0.48 mmol), and the reaction mixture was allowed to stir overnight. The reaction mixture was quenched with 1 mL 7N $NH_3$ in MeOH then concentrated and purified by preparative HPLC to furnish the title compound as a single isomer (0.0217 g, 0.0570 mmol, 10.7% yield) isolated as the TFA salt. MS(ESI) m/z 257.1 (M+H). $^1$H NMR (500 MHz, methanol-$d_4$) δ 7.61 (dd, J=8.3, 7.4 Hz, 1H), 6.96 (d, J=6.9 Hz, 1H), 6.66 (d, J=8.3 Hz, 1H), 6.52 (s, 1H), 4.38 (s, 2H), 3.87 (s, 3H). LC RT=3.82 min (Method A).

Examples 52-58 (Table 2) and Examples 59-66 below were prepared similarly to Example 51 according to the procedures outlined above from intermediate 5-1 or 4-2 and the corresponding aldehydes (Examples 52-58), which are either commercially available or were prepared as described using a combination of the procedures outlined below (Examples 59-66). Examples 52-56 and 58-68 were isolated as the TFA salt.

The following general procedures were used for the preparation of aldehyde intermediates employed in the synthesis of Examples 59-66:

General Indole/Indazole Alkylation Procedure:

To a suspension of NaH (60% in mineral oil, 1.1 eq) in DMF cooled to 0° C. in an ice/salt water bath with stirring under argon is added dropwise a solution of the appropriate pyrazole, indole or indazole compound (1 eq) in DMF. The mixture is stirred for 10-15 min at 0° C., followed by dropwise addition of 1.15 eq. of an alkyl, benzyl or cycloalkylbromide, mesylate or chloride neat or dissolved in a small amount of DMF. Stirring at 0° C. is continued for 30-60 min, then at rt overnight or until the reaction is complete by LCMS or TLC. The reaction mixture is diluted with water and extracted with EtOAc. Combined organic extracts are washed with water or 10% LiCl solution, and then with brine, dried over anh. $Na_2SO_4$, filtered and evaporated. Purification by chromatography on silica gel provides the alkylated products.

General Carboxylate Reduction Procedure:

A 1M solution of DIBAL-H in DCM (2.5 eq) is added at 0° C. to a solution of an appropriately substituted ethyl pyrazole-4-carboxylate or methyl indazole-4-carboxylate (1 eq) in DCM (0.2 M), and the reaction mixture is stirred at 0° C. or rt until the reduction is complete. The reaction mixture is quenched either by addition of saturated $NH_4Cl$ solution and dilution with 1M HCl, or alternately, for basic compounds that can form water soluble HCl salts, by stirring with a saturated solution of Rochelle's salt for 20 min, and followed by extraction with EtOAc. The combined extracts are washed with brine, dried over $Na_2SO_4$, filtered and concentrated to the crude alcohol product that is used without further purification.

General Benzylic Alcohol Oxidation Procedure:

PCC (1.5 eq) added in one portion to a solution of the appropriately substituted hydroxymethylpyrazole or indazole (1 eq) in DCM (0.1 M) at 0° C. The mixture was stirred for 15 min at 0° C., then at rt for 1-3 h or until no more starting alcohol remains. The reaction mixture was diluted with additional DCM and filtered through a silica gel plug which was washed thoroughly with DCM. The filtrate was concentrated and desired aldehyde product isolated by chromatography on silica gel.

Example 59: 7-((1-Benzyl-1H-indol-4-yl)methyl)-3H-[1,2,3]triazolo[4,5-b]pyridin-5-amine

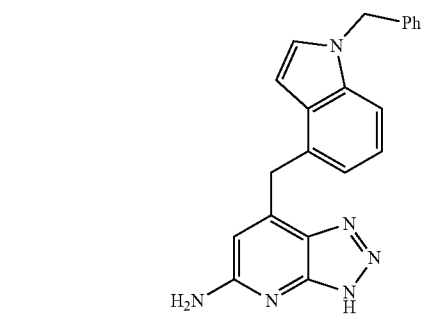 [SMILES: Nc1cc(Cc2cccc3c2ccn3Cc2ccccc2)c2nn[nH]c2n1]

From 1-benzylindole-4-carboxaldehyde prepared from indole-4-carboxaldehyde by alkylation with benzyl bromide following General Indole/Indazole Alkylation Procedure. Light yellow solid MS(ESI) m/z: 355.3 (M+H)$^+$. $^1$H NMR (500 MHz, DMSO-$d_6$) δ 7.49 (d, J=3.0 Hz, 1H), 7.37 (d, J=8.0 Hz, 1H), 7.34-7.28 (m, 2H), 7.27-7.19 (m, 3H), 7.07 (t, J=7.7 Hz, 1H), 7.00 (d, J=6.9 Hz, 1H), 6.58-6.51 (m, 1H), 6.28 (br. s., 1H), 5.41 (s, 2H), 4.50 (s, 2H). Analytical HPLC Col. A: 6.90 min, 96.5%; Col. B: 7.47 min, 93.7%. LC RT=6.90 min (Method A).

Example 60: 7-((1-Ethyl-1H-indol-4-yl)methyl)-3H-[1,2,3]triazolo[4,5-b]pyridin-5-amine

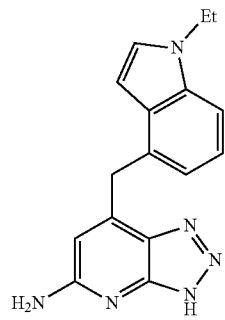 [SMILES: CCn1ccc2c(Cc3cc(N)nc4[nH]nnc34)cccc21]

From 1-ethylindole-4-carboxaldehyde prepared from indole-4-carboxaldehyde by alkylation with ethylbromide following General Indole/Indazole Alkylation Procedure. Light tan solid. MS(ESI) m/z: 293.2 (M+H)$^+$. $^1$H NMR (500 MHz, DMSO-d$_6$) δ 7.38 (d, J=8.3 Hz, 1H), 7.36 (d, J=3.0 Hz, 1H), 7.13-7.07 (m, 1H), 7.00 (d, J=6.9 Hz, 1H), 6.46 (dd, J=3.2, 0.7 Hz, 1H), 6.29 (br. s., 1H), 4.49 (s, 2H), 4.19 (q, J=7.2 Hz, 2H), 1.35 (t, J=7.3 Hz, 3H). Analytical HPLC Col. A: 5.75 min, 99%; Col. B: 6.18 min, 92.2%. LC RT=5.75 min (Method A).

Example 61: 7-((1-([1,1'-Biphenyl]-3-ylmethyl)-1H-indol-4-yl)methyl)-3H-[1,2,3]triazolo[4,5-b]pyridin-5-amine

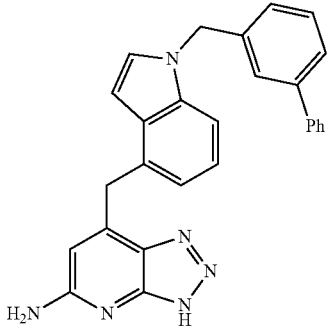 [SMILES: Nc1cc(Cc2cccc3c2ccn3Cc2cccc(-c3ccccc3)c2)c2nn[nH]c2n1]

From 1-(3-phenyl)benzylindole-4-carboxaldehyde prepared from indole-4-carboxaldehyde by alkylation with 3-phenylbenzylbromide following General Indole/Indazole Alkylation Procedure. Pale yellow solid. MS(ESI) m/z: 431.2 (M+H)$^+$. $^1$H NMR (500 MHz, DMSO-d$_6$) δ 7.62-7.57 (m, 3H), 7.56 (d, J=3.0 Hz, 1H), 7.53 (d, J=7.7 Hz, 1H), 7.49-7.41 (m, 3H), 7.40-7.34 (m, 2H), 7.18 (d, J=7.7 Hz, 1H), 7.08 (t, J=7.7 Hz, 1H), 6.99 (d, J=6.9 Hz, 1H), 6.58-6.53 (m, 1H), 6.30 (br. s., 1H), 5.48 (s, 2H), 4.49 (s, 2H). Analytical HPLC Col. A: 8.01 min, >99%; Col. B: 8.99 min, >99%. LC RT=8.01 min (Method A).

Example 62: 7-((1-(3-Benzylbenzyl)-1H-indol-4-yl)methyl)-3H-[1,2,3]triazolo[4,5-b]pyridin-5-amine

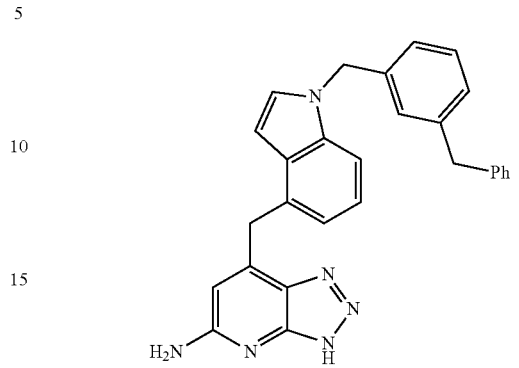

From 1-(3-benzyl)benzylindole-4-carboxaldehyde prepared from indole-4-carboxaldehyde by alkylation with 3-benzylbenzylbromide/NaH. Benzyl bromide prepared from corresponding benzyl alcohol with MsCl, LiBr. Off-white solid. MS(ESI) m/z: 444.9 (M+H)$^+$. $^1$H NMR (500 MHz, DMSO-d$_6$) δ 7.45 (d, J=3.3 Hz, 1H), 7.33 (d, J=8.3 Hz, 1H), 7.29-7.23 (m, 2H), 7.21 (d, J=2.8 Hz, 1H), 7.20-7.15 (m, 4H), 7.09 (d, J=7.7 Hz, 1H), 7.07-7.02 (m, 1H), 7.01-6.94 (m, 2H), 6.52 (dd, J=3.2, 0.7 Hz, 1H), 6.33-6.17 (m, 1H), 5.35 (s, 2H), 4.48 (s, 2H), 3.88 (s, 2H). Analytical HPLC Col. A: 8.27 min, >99%; Col. B: 9.26 min, >99%. LC RT=8.27 min (Method A).

Example 63: 7-((1-(3-(Benzyloxy)benzyl)-1H-indol-4-yl)methyl)-3H-[1,2,3]triazolo[4,5-b]pyridin-5-amine

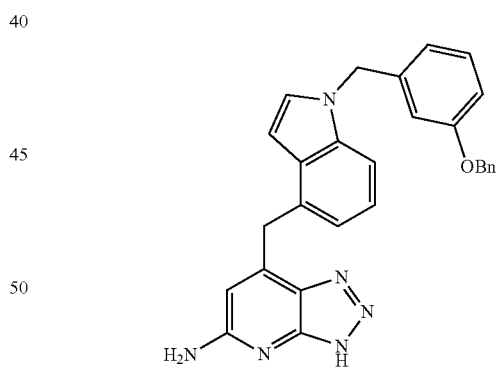

From 1-(3-benzyloxy)benzylindole-4-carboxaldehyde prepared from indole-4-carboxaldehyde by alkylation with 3-benzyloxybenzylbromide/NaH. Benzyl bromide prepared from corresponding benzyl alcohol with MsCl, LiBr. Off-white solid. MS(ESI) m/z: 460.9 (M+H)$^+$. $^1$H NMR (500 MHz, DMSO-d$_6$) 7.48 (d, J=3.0 Hz, 1H), 7.41-7.33 (m, 5H), 7.33-7.28 (m, 1H), 7.25-7.16 (m, 1H), 7.10-7.03 (m, 1H), 6.99 (d, J=6.9 Hz, 1H), 6.92-6.84 (m, 2H), 6.77 (d, J=7.7 Hz, 1H), 6.56-6.51 (m, 1H), 6.25 (br. s., 1H), 5.36 (s, 2H), 5.03 (s, 2H), 4.48 (s, 2H). Analytical HPLC Col. A: 7.95 min, >99%; Col. B: 8.25 min, 99%. LC RT=7.95 min (Method A).

Example 64: 7-((1-(3-Fluorobenzyl)-1H-indol-4-yl)methyl)-3H-[1,2,3]triazolo[4,5-b]pyridin-5-amine

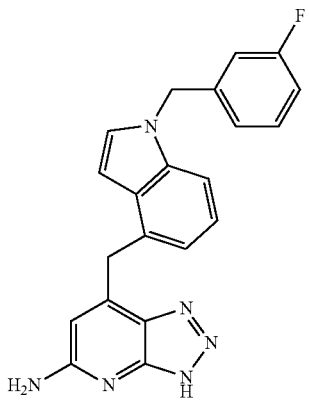 [SMILES: Nc1cc(Cc2cccc3c2ccn3Cc2cccc(F)c2)c2nn[nH]c2n1]

From 1-(3-fluorobenzyl)-1H-indole-4-carboxaldehyde prepared by alkylation of indole-4-carboxaldehyde with 3-fluorobenzylbromide following General Indole/Indazole Alkylation Procedure. White solid. MS(ESI) m/z: 372.9 (M+H)+. $^1$H NMR (500 MHz, DMSO-$d_6$) δ 7.51 (d, J=3.0 Hz, 1H), 7.41-7.31 (m, 2H), 7.12-6.98 (m, 5H), 6.56 (dd, J=3.2, 0.7 Hz, 1H), 6.30 (br. s., 1H), 5.43 (s, 2H), 4.50 (s, 2H). $^{19}$F NMR (471 MHz, DMSO-$d_6$) δ −74.44 (s, 3F), −113.12 (s, 1F). Analytical HPLC Col. A: 6.80 min, 100%; Col. B: 7.74 min, 100%. LC RT=6.80 min (Method A).

Example 65: 7-((1-Benzyl-1H-indazol-4-yl)methyl)-3H-[1,2,3]triazolo[4,5-b]pyridin-5-amine

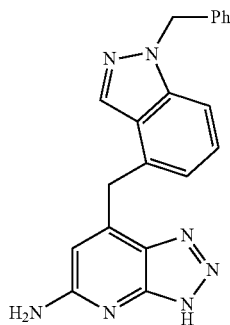 [SMILES: Nc1cc(Cc2cccc3c2cnn3Cc2ccccc2)c2nn[nH]c2n1]

Intermediates Methyl 1-benzyl-1H-indazole-4-carboxylate (65a) and Methyl 2-benzyl-2H-indazole-4-carboxylate (66a)

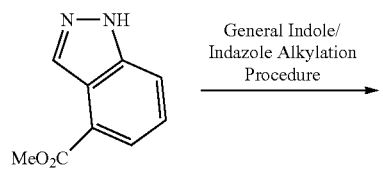

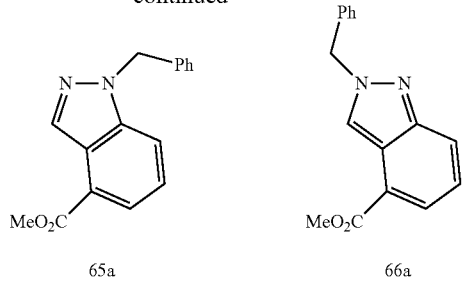

NaH, 60% dispersed in oil (0.125 g, 3.12 mmol) was suspended in DMF (5 mL), and the mixture was cooled to 0° C. with stirring under nitrogen in an ice/salt water bath. To the cold suspension was added a solution of methyl 1H-indazole-4-carboxylate (0.500 g, 2.84 mmol) in DMF (10 mL), and the mixture was stirred for 10 min. Benzyl bromide (0.388 mL, 3.26 mmol) was then added dropwise to the reaction mixture and stirring was continued overnight, allowing the ice bath to melt and the reaction mixture to gradually assume rt. The reaction mixture was diluted with water and extracted with EtOAc. The combined extracts were washed twice with water and once with brine, and then dried over anhydrous $Na_2SO_4$, filtered and evaporated. The mixture of regioisomers was separated by silica gel chromatography using a gradient from 0-100% EtOAc in hexane to provide carboxylate intermediate 65a (0.305 g, 40.4%). MS(ESI) m/z: 267.0 (M+H)+. $^1$H NMR (500 MHz, $CDCl_3$) δ 8.55 (s, 1H), 7.92 (d, J=7.2 Hz, 1H), 7.56 (d, J=8.5 Hz, 1H), 7.40 (d, J=7.4 Hz, 1H), 7.33-7.26 (m, 3H), 7.18 (d, J=7.2 Hz, 2H), 5.65 (s, 2H), 4.02 (s, 3H). NOE observed from $CH_2$ of benzyl to the proton at C7 of the indazole ring system confirming this as the regioisomer with the benzyl at N1. The regioisomeric carboxylate intermediate 66a, methyl 2-benzyl-2H-indazole-4-carboxylate (0.29 g, 38.4%) was also isolated. MS(ESI) m/z: 267.0 (M+H)+. $^1$H NMR (500 MHz, $CDCl_3$) δ 8.45 (s, 1H), 7.96 (dd, J=8.7, 0.7 Hz, 1H), 7.91 (dd, J=7.2, 0.8 Hz, 1H), 7.41-7.28 (m, 6H), 5.64 (s, 2H), 3.95 (s, 3H). NOE observed from $CH_2$ of benzyl to indazole C3 proton confirming this as the regioisomer with the benzyl at $N_2$.

Intermediate 65b: 1-Benzyl-1H-indazole-4-carbaldehyde

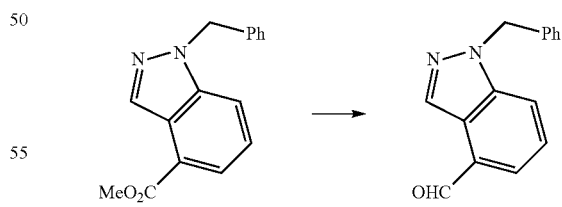

65a was taken through the General Carboxylate Reduction Procedure and General Benzylic Alcohol Oxidation Procedure to provide carboxaldehyde intermediate 65b (0.244 g, 92% over two steps) MS(ESI) m/z: 237.0 (M+H)+.

Example 65

The title compound was prepared from aldehyde 65b following procedures outlined for Example 51. Pale yellow solid. MS(ESI) m/z: 355.9 (M+H)+. 1H NMR (500 MHz, DMSO-d6) δ 8.20 (d, J=1.1 Hz, 1H), 7.59 (d, J=8.5 Hz, 1H), 7.35-7.27 (m, 3H), 7.27-7.20 (m, 3H), 7.08 (d, J=6.9 Hz, 1H), 6.32 (br. s., 1H), 5.64 (s, 2H), 4.57 (s, 2H). Analytical HPLC Col. A: 6.06 min, 100%; Col. B: 6.84 min, 100%. LC RT=6.06 min (Method A).

Example 66: 7-((2-Benzyl-2H-indazol-4-yl)methyl)-3H-[1,2,3]triazolo[4,5-b]pyridin-5-amine

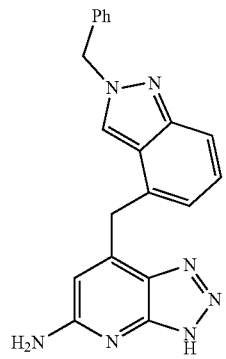 [SMILES: Nc1cc(Cc2cccc3nn(Cc4ccccc4)cc23)c2nn[nH]c2n1]

From methyl-2H-indazole-4-carboxylate 66a as described for Example 65. yellow solid. MS(ESI) m/z: 355.9 (M+H)+. 1H NMR (500 MHz, DMSO-d6) δ 8.49 (d, J=0.8 Hz, 1H), 7.50 (d, J=8.8 Hz, 1H), 7.39-7.25 (m, 5H), 7.20 (dd, J=8.7, 6.7 Hz, 1H), 6.95 (d, J=6.6 Hz, 1H), 6.27 (br. s., 1H), 5.60 (s, 2H), 4.52 (s, 2H). Analytical HPLC Col. A: 5.46 min, >95%; Col. B: 6.16 min, >95%. LC RT=5.46 min (Method A).

Example 67: 7-((1-Methyl-1H-indazol-6-yl)methyl)-3H-[1,2,3]triazolo[4,5-b]pyridin-5-amine

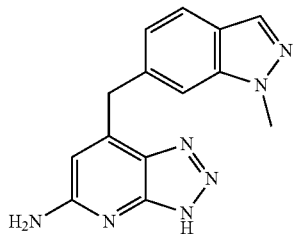 [SMILES: Cn1ncc2ccc(Cc3cc(N)nc4[nH]nnc34)cc21]

Intermediate 67a: 2,6-(2,5-Dimethylpyrrol-1-yl)-4-formylpyridine

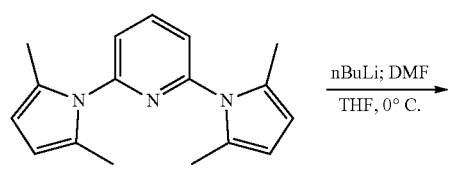

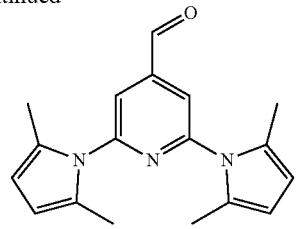

To a solution of 2,6-bis(2,5-dimethyl-1H-pyrrol-1-yl)pyridine (49a, 6.00 g, 22.6 mmol) in THF (100 mL) at 0° C. under argon was added nBuLi (9.5 mL, 24 mmol) dropwise. After 5 min, the reaction mixture was quenched with DMF (8.8 mL, 110 mmol), and the bath was removed. After 2 h, the mixture was extracted from brine with EtOAc. The organic layer was concentrated and purified by silica gel chromatography to furnish 2,6-bis(2,5-dimethyl-1H-pyrrol-1-yl)isonicotinaldehyde (67a, 3.311 g, 11.29 mmol, 49.9% yield). MS(ESI) m/z=294.0. 1H NMR (500 MHz, chloroform-d) δ 10.18 (s, 1H), 7.64 (s, 2H), 5.97 (s, 4H), 2.22 (s, 12H).

Intermediate 67b: 6-((2,6-Bis(2,5-dimethyl-1H-pyrrol-1-yl)pyridin-4-yl)methyl)-1-methyl-1H-indazole

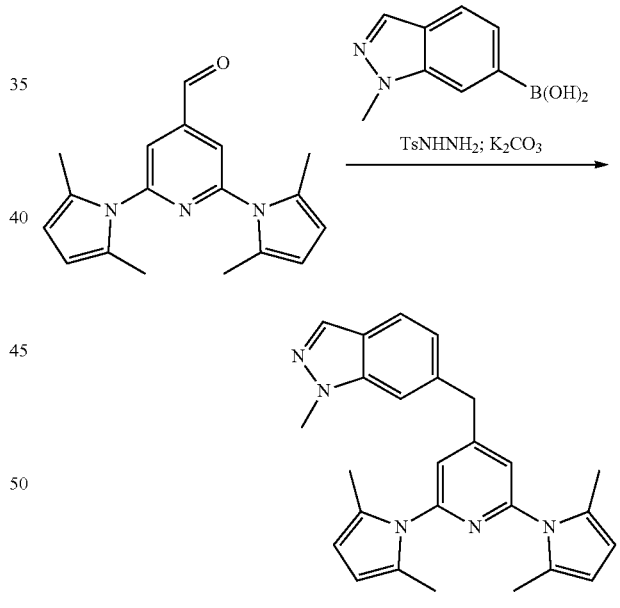

Aldehyde intermediate 67a (0.300 g, 1.02 mmol) was dissolved in dioxane (5.1 mL) and treated with 4-methylbenzenesulfonohydrazide (0.190 g, 1.02 mmol) followed by heating with stirring in an 80° C. oil bath under argon for 1 hr. K2CO3 (0.212 g, 1.53 mmol) was added, followed by (1-methyl-1H-indazol-6-yl)boronic acid (0.270 g, 1.53 mmol) and dioxane (1 mL). The reaction mixture temperature was increased to 110° C., and the reaction mixture was refluxed for 4 hrs then left standing at rt overnight. The reaction mixture was diluted with sat. aq. NaHCO3 solution and extracted with DCM. The combined organic extracts were washed with brine, then dried over anh. MgSO₄, filtered and evaporated. The residue was purified by silica gel chromatography to provide the title compound as a yellow foam (67b, 0.255 g, 60.9%). MS(ESI) m/z: 410.1 (M+H)⁺. ¹H NMR (400 MHz, chloroform-d) δ 7.97 (d, J=1.1 Hz, 1H), 7.70 (d, J=8.2 Hz, 1H), 7.25 (s, 1H), 7.04 (s, 2H), 6.99 (dd, J=8.5, 1.4 Hz, 1H), 5.87 (s, 4H), 4.26 (s, 2H), 4.06 (s, 3H), 2.11 (s, 12H).

Intermediate 67e: 4-((1-Methyl-1H-indazol-6-yl)methyl)pyridine-2,3,6-triamine

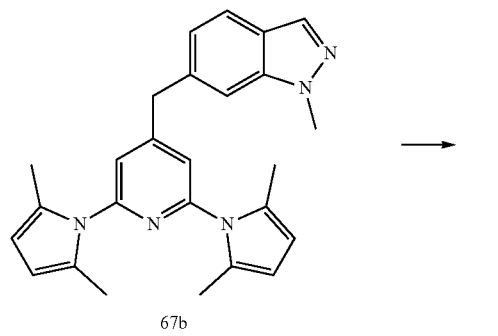

67b

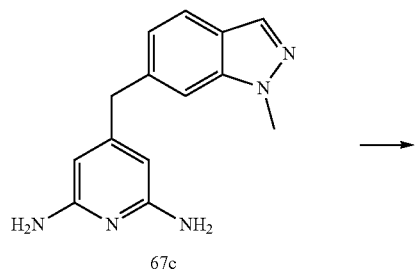

67c

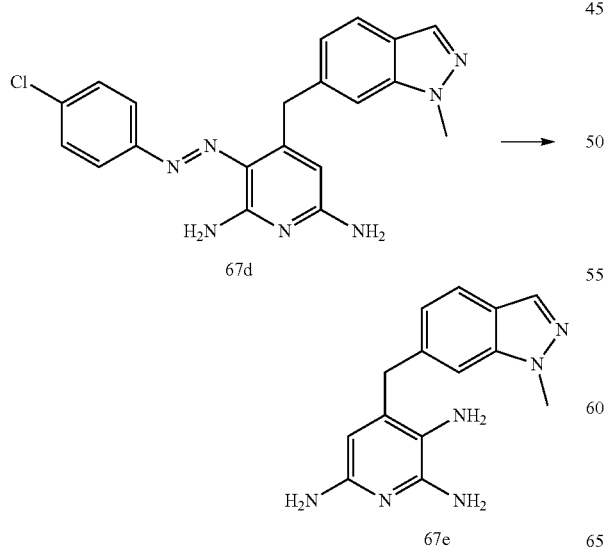

67d

67e 67b was deprotected to the corresponding diamine 67c by treatment with hydroxylamine hydrochloride and Et₃N in 4:1 iPrOH/H₂O at reflux using the General Bispyrrole Deprotection Procedure. The crude diamine 67c was then subjected to General Diazine Formation Procedure to provide (E)-3-((4-chlorophenyl)diazenyl)-4-((1-methyl-1H-indazol-6-yl)methyl)pyridine-2,6-diamine 67d. MS(ESI) m/z: 392.0 (M+H)⁺.

67d (0.106 g, 0.271 mmol) was suspended in EtOH (4 mL), and a solution of sodium dithionite (0.471 g, 2.71 mmol) in water (1.4 mL) was added. The mixture was heated at 50° C. for 1.5 h, cooled to rt and then diluted with water and extracted with EtOAc. The aq. layer was concentrated to remove residual organic solvent, then adsorbed on a pad of C18 which was then washed with water and then eluted with MeOH to recover the product as a yellow residue (67e, 0.029 g, 40.0%), which was taken forward without further purification. MS(ESI) m/z: 269.2 (M+H)⁺.

Example 67

The title compound was prepared from 67e using General Triazole Formation Procedure. MS(ESI) m/z: 280.2 (M+H)⁺. ¹H NMR (500 MHz, methanol-d₄) δ 7.98 (d, J=0.8 Hz, 1H), 7.75 (d, J=8.3 Hz, 1H), 7.59 (s, 1H), 7.16 (dd, J=8.3, 1.4 Hz, 1H), 6.57 (s, 1H), 4.54 (s, 2H), 4.05 (s, 3H). LC RT=4.12 min (Method A).

Example 68: 7-((1-Methyl-1H-indazol-5-yl)methyl)-3H-[1,2,3]triazolo[4,5-b]pyridin-5-amine

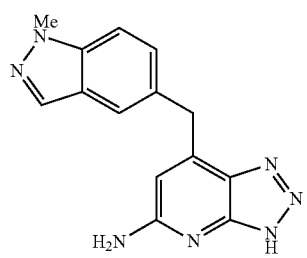 [SMILES: Cn1ncc2cc(Cc3cc(N)nc4[nH]nnc34)ccc21]

Example 68 was prepared as described for Example 67 by substituting (1-methyl-1H-indazol-5-yl)boronic acid in place of (1-methyl-1H-indazol-6-yl)boronic acid, and following procedures described herein. The title compound was obtained as a tan solid. MS(ESI) m/z: 280.1 (M+H)⁺. ¹H NMR (500 MHz, methanol-d₄) δ 7.96 (d, J=0.8 Hz, 1H), 7.76 (d, J=0.8 Hz, 1H), 7.54 (d, J=8.8 Hz, 1H), 7.43 (dd, J=8.7, 1.5 Hz, 1H), 6.54 (s, 1H), 4.48 (s, 2H), 4.05 (s, 3H). LC RT=4.27 min (Method A).

TABLE 2

| Ex. No. | Structure | Name | MS(ESI) (M + H) | $^1$H NMR | LC RT$^a$ (min) |
|---|---|---|---|---|---|
| 2 | 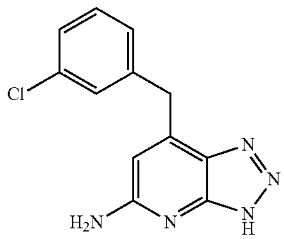 [SMILES: Nc1cc(Cc2cccc(Cl)c2)c2nn[nH]c2n1] | 7-(3-chlorobenzyl)-3H-[1,2,3]triazolo[4,5-b]pyridin-5-amine | 260.1 | (500 MHz, DMSO-d$_6$) δ 7.45 (d, J = 1.7 Hz, 1H), 7.40-7.26 (m, 2H), 6.32 (br. s., 1H), 4.28 (s, 2H) | 5.34 |
| 3 | 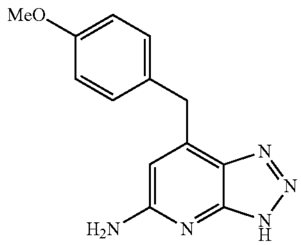 [SMILES: COc1ccc(Cc2cc(N)nc3[nH]nnc23)cc1] | 7-(4-methylbenzyl)-3H-[1,2,3]triazolo[4,5-b]pyridin-5-amine | 240.1 | (500 MHz, methanol-d$_4$) δ 7.23 (d, J = 8.0 Hz, 1H), 7.15 (d, J = 8.0 Hz, 1H), 6.35 (s, 1H), 4.27 (s, 2H), 2.32 (s, 3H) | 5.00 |
| 4 | 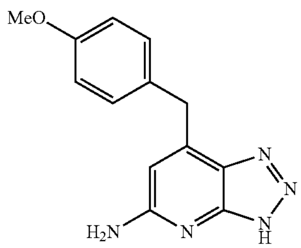 [SMILES: COc1ccc(Cc2cc(N)nc3[nH]nnc23)cc1] | 7-(4-methoxybenzyl)-3H-[1,2,3]triazolo[4,5-b]pyridin-5-amine | 256.1 | (500 MHz, methanol-d$_4$) δ 7.33-7.23 (m, 1H), 6.94-6.86 (m, 1H), 6.35 (s, 1H), 4.25 (s, 2H), 3.79 (s, 3H) | 4.49 |
| 5 | 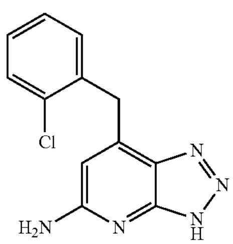 [SMILES: Nc1cc(Cc2ccccc2Cl)c2nn[nH]c2n1] | 7-(2-chlorobenzyl)-3H-[1,2,3]triazolo[4,5-b]pyridin-5-amine | 260.1 | (500 MHz, methanol-d$_4$) δ 7.51-7.45 (m, 1H), 7.44-7.39 (m, 1H), 7.36-7.26 (m, 2H), 6.20 (t, J = 1.1 Hz, 1H), 4.49 (d, J = 0.8 Hz, 2H) | 5.04 |
| 6 | 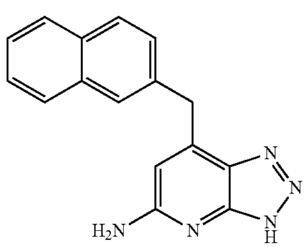 [SMILES: Nc1cc(Cc2ccc3ccccc3c2)c2nn[nH]c2n1] | 7-(naphthalen-2-ylmethyl)-3H-[1,2,3]triazolo[4,5-b]pyridin-5-amine | 276.1 | (500 MHz, methanol-d$_4$) δ 7.89-7.79 (m, 1H), 7.54-7.41 (m, 1H), 6.39 (s, 1H), 4.50 (s, 2H) | 5.71 |
| 8 | 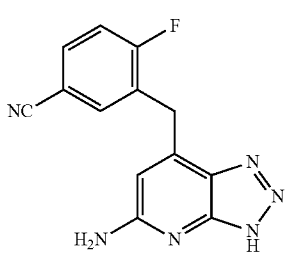 [SMILES: N#Cc1ccc(F)c(Cc2cc(N)nc3[nH]nnc23)c1] | 3-((5-amino-3H-[1,2,3]triazolo[4,5-b]pyridin-7-yl)methyl)-4-fluorobenzonitrile | 269.0 | (500 MHz, DMSO-d$_6$) δ 8.02 (dd, J = 7.0, 2.1 Hz, 1H), 7.90 (ddd, J = 8.5, 4.8, 2.3 Hz, 1H), 7.58-7.43 (m, 1H), 6.23 (br. s., 1H), 4.35 (s, 2H) | 5.20 |

TABLE 2-continued

| Ex. No. | Structure | Name | MS(ESI) (M + H) | ¹H NMR | LC RT$^a$ (min) |
|---|---|---|---|---|---|
| 9 | 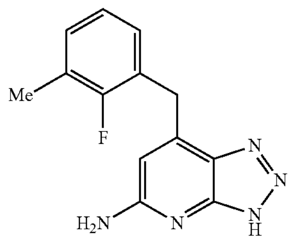 [SMILES: Cc1cccc(Cc2cc(N)nc3[nH]nnc23)c1F] | 7-(2-fluoro-3-methylbenzyl)-3H-[1,2,3]triazolo[4,5-b]pyridin-5-amine | 258.1 | (500 MHz, DMSO-d$_6$) δ 7.29-7.17 (m, 2H), 7.13-6.98 (m, 2H), 6.26 (br. s., 1H), 4.28 (s, 2H), 2.25 (d, J = 1.7 Hz, 3H) | 5.84 |
| 10 | 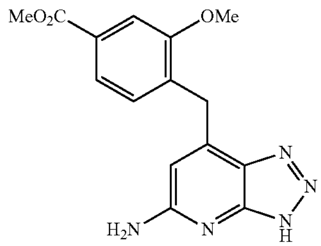 [SMILES: COC(=O)c1ccc(Cc2cc(N)nc3[nH]nnc23)c(OC)c1] | methyl 4-((5-amino-3H-[1,2,3]triazolo[4,5-b]pyridin-7-yl)methyl)-3-methoxybenzoate | 314.0 | (500 MHz, DMSO-d$_6$) δ 7.60-7.52 (m, 2H), 7.39 (d, J = 8.0 Hz, 1H), 6.19 (br. s., 1H), 4.29 (s, 2H), 3.87 (s, 3H), 3.85 (s, 3H) | 5.51 |
| 11 | 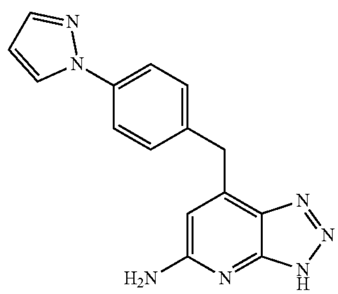 [SMILES: Nc1cc(Cc2ccc(-n3cccn3)cc2)c2nn[nH]c2n1] | 7-(4-(1H-pyrazol-1-yl)benzyl)-3H-[1,2,3]triazolo[4,5-b]pyridin-5-amine | 292.1 | (500 MHz, DMSO-d$_6$) δ 8.47 (d, J = 2.5 Hz, 1H), 7.81 (d, J = 8.5 Hz, 2H), 7.73 (d, J = 1.7 Hz, 1H), 7.48 (d, J = 8.5 Hz, 2H), 6.60-6.47 (m, 1H), 6.37 (br. s., 1H), 4.32 (s, 2H) | 5.18 |
| 12 | 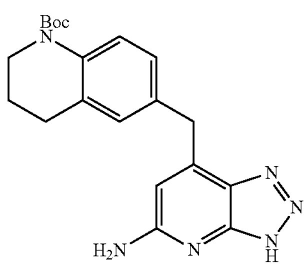 [SMILES: CC(C)(C)OC(=O)N1CCCc2cc(Cc3cc(N)nc4[nH]nnc34)ccc21] | tert-butyl 6-((5-amino-3H-[1,2,3]triazolo[4,5-b]pyridin-7-yl)methyl)-3,4-dihydroquinoline-1(2H)-carboxylate | 325.1 | (500 MHz, DMSO-d$_6$) δ 7.20-7.06 (m, 3H), 6.31 (br. s., 1H), 4.46 (br. s., 2H), 4.21 (s, 2H), 3.53 (t, J = 5.9 Hz, 2H), 2.74 (t, J = 5.9 Hz, 2H), 1.43 (s, 9H) | 6.89 |
| 13 | 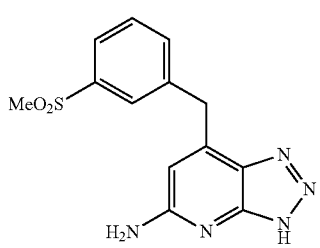 [SMILES: CS(=O)(=O)c1cccc(Cc2cc(N)nc3[nH]nnc23)c1] | 7-(3-(methylsulfonyl)benzyl)-3H-[1,2,3]triazolo[4,5-b]pyridin-5-amine | 304.0 | 1(500 MHz, DMSO-d$_6$) δ 7.94 (s, 1H), 7.82 (d, J = 7.4 Hz, 1H), 7.73 (d, J = 8.3 Hz, 1H), 7.65-7.59 (m, 1H), 6.33 (br. s., 1H), 4.40 (s, 2H), 3.20 (s, 3H) | 4.40 |
| 14 | 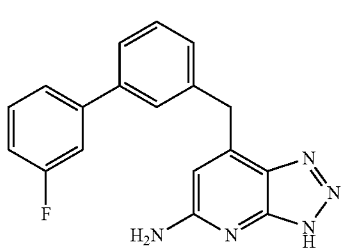 [SMILES: Nc1cc(Cc2cccc(-c3cccc(F)c3)c2)c2nn[nH]c2n1] | 7-((3'-fluoro-[1,1'-biphenyl]-3-yl)methyl)-3H-[1,2,3]triazolo[4,5-b]pyridin-5-amine | 320.1 | (500 MHz, DMSO-d$_6$) δ 7.74-7.63 (m, 3H), 7.53 (d, J = 8.0 Hz, 1H), 7.42 (t, J = 7.6 Hz, 1H), 7.36-7.22 (m, 3H), 6.35 (br. s., 1H), 4.33 (s, 2H) | 6.20 |

TABLE 2-continued

| Ex. No. | Structure | Name | MS(ESI) (M + H) | ¹H NMR | LC RT$^a$ (min) |
|---|---|---|---|---|---|
| 15 | 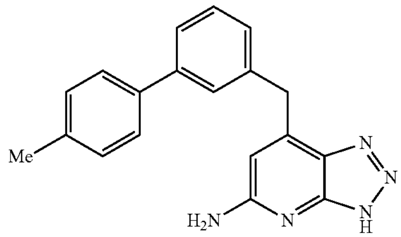 [SMILES: Cc1ccc(-c2cccc(Cc3cc(N)nc4[nH]nnc34)c2)cc1] | 7-((4'-methyl-[1,1'-biphenyl]-3-yl)methyl)-3H-[1,2,3]triazolo[4,5-b]pyridin-5-amine | 316.1 | (500 MHz, DMSO-d$_6$) δ 7.67 (s, 1H), 7.57-7.49 (m, 3H), 7.40 (t, J = 7.7 Hz, 1H), 7.32 (d, J = 7.4 Hz, 1H), 7.28 (d, J = 8.0 Hz, 2H), 6.36 (br. s., 1H), 4.33 (s, 2H), 2.35 (s, 3H) | 7.49 |
| 16 | 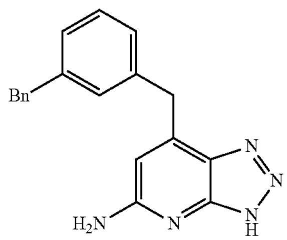 | 7-(3-benzylbenzyl)-3H-[1,2,3]triazolo[4,5-b]pyridin-5-amine | 316.1 | (500 MHz, DMSO-d$_6$) δ 7.31-7.14 (m, 8H), 7.09 (d, J = 7.4 Hz, 1H), 6.31 (br. s., 1H), 4.22 (s, 2H), 3.92 (s, 2H) | 6.50 |
| 18 | 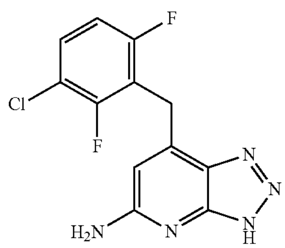 [SMILES: Nc1cc(Cc2c(F)ccc(Cl)c2F)c2nn[nH]c2n1] | 7-(3-chloro-2,6-difluorobenzyl)-3H-[1,2,3]triazolo[4,5-b]pyridin-5-amine | 295.9 | (500 MHz, methanol-d$_4$) δ 7.53 (td, J = 8.7, 5.6 Hz, 1H), 7.11 (td, J = 8.9, 1.7 Hz, 1H), 6.46 (s, 1H), 4.48 (d, J = 1.1 Hz, 2H) | 6.21 |
| 19 | 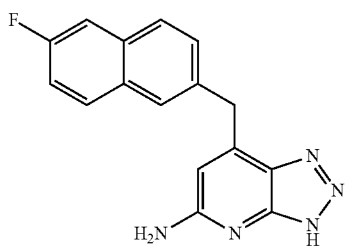 [SMILES: Nc1cc(Cc2ccc3cc(F)ccc3c2)c2nn[nH]c2n1] | 7-((6-fluoronaphthalen-2-yl)methyl)-3H-[1,2,3]triazolo[4,5-b]pyridin-5-amine | 294.0 | (500 MHz, DMSO-d$_6$) δ 7.96 (dd, J = 9.1, 5.8 Hz, 1H), 7.91 (s, 1H), 7.88 (d, J = 8.5 Hz, 1H), 7.68 (dd, J = 10.5, 2.5 Hz, 1H), 7.54 (d, J = 8.5 Hz, 1H), 7.41 (td, J = 8.9, 2.8 Hz, 1H), 6.32 (br. s., 1H), 4.43 (s, 2H) | 6.18 |
| 20 | 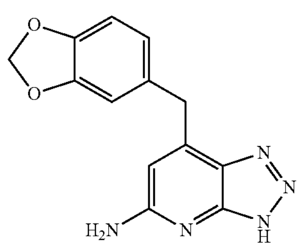 [SMILES: Nc1cc(Cc2ccc3c(c2)OCO3)c2nn[nH]c2n1] | 7-(benzo[d][1,3]dioxol-5-ylmethyl)-3H-[1,2,3]triazolo[4,5-b]pyridin-5-amine | 270.0 | (500 MHz, DMSO-d$_6$) δ 6.93 (d, J = 1.7 Hz, 1H), 6.88-6.85 (m, 1H), 6.83-6.80 (m, 1H), 6.32 (br. s., 1H), 5.98 (s, 2H), 4.17 (s, 2H) | 4.60 |
| 21 | 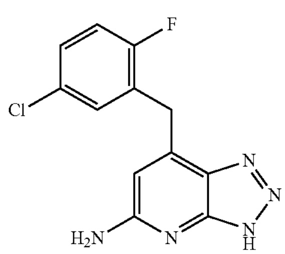 [SMILES: Nc1cc(Cc2cc(Cl)ccc2F)c2nn[nH]c2n1] | 7-(5-chloro-2-fluorobenzyl)-3H-[1,2,3]triazolo[4,5-b]pyridin-5-amine | 278.0 | (500 MHz, DMSO-d$_6$) δ 7.54 (dd, J = 6.6, 2.8 Hz, 1H), 7.41 (ddd, J = 8.7, 4.5, 2.8 Hz, 1H), 7.32-7.27 (m, 1H), 6.25 (br. s., 1H), 4.29 (s, 2H) | 5.66 |

TABLE 2-continued

| Ex. No. | Structure | Name | MS(ESI) (M + H) | ¹H NMR | LC RT$^a$ (min) |
|---|---|---|---|---|---|
| 22 | 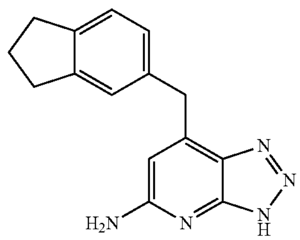 [SMILES: Nc1cc(Cc2ccc3c(c2)CCC3)c2nn[nH]c2n1] | 7-((2,3-dihydro-1H-inden-5-yl)methyl)-3H-[1,2,3]triazolo[4,5-b]pyridin-5-amine | 266.0 | (500 MHz, DMSO-d$_6$) δ 7.18 (s, 1H), 7.16 (d, J = 7.7 Hz, 1H), 7.11-7.08 (m, 1H), 6.33 (br. s., 1H), 4.20 (s, 2H), 2.81 (t, J = 6.3 Hz, 4H), 2.03-1.94 (m, 2H). | 6.00 |
| 23 | 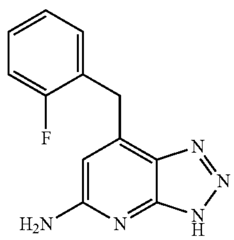 [SMILES: Nc1cc(Cc2ccccc2F)c2nn[nH]c2n1] | 7-(2-fluorobenzyl)-3H-[1,2,3]triazolo[4,5-b]pyridin-5-amine | 244.1 | (500 MHz, DMSO-d$_6$) δ 7.44 (td, J = 7.7, 1.7 Hz, 1H), 7.35 (d, J = 8.0 Hz, 1H), 7.26-7.14 (m, 2H), 6.25 (br. s., 1H), 4.30 (s, 2H) | 4.91 |
| 24 | 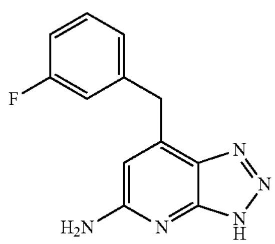 [SMILES: Nc1cc(Cc2cccc(F)c2)c2nn[nH]c2n1] | 7-(3-fluorobenzyl)-3H-[1,2,3]triazolo[4,5-b]pyridin-5-amine | 244.1 | (500 MHz, DMSO-d$_6$) δ 7.38 (td, J = 8.1, 6.3 Hz, 1H), 7.27-7.17 (m, 2H), 7.09 (td, J = 8.7, 2.1 Hz, 1H), 6.34 (br. s., 1H), 4.29 (s, 2H) | 5.01 |
| 25 | 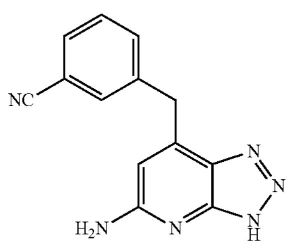 [SMILES: N#Cc1cccc(Cc2cc(N)nc3[nH]nnc23)c1] | 3-((5-amino-3H-[1,2,3]triazolo[4,5-b] pyridin-7-yl)methyl)benzonitrile | 251.1 | (500 MHz, DMSO-d$_6$) δ 7.86 (s, 1H), 7.77-7.66 (m, 2H), 7.59-7.47 (m, 1H), 6.26 (br. s., 1H), 4.33 (s, 2H) | 4.64 |
| 26 | 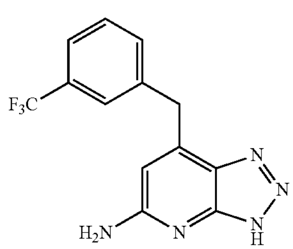 | 7-(3-(trifluoromethyl)benzyl)-3H-[1,2,3]triazolo[4,5-b]pyridin-5-amine | 294.1 | (500 MHz, DMSO-d$_6$) δ 7.77 (s, 1H), 7.70-7.51 (m, 3H), 6.32 (br. s., 1H), 4.38 (s, 2H) | 5.90 |
| 27 | 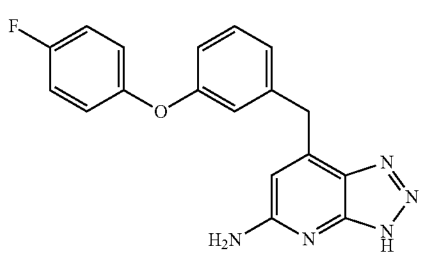 [SMILES: Nc1cc(Cc2cccc(Oc3ccc(F)cc3)c2)c2nn[nH]c2n1] | 7-(3-(4-fluorophenoxy)benzyl)-3H-[1,2,3]triazolo[4,5-b]pyridin-5-amine | 336.1 | (500 MHz, DMSO-d$_6$) δ 7.33 (t, J = 8.0 Hz, 1H), 7.27-7.17 (m, 1H), 7.12 (d, J = 7.7 Hz, 1H), 7.08-6.98 (m, 2H), 6.83 (dd, J = 8.0, 1.9 Hz, 1H), 6.32 (br. s., 1H), 4.25 (s, 2H) | 6.56 |

TABLE 2-continued

| Ex. No. | Structure | Name | MS(ESI) (M + H) | ¹H NMR | LC RT$^a$ (min) |
|---|---|---|---|---|---|
| 28 | 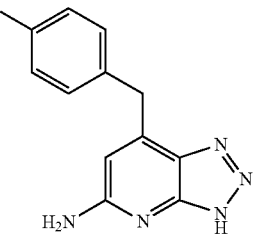 | 7-(4-fluorobenzyl)-3H-[1,2,3]triazolo[4,5-b]pyridin-5-amine | 244.1 | (500 MHz, DMSO-$d_6$) δ 7.40 (dd, J = 8.5, 5.5 Hz, 2H), 7.15 (t, J = 8.9 Hz, 2H), 6.25 (s, 1H), 4.24 (s, 2H) | 5.00 |
| 29 | 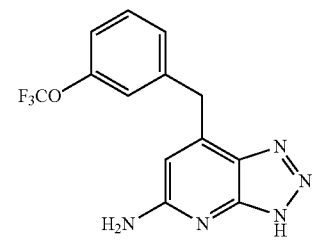 [SMILES: Nc1cc(Cc2cccc(OC(F)(F)F)c2)c2nn[nH]c2n1] | 7-(3-(trifluoromethoxy)benzyl)-3H-[1,2,3]triazolo[4,5-b]pyridin-5-amine | 310.0 | (500 MHz, DMSO-$d_6$) δ 7.53-7.44 (m, 1H), 7.39 (d, J = 6.6 Hz, 2H), 7.25 (d, J = 8.3 Hz, 1H), 6.32 (br. s., 1H), 4.32 (s, 2H) | 6.16 |
| 30 | 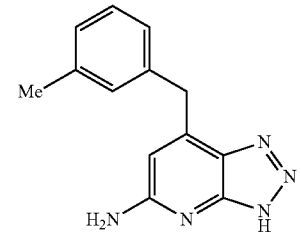 | 7-(3-methylbenzyl)-3H-[1,2,3]triazolo[4,5-b]pyridin-5-amine | 240.0 | (500 MHz, DMSO-$d_6$) δ 7.25-7.18 (m, 1H), 7.18-7.12 (m, 1H), 7.05 (d, J = 7.4 Hz, 1H), 6.30 (br. s., 1H), 4.21 (s, 2H), 2.28 (s, 3H) | 5.29 |
| 31 | 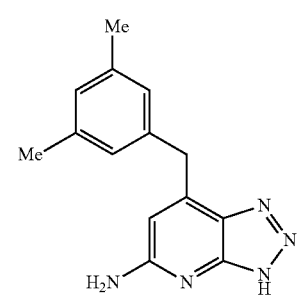 [SMILES: Cc1cc(C)cc(Cc2cc(N)nc3[nH]nnc23)c1] | 7-(3,5-dimethylbenzyl)-3H-[1,2,3]triazolo[4,5-b]pyridin-5-amine | 254.0 | (500 MHz, DMSO-$d_6$) δ 6.94 (s, 1H), 6.86 (s, 1H), 6.28 (br. s., 1H), 4.15 (s, 2H), 2.23 (s, 6H) | 5.76 |
| 32 | 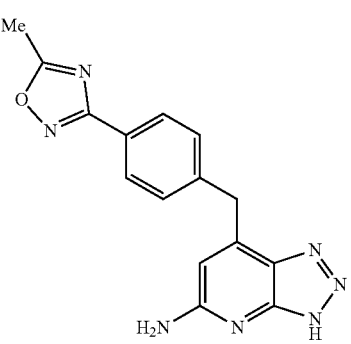 [SMILES: Cc1nc(-c2ccc(Cc3cc(N)nc4[nH]nnc34)cc2)no1] | 7-(4-(5-methyl-1,2,4-oxadiazol-3-yl) benzyl)-3H-[1,2,3]triazolo[4,5-b] pyridin-5-amine | 308.0 | (400 MHz, DMSO-$d_6$) δ 7.96 (d, J = 8.1 Hz, 2H), 7.54 (d, J = 8.3 Hz, 2H), 6.34 (br. s., 1H), 4.34 (s, 2H), 2.66 (s, 3H) | 5.04 |

TABLE 2-continued

| Ex. No. | Structure | Name | MS(ESI) (M + H) | $^1$H NMR | LC RT$^a$ (min) |
|---|---|---|---|---|---|
| 33 | 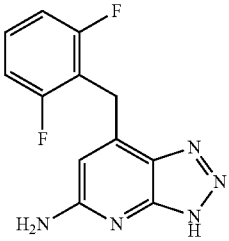 [SMILES: Nc1cc(Cc2c(F)cccc2F)c2nn[nH]c2n1] | 7-(2,6-difluorobenzyl)-3H-[1,2,3]triazolo[4,5-b]pyridin-5-amine | 262.0 | (400 MHz, DMSO-$d_6$) δ 7.52-7.38 (m, 1H), 7.24-7.11 (m, 2H), 6.16 (br. s., 1H), 4.32 (s, 2H) | 5.12 |
| 34 | 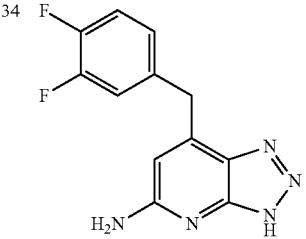 | 7-(3,4-difluorobenzyl)-3H-[1,2,3]triazolo[4,5-b]pyridin-5-amine | 262.0 | (400 MHz, DMSO-$d_6$) δ 7.54-7.32 (m, 1H), 7.29-7.13 (m, 1H), 6.31 (br. s., 1H), 4.27 (s, 2H) | 5.39 |
| 35 | 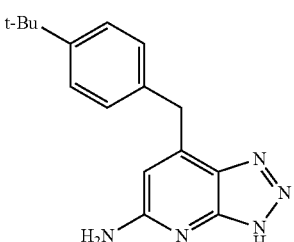 | 7-(4-(tert-butyl)benzyl)-3H-[1,2,3]triazolo[4,5-b]pyridin-5-amine | 282.0 | (500 MHz, DMSO-$d_6$) δ 7.37-7.31 (m, 2H), 7.30-7.23 (m, 2H), 6.34 (br. s., 1H), 4.20 (s, 2H), 1.26 (s, 9H) | 8.19 |
| 36 | 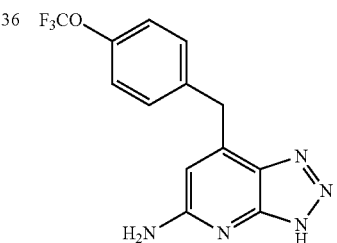 | 7-(4-(trifluoromethoxy)benzyl)-3H-[1,2,3]triazolo[4,5-b]pyridin-5-amine | 310.0 | (500 MHz, methanol-$d_4$) δ 7.54-7.47 (m, 1H), 7.29 (d, J = 8.0 Hz, 1H), 6.57 (s, 1H), 4.42 (s, 2H) | 7.75 |
| 37 | 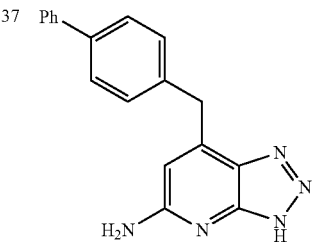 | 7-([1,1'-biphenyl]-4-ylmethyl)-3H-[1,2,3]triazolo[4,5-b]pyridin-5-amine | 302.0 | (500 MHz, DMSO-$d_6$) δ 7.71-7.58 (m, 4H), 7.53-7.41 (m, 4H), 7.39-7.29 (m, 1H), 6.37 (br. s., 1H), 4.30 (s, 2H) | 8.04 |
| 38 | 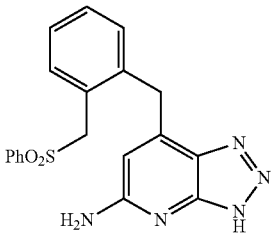 | 7-(2-((phenylsulfonyl)methyl)benzyl)-3H-[1,2,3]triazolo[4,5-b]pyridin-5-amine | 380.0 | (500 MHz, DMSO-$d_6$) δ 7.85-7.72 (m, 1H), 7.67-7.58 (m, 1H), 7.35-7.25 (m, 1H) 7.23-7.17 (m, 1H), 7.14 (d, J = 1.1 Hz, 1H), 6.13 (br. s., 1H), 4.77 (s, 2H), 4.26 (s, 2H) | 6.82 |

TABLE 2-continued

| Ex. No. | Structure | Name | MS(ESI) (M + H) | ¹H NMR | LC RT$^a$ (min) |
|---|---|---|---|---|---|
| 39 | 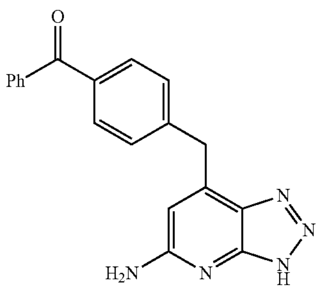 [SMILES: Nc1cc(Cc2ccc(C(=O)c3ccccc3)cc2)c2nn[nH]c2n1] | (4-((5-amino-3H-[1,2,3]triazolo[4,5-b] pyridin-7-yl)methyl)phenyl)(phenyl)methanone | 330.0 | (500 MHz, methanol-d$_4$) δ 7.84-7.75 (m, 1H), 7.69-7.62 (m, 1H), 7.61-7.47 (m, 4H), 6.61 (s, 1H), 4.49 (s, 2H) | 7.90 |
| 40 | 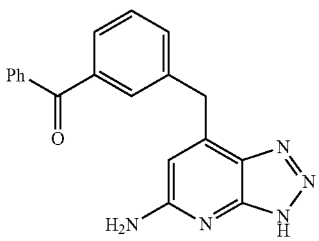 [SMILES: Nc1cc(Cc2cccc(C(=O)c3ccccc3)c2)c2nn[nH]c2n1] | (3-((5-amino-3H-[1,2,3]triazolo[4,5-b] pyridin-7-yl)methyl)phenyl)(phenyl)methanone | 330.0 | (500 MHz, DMSO-d$_6$) δ 7.77-7.71 (m, 3H), 7.71-7.66 (m, 1H), 7.62 (d, J = 7.7 Hz, 1H), 7.59-7.51 (m, 3H), 6.37 (br. s., 1H), 4.37 (s, 2H) | 7.26 |
| 41 | 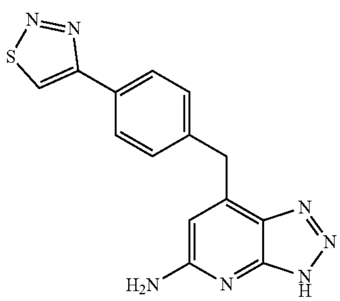 [SMILES: Nc1cc(Cc2ccc(-c3csnn3)cc2)c2nn[nH]c2n1] | 7-(4-(1,2,3-thiadiazol-4-yl)benzyl)-3H-[1,2,3]triazolo[4,5-b]pyridin-5-amine | 309.8 | (500 MHz, methanol-d$_4$) δ 9.25 (s, 1H), 8.12 (d, J = 8.3 Hz, 2H), 7.56 (d, J = 8.3 Hz, 2H), 6.58 (s, 1H), 4.45 (s, 2H) | 6.16 |
| 42 | 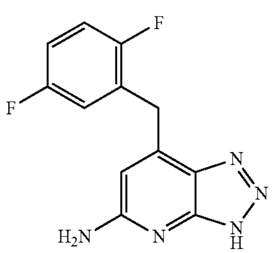 [SMILES: Nc1cc(Cc2cc(F)ccc2F)c2nn[nH]c2n1] | 7-(2,5-difluorobenzyl)-3H-[1,2,3]triazolo[4,5-b]pyridin-5-amine | 262.0 | (500 MHz, DMSO-d$_6$) δ 7.38-7.26 (m, 1H), 7.20 (td, J = 8.2, 4.5 Hz, 1H), 6.26 (br. s., 1H), 4.30 (s, 2H) | 4.84 |
| 43 | 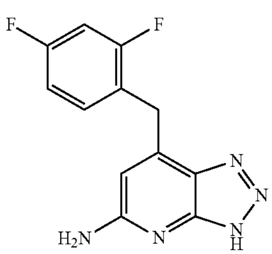 [SMILES: Nc1cc(Cc2ccc(F)cc2F)c2nn[nH]c2n1] | 7-(2,4-difluorobenzyl)-3H-[1,2,3]triazolo[4,5-b]pyridin-5-amine | 262.0 | (500 MHz, DMSO-d$_6$) δ 7.50 (td, J = 8.7, 6.9 Hz, 1H), 7.28 (td, J = 9.8, 2.6 Hz, 1H), 7.10 (td, J = 8.5, 2.2 Hz, 1H), 6.25 (br. s., 1H), 4.29 (s, 2H) | 4.83 |
| 44 | 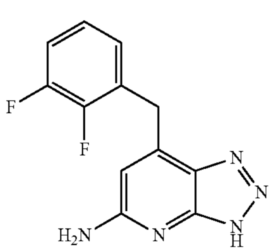 [SMILES: Nc1cc(Cc2cccc(F)c2F)c2nn[nH]c2n1] | 7-(2,3-difluorobenzyl)-3H-[1,2,3]triazolo[4,5-b]pyridin-5-amine | 262.0 | (500 MHz, DMSO-d$_6$) δ 7.42-7.32 (m, 1H), 7.30-7.14 (m, 2H), 6.28 (br. s., 1H), 4.36 (s, 2H) | 5.63 |

TABLE 2-continued

| Ex. No. | Structure | Name | MS(ESI) (M + H) | ¹H NMR | LC RT$^a$ (min) |
|---|---|---|---|---|---|
| 45 | 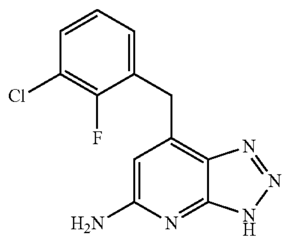 [SMILES: Nc1cc(Cc2cccc(Cl)c2F)c2nn[nH]c2n1] | 7-(3-chloro-2-fluorobenzyl)-3H-[1,2,3]triazolo[4,5-b]pyridin-5-amine | 278.0 | (500 MHz, DMSO-$d_6$) δ 7.58-7.48 (m, 1H), 7.46-7.35 (m, 1H), 7.26-7.17 (m, 1H), 6.24 (br. s., 1H), 4.34 (s, 2H) | 6.05 |
| 50 | 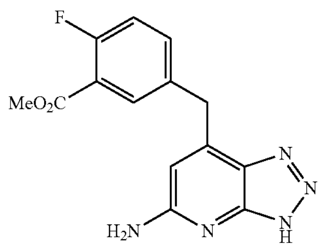 [SMILES: COC(=O)c1cc(Cc2cc(N)nc3[nH]nnc23)ccc1F] | methyl 5-((5-amino-3H-[1,2,3]triazolo[4,5-b]pyridin-7-yl)methyl)-2-fluorobenzoate | 302.1 | (500 MHz, DMSO-$d_6$) δ 7.88 (d, J = 6.6 Hz, 1H), 7.74-7.61 (m, 1H), 7.41-7.23 (m, 1H), 6.29 (br. s., 1H), 4.32 (br. s., 2H), 3.85 (s, 3H) | 4.60 |
| 52 | 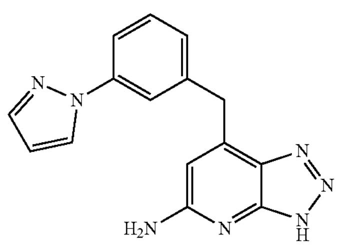 [SMILES: Nc1cc(Cc2cccc(-n3cccn3)c2)c2nn[nH]c2n1] | 7-(3-(1H-pyrazol-1-yl)benzyl)-3H-[1,2,3]triazolo[4,5-b]pyridin-5-amine | 292.1 | (500 MHz, methanol-$d_4$) δ 8.22 (dd, J = 2.5, 0.6 Hz, 1H), 7.80 (t, J = 1.8 Hz, 1H), 7.72 (d, J = 1.7 Hz, 1H), 7.67 (dd, J = 8.1, 1.5 Hz, 1H), 7.49 (t, J = 7.8 Hz, 1H), 7.35 (d, J = 7.7 Hz, 1H), 6.63 (s, 1H), 6.54-6.52 (m, 1H), 4.46 (s, 2H) | 4.82 |
| 53 | 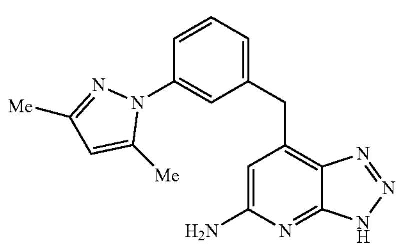 [SMILES: Cc1cc(C)n(-c2cccc(Cc3cc(N)nc4[nH]nnc34)c2)n1] | 7-(3-(3,5-dimethyl-1H-pyrazol-1-yl)benzyl)-3H-[1,2,3]triazolo[4,5-b]pyridin-5-amine | 320.1 | (500 MHz, methanol-$d_4$) δ 7.55-7.47 (m, 3H), 7.40-7.37 (m, 1H), 6.71 (s, 1H), 6.11 (s, 1H), 4.46 (s, 2H), 2.27 (d, J = 0.6 Hz, 3H), 2.26 (s, 3H) | 5.06 |
| 54 | 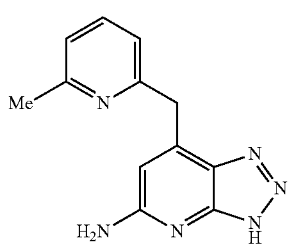 [SMILES: Cc1cccc(Cc2cc(N)nc3[nH]nnc23)n1] | 7-((6-methylpyridin-2-yl)methyl)-3H-[1,2,3]triazolo[4,5-b]pyridin-5-amine | 241.2 | (500 MHz, methanol-$d_4$) δ 8.31 (t, J = 8.0 Hz, 1H), 7.76 (d, J = 7.7 Hz, 1H), 7.52 (s, 1H), 6.71 (s, 1H), 4.42 (s, 2H), 2.81 (s, 3H) | 3.25 |
| 55 | 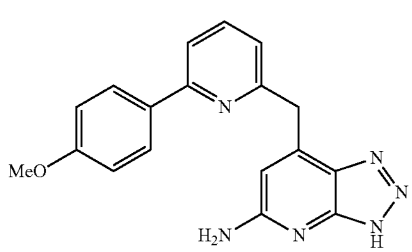 [SMILES: COc1ccc(-c2cccc(Cc3cc(N)nc4[nH]nnc34)n2)cc1] | 7-((6-(4-methoxyphenyl)pyridin-2-yl)methyl)-3H-[1,2,3]triazolo[4,5-b]pyridin-5-amine | 333.1 | (500 MHz, methanol-$d_4$) δ 8.02-7.89 (m, 3H), 7.82 (d, J = 8.5 Hz, 1H), 7.46 (d, J = 7.7 Hz, 1H), 7.08 (d, J = 8.8 Hz, 2H), 6.73 (s, 1H), 4.65 (s, 2H), 3.89 (s, 3H) | 4.41 |

TABLE 2-continued

| Ex. No. | Structure | Name | MS(ESI) (M + H) | ¹H NMR | LC RT[a] (min) |
|---|---|---|---|---|---|
| 56 | 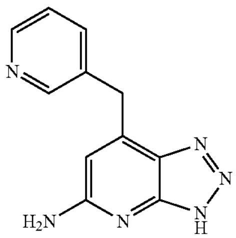 [SMILES: Nc1cc(Cc2cccnc2)c2nn[nH]c2n1] | 7-(pyridin-3-ylmethyl)-3H-[1,2,3]triazolo[4,5-b]pyridin-5-amine | 227.3 | (500 MHz, DMSO-$d_6$) δ 7.19 (s, 1H), 7.08 (s, 1H), 6.98 (s, 1H), 6.31 (br. s., 1H), 4.36 (br. s., 2H) | 1.45 |
| 57 | 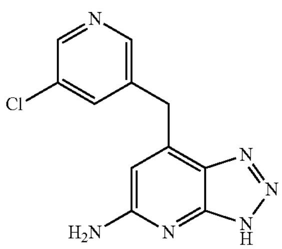 [SMILES: Nc1cc(Cc2cncc(Cl)c2)c2nn[nH]c2n1] | 7-((5-chloropyridin-3-yl)methyl)-3H-[1,2,3]triazolo[4,5-b]pyridin-5-amine | 261.1 | (500 MHz, methanol-$d_4$) δ 8.67-8.48 (m, 1H), 8.12 (s, 1H), 8.09-7.95 (m, 2H), 6.77 (t, J = 1.1 Hz, 1H), 4.49 (s, 2H), 4.19 (s, 1H) | 4.15 |
| 58 | 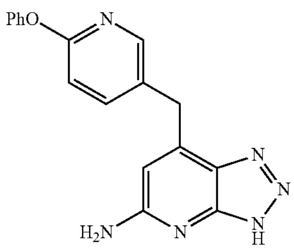 [SMILES: Nc1cc(Cc2ccc(Oc3ccccc3)nc2)c2nn[nH]c2n1] | 7-((6-phenoxypyridin-3-yl)methyl)-3H-[1,2,3]triazolo[4,5-b]pyridin-5-amine | 318.9 | (500 MHz, methanol-$d_4$) δ 8.21 (d, J = 1.9 Hz, 1H), 7.86 (dd, J = 8.5, 2.5 Hz, 1H), 7.50-7.38 (m, 2H), 7.29-7.07 (m, 3H), 7.02-6.89 (m, 1H), 6.67 (s, 1H), 4.86 (s, 23H), 4.39 (s, 2H) | 7.72 |

[a]Unless otherwise noted all LC retention times were obtained according to Analytical Method A.

What is claimed is:

1. The compound of the formula

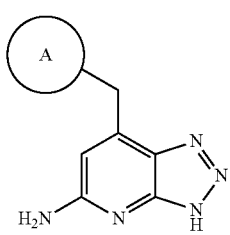

(I)

or a stereoisomer, a tautomer, a pharmaceutically acceptable salt, or a solvate thereof, wherein:

ring A is independently selected from: phenyl, naphthyl and a 6-membered heteroaryl comprising carbon atoms and 1 to 2 nitrogen atoms; wherein each ring moiety is substituted with 0-1 $R^2$ and 0-3 $R^3$;

$R^2$ is independently selected from: halogen, $C_{1-4}$ alkyl substituted with 0-1 OH, $C_{1-4}$ alkoxy, $C_{1-4}$ haloalkyl, $C_{1-4}$ haloalkoxy, CN, $CO_2(C_{1-4}$ alkyl), $SO_2(C_{1-4}$ alkyl), $—(CH_2)_n(X_1)_n(CH_2)_nR^4$, and $—(CH_2)_nCONH(CH_2)_mR^4$;

$X_1$ is independently selected from: O, CO, $NR^1$ and $S(O)_p$;

$R^1$ is independently selected from: H and $C_{1-4}$ alkyl;

$R^3$ is, independently at each occurrence, selected from: OH, halogen, $C_{1-4}$ alkyl, $C_{1-4}$ alkoxy, $C_{1-4}$ haloalkyl, and $C_{1-4}$ haloalkoxy;

alternatively, when $R^2$ and one of the $R^3$s are attached to two adjacent carbon atoms of ring A selected from phenyl and pyridyl, they can be combined with the two attached carbon atoms to form a 5- to 6-membered carbocycle or heterocycle comprising carbon atoms and 0-3 additional heteroatoms selected from N, $NR^b$, O, and $S(O)_p$, wherein said carbocycle or heterocycle is substituted with 0-2 $R^a$;

$R^4$ is independently at each occurrence selected from: $C_{3-6}$ cycloalkyl substituted with 0-3 $R^c$, phenyl substituted with 0-4 $R^c$, and 5- to 10-membered heterocycle comprising carbon atoms and 1-4 heteroatoms selected from N, $NR^b$, O, and S; wherein said heterocycle is substituted with 0-3 $R^c$;

$R^a$ is, independently at each occurrence, selected from: OH, CN, halogen, $C_{1-4}$ alkyl, $C_{1-4}$ alkoxy, $C_{1-4}$ haloalkyl, and $C_{1-4}$ haloalkoxy;

$R^b$ is, independently at each occurrence, selected from: H, $C_{1-4}$ alkyl, $C_{1-4}$ haloalkyl, $CO(C_{1-4}$ alkyl), $CO_2(C_{1-4}$ alkyl), $SO_2(C_{1-4}$ alkyl), $—(CH_2)_t$-phenyl substituted with 0-1 $R^d$;

$R^c$ is, independently at each occurrence, selected from: OH, halogen, $C_{1-6}$ alkyl substituted with 0-1 OH, $C_{1-4}$ alkoxy, $C_{1-4}$ haloalkyl, $C_{1-4}$ haloalkoxy, CN, $CONH_2$, $CONH(C_{1-4}$ alkyl), $CON(C_{1-4}$ alkyl)$_2$, $—(O)_n(CH_2)_t—C_{3-6}$ carbocycle, $—(CH_2)_t(O)_n(C_{3-6}$ carbocycle), and $—(CH_2)_t$-(5- to 6-membered heterocycle comprising carbon atoms and 1-4 heteroatoms selected from N, $NR^b$, O, and S); wherein said carbocycle and heterocycle are substituted with 0-2 $R^d$;

$R^d$ is independently at each occurrence, selected from the group consisting of halogen, $C_{1-4}$ alkyl substituted with 0-1 OH, $C_{1-4}$ haloalkyl, $C_{1-4}$ alkoxy, $C_{1-4}$ haloalkoxy, CN, —$(CH_2)_t(O)_n$—$(C_{3-6}$ carbocycle) and —$(O)_n$$(CH_2)_t$—$(C_{3-6}$ carbocycle);

m is, independently at each occurrence, selected from 1, 2 and 3;

n is, independently at each occurrence, selected from 0 and 1;

p is, independently at each occurrence, selected from 0, 1 and 2; and t is, independently at each occurrence, selected from 0, 1, 2, and 3.

2. A compound according to claim 1 or a stereoisomer, a tautomer, a pharmaceutically acceptable salt, or a solvate thereof, wherein:

ring A is independently phenyl substituted with 0-1 $R^2$ and 0-3 $R^3$, pyridyl substituted with 0-1 $R^2$ and 0-2 $R^3$, or naphthyl substituted with 0-3 $R^3$.

3. A compound according to claim 2 or a stereoisomer, a tautomer, a pharmaceutically acceptable salt, or a solvate thereof, wherein:

ring A is independently phenyl substituted with 0-1 $R^2$ and 0-3 $R^3$ or pyridyl substituted with 0-1 $R^2$ and 0-2 $R^3$.

4. A compound according to claim 3 or a stereoisomer, a tautomer, a pharmaceutically acceptable salt, or a solvate thereof, wherein:

ring A is independently selected from:

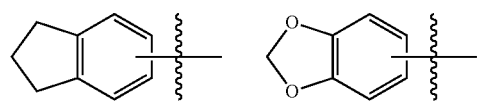

,

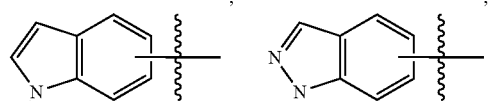

,

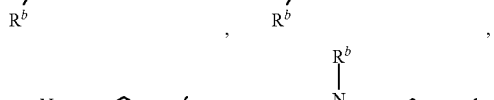

,

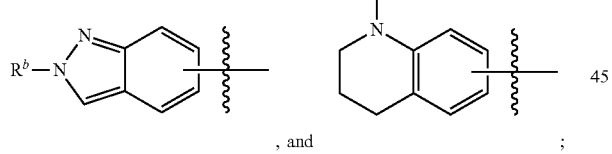

, and ;

wherein each ring moiety is substituted with 0-1 $R^3$.

5. A compound according to claim 1 of formula (II)

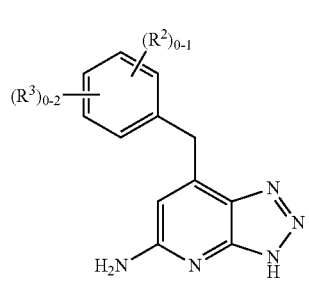

(II)

or a stereoisomer, a tautomer, a pharmaceutically acceptable salt, or a solvate thereof.

6. A compound according to claim 5 or a stereoisomer, a tautomer, a pharmaceutically acceptable salt, or a solvate thereof, wherein:

$R^2$ is independently selected from: halogen, $C_{1-4}$ alkyl, $C_{1-4}$ alkoxy, $C_{1-4}$ haloalkyl, $C_{1-4}$ haloalkoxy, $CO_2(C_{1-4}$ alkyl), CN, Ph, Bn, 3-halo-Ph, 4-$C_{1-4}$ alkyl-Ph, 4-halo-phenoxy, OBn, COPh, —CONHBn, —CONHCH$_2$CH$_2$Ph, $C_{1-4}$ alkyl SO$_2$($C_{1-4}$ alkyl), —CH$_2$SO$_2$Ph, pyrazol-1-yl, 1-Bn-pyrazol-3-yl $C_{1-4}$ alkyl

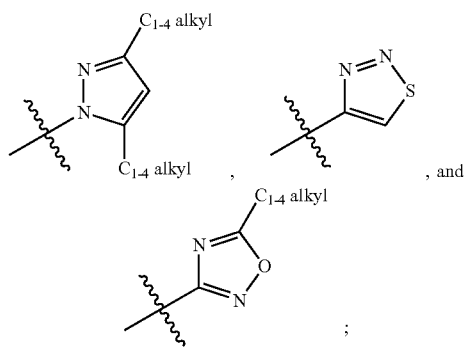

and $R^3$ is independently selected from: halogen, $C_{1-4}$ alkyl, and $C_{1-4}$ alkoxy.

7. A compound according to claim 6 or a stereoisomer, a tautomer, a pharmaceutically acceptable salt, or a solvate thereof, wherein:

$R^2$ is independently selected from: F, Cl, Me, t-Bu, OMe, CF$_3$, OCF$_3$, CO$_2$Me, CN, Ph, Bn, 3-F-Ph, 4-Me-Ph, 4-F-phenoxy, OBn, COPh, —CONH(CH$_2$)$_{1-2}$Ph, SO$_2$Me, —CH$_2$SO$_2$Ph, pyrazol-1-yl, 1-Bn-pyrazol-3-yl,

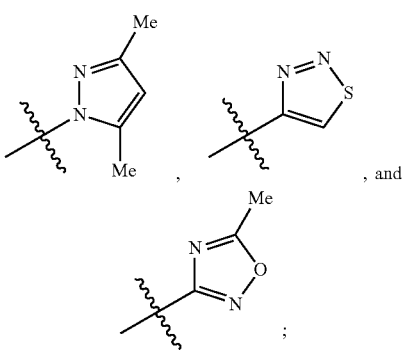

and $R^3$ is independently selected from: F, Me and OMe.

8. A compound according to claim 1, wherein the compound is selected from any one of Examples 1 to 68 or a stereoisomer, a tautomer, or a pharmaceutically acceptable salt thereof.

9. A pharmaceutical composition, comprising a pharmaceutically acceptable carrier and a compound of claim 1, or a stereoisomer, a tautomer, or a pharmaceutically acceptable salt thereof.

* * * * *